(12) United States Patent
Setoi et al.

(10) Patent No.: US 6,495,542 B1
(45) Date of Patent: Dec. 17, 2002

(54) BENZAMIDE DERIVATIVES AS VASOPRESSIN ANTAGONISTS

(75) Inventors: Hiroyuki Setoi, Ibaraki (JP); Takehiko Ohkawa, Ishigemachi (JP); Yuki Sawada, Ushiku (JP); Kazuhiko Osoda, Tsukuba (JP); Teruo Oku, deceased, late of Tokyo (JP), by Noriko Oku, Chikako Oku, Tomohito Oku, legal representatives

(73) Assignee: Fujisawa Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 09/600,857

(22) PCT Filed: Jan. 11, 1999

(86) PCT No.: PCT/JP99/00072

§ 371 (c)(1),
(2), (4) Date: Oct. 16, 2000

(87) PCT Pub. No.: WO99/37637

PCT Pub. Date: Jul. 29, 1999

(30) Foreign Application Priority Data

Jan. 27, 1998 (AU) .............................. PP 1500

(51) Int. Cl.[7] .......................... A61K 31/55; A61P 9/00; C07D 223/16

(52) U.S. Cl. .................. 514/213.01; 540/593

(58) Field of Search ....................... 540/593; 514/213.01

(56) References Cited

U.S. PATENT DOCUMENTS 6,054,457 A  4/2000  Setoi et al. ................. 514/255

FOREIGN PATENT DOCUMENTS

| EP | 0 620 216 A | 10/1994 |
|----|-------------|---------|
| JP | 4-154765 | 5/1992 |
| JP | 9-20779 | 1/1997 |
| JP | 9-221476 | 8/1997 |
| WO | WO 91/05549 | 5/1991 |
| WO | WO 95/29152 | 11/1995 |

Primary Examiner—Brenda Coleman
(74) Attorney, Agent, or Firm—Oblon, Spivak, McClelland, Maier & Neustadt, P.C.

(57) ABSTRACT

A compound of formula (I):

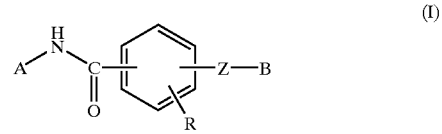

wherein A is an optionally substituted heterocyclic group, R is a lower alkoxy; Z is C=O or $CH_2$; and B is benzazapinyl, which may be optionally substituted, or a salt thereof, that possesses vasopressin antagonistic activity and is useful as a vasopressin antagonist.

8 Claims, No Drawings

BENZAMIDE DERIVATIVES AS VASOPRESSIN ANTAGONISTS

This application is a national-stage entry under 35 U.S.C. §371 of PCT/JP99/00072, filed Jan. 11, 1999.

The present invention relates to new benzamide derivatives and salts thereof which are useful as medicaments.

BACKGROUND ART

Some benzamide derivatives have been known as vasopressin antagonist, for example, in PCT International Publication Nos. WO 91/05549 and WO 95/29152, EP Publication No. 0620216, and Japanese Patent Unexamined Publication Nos. 154765/1992 and 221476/1997.

DISCLOSURE OF THE INVENTION

This invention relates to new benzamide derivatives and salts thereof.

More particularly, it relates to new benzamide derivatives and salts thereof which exhibit activities such as vasopressin antagonistic activity, to pharmaceutical compositions comprising the same and to methods for the treatment and/or prophylaxis of cerebrovascular disease (e.g. cerebral edema, cerebral infarction, etc.), depressant, anxiety and the like in human beings and animals.

One object of this invention is to provide new and useful benzamide derivatives and salts thereof which possess the aforesaid activities.

Another object of this invention is to provide processes for the preparation of said benzamide derivatives and salts thereof.

A further object of this invention is to provide pharmaceutical compositions comprising, as an active ingredient, said benzamide derivatives or pharmaceutically acceptable salts thereof.

Still further object of this invention is to provide methods for the treatment and/or prophylaxis of the aforesaid diseases in human beings and animals, using said benzamide derivatives and pharmaceutically acceptable salts thereof.

The object benzamide derivatives of this invention are new and can be represented by the following formula (I):

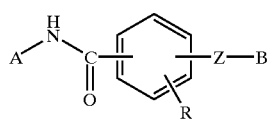

wherein

A is an optionally substituted heterocyclic group;
R is a lower alkoxy;
Z is C=O or CH$_2$; and
B is a saturated or unsaturated condensed ring group selected from the group consisting of benzazepinyl, benzodiazepinyl, pyridoazepinyl, pyridodiazepinyl, thienoazepinyl, benzoxazepinyl, benzothiazepinyl, imidazobenzazepinyl, pyridobenzoxazepinyl and indolinyl, each member being optionally substituted, preferably, by the following formula (II):

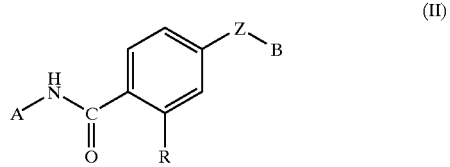

wherein A, B, R and Z are each as defined above, or a salt thereof.

The object compound (I) of the present invention can be prepared according to the following reaction schemes.

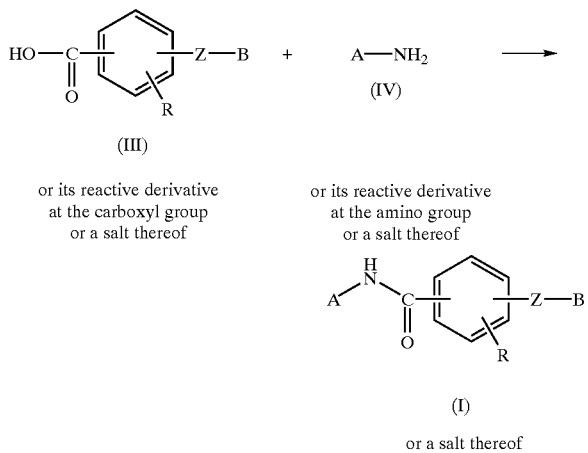

(wherein B, Z, and R are each defined above.)

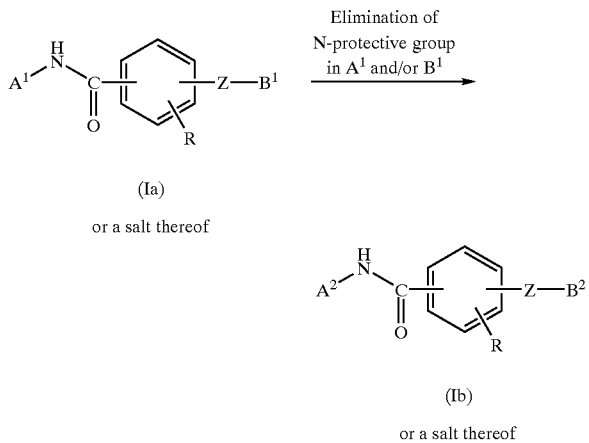

(wherein $A^1$ is a heterocyclic group substituted with an N-protective group, a protected amino or a substituent having protected amino, $B^1$ is any one of benzazepinyl, thienoazepinyl, benzodiazepinyl, pyridoazepinyl, pyridodiazepinyl, thienoazepinyl, benzoxazepinyl, benzothiazepinyl, imidazobenzazepinyl, pyridobenzoxazepinyl and indolinyl, which is substituted with an N-protective group, a protected amino or a substituent having protected amino, $A^2$ is a heterocyclic group not substituted with an N-protective group or substituted with amino or a substituent having amino, $B^2$ is any one of benzazepinyl, benzodiazepinyl, pyridoazepinyl, pryridodiazepinyl, thienoazepinyl, benzoxazepinyl, benzothiazepinyl, imidazobenzazepinyl, pyridobenzoxazepinyl and indolinyl, which is not substituted with an N-protective group or substituted with amino or a substituent having amino, and Z and R are each defined above.)

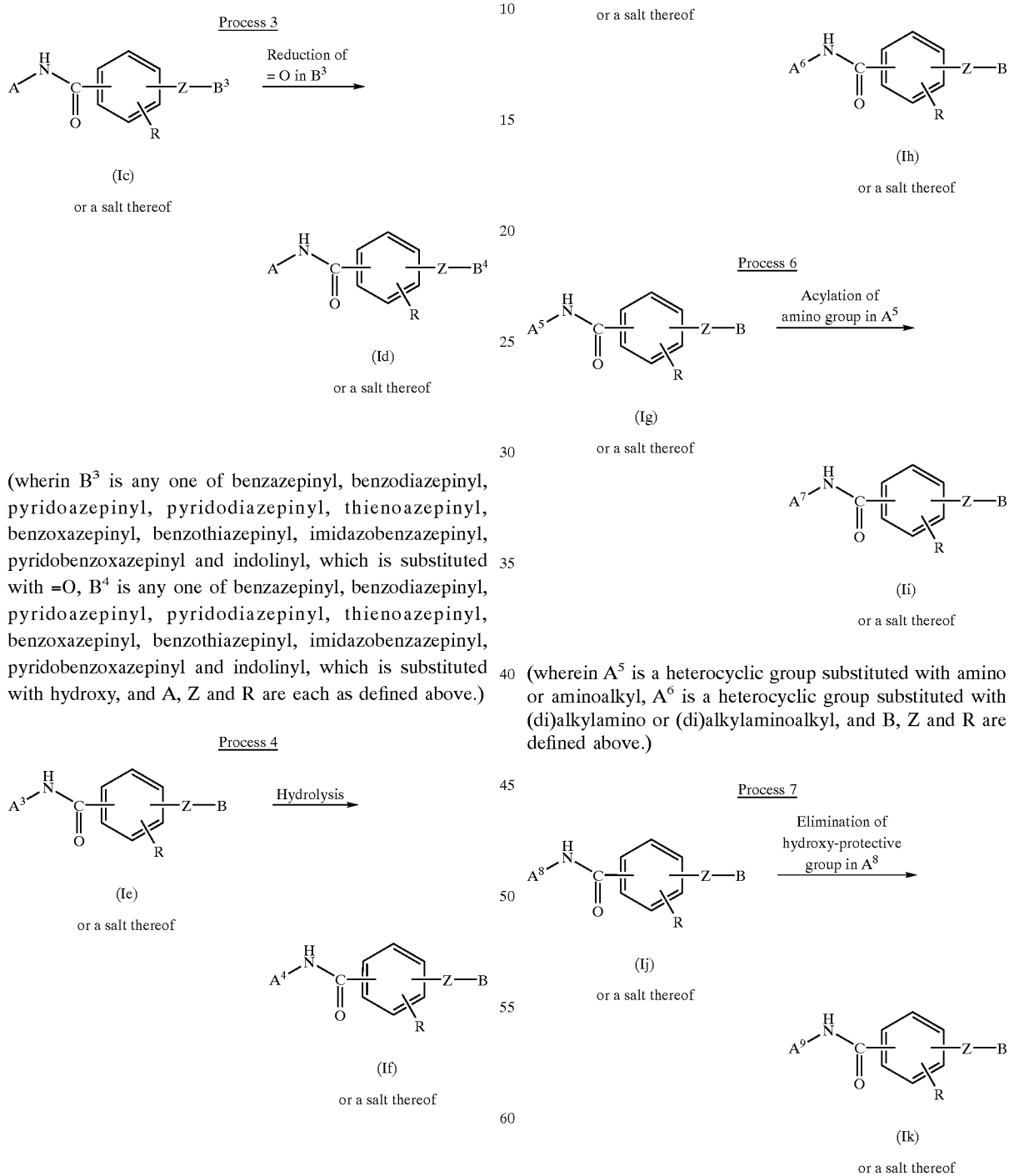

Process 3

(Ic)
or a salt thereof

Reduction of = O in $B^3$ →

(Id)
or a salt thereof (wherin $B^3$ is any one of benzazepinyl, benzodiazepinyl, pyridoazepinyl, pyridodiazepinyl, thienoazepinyl, benzoxazepinyl, benzothiazepinyl, imidazobenzazepinyl, pyridobenzoxazepinyl and indolinyl, which is substituted with =O, $B^4$ is any one of benzazepinyl, benzodiazepinyl, pyridoazepinyl, pyridodiazepinyl, thienoazepinyl, benzoxazepinyl, benzothiazepinyl, imidazobenzazepinyl, pyridobenzoxazepinyl and indolinyl, which is substituted with hydroxy, and A, Z and R are each as defined above.)

Process 4

(Ie)
or a salt thereof

Hydrolysis →

(If)
or a salt thereof (wherein $A^3$ is a heterocyclic group substituted with phthaloylaminoalkyl, $A^4$ is a heterocyclic group substituted with aminoalkyl, and B, Z and R are each defined above.)

Process 5

(Ig)
or a salt thereof

Alkylation of amino group in $A^5$ →

(Ih)
or a salt thereof

Process 6

(Ig)
or a salt thereof

Acylation of amino group in $A^5$ →

(Ii)
or a salt thereof (wherein $A^5$ is a heterocyclic group substituted with amino or aminoalkyl, $A^6$ is a heterocyclic group substituted with (di)alkylamino or (di)alkylaminoalkyl, and B, Z and R are defined above.)

Process 7

(Ij)
or a salt thereof

Elimination of hydroxy-protective group in $A^8$ →

(Ik)
or a salt thereof (wherein $A^8$ is a heterocyclic group substituted with protected hydroxyalkyl, $A^9$ is a heterocyclic group substituted with hydroxyalkyl, and B, Z and R are each as defined above.)

Process 8

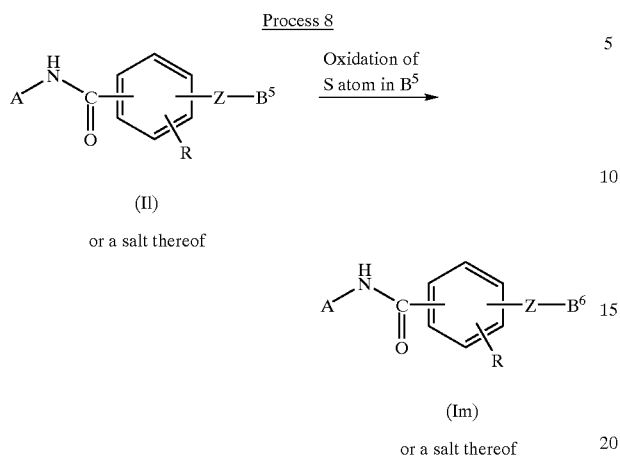

(wherein $B^5$ is saturated or unsaturated benzothiazepinyl, $B^6$ is a saturated or unsaturated S-oxo-benzothiazepinyl, and A, Z and R are each as defined above.)

Process 9

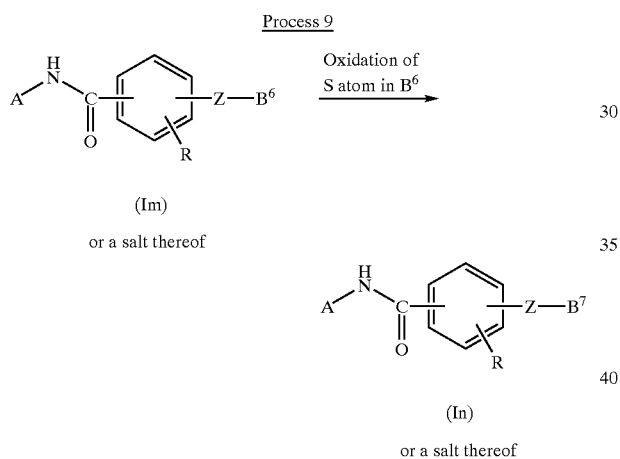

(wherein $B^7$ is a saturated or unsaturated S,S-dioxo-benzothiazepinyl, and A, Z, $B^6$ and R are each as defined above.)

Suitable salts of the object compound [I] are pharmaceutically acceptable, conventional non-toxic mono- or di-salts and include a metal salt such as an alkali metal salt (e.g. sodium salt, potassium salt) and an alkaline earth metal salt (e.g. calcium salt, magnesium salt), an ammonium salt, an organic base salt (e.g. trimethylamine salt, triethylamine salt, pyridine salt, picoline salt, dicyclohexylamine salt, N,N-dibenzylethylenediamine salt), an organic acid addition salt (e.g. formate, acetate, trifluoroacetate, maleate, tartrate, methanesulfonate, benzenesulfonate, p-toluenesulfonate), an inorganic acid addition salt (e.g. hydrochloride, hydrobromide, hydroiodide, sulfate, phosphate) and a salt with an amino acid (e.g. arginine salt, aspartic acid salt, glutamic acid salt).

Suitable examples of the various definitions to be included within the scope of the invention, which are given in the description of the present specification, are explained in detail in the following.

The term "lower" is intended to mean a group having 1 to 6 carbon atoms, preferably 1 to 4 carbon atoms, unless otherwise provided.

Suitable "lower alkoxy" includes straight or branched ones such as methoxy, ethoxy, propoxy, isopropoxy, butoxy, isobutoxy, tert-butoxy, pentoxy, 2-ethylpropoxy and hexoxy, in which the preferred one is $(C_1-C_4)$alkoxy.

Suitable "heterocyclic group" defined for A of the formula (I) includes saturated or unsaturated, monocyclic or polycyclic group such as unsaturated 3 to 8-membered (more preferably 5 to 7-membered) heteromonocyclic group containing 1 to 4 nitrogen atom(s), for example, azepinyl (e.g. 1H-azepinyl), pyrrolyl, pyrrolinyl, imidazolyl, pyrazolyl, pyridyl and its N-oxide, dihydropyridyl, pyrimidinyl, pyrazinyl, pyridazinyl, triazolyl (e.g. 4H-1,2,4-triazolyl, 1H-1,2,3-triazolyl, 2H-1,2,3-triazolyl), tetrazolyl (e.g. 1H-tetrazolyl, 2H-tetrazolyl), etc.;

saturated 3 to 8-membered (more preferably 5 to 7-membered) heteromonocyclic group containing 1 to 4 nitrogen atom(s), for example, perhydroazepinyl (e.g. perhydro-1H-azepinyl), pyrrolidinyl, imidazolidinyl, piperidyl, piperazinyl, etc.;

unsaturated condensed heterocyclic group containing 1 to 4 nitrogen atom(s), for example, indolyl, isoindolyl, indolizinyl, benzimidazolyl, quinolyl, isoquinolyl, indazolyl, benzotriazolyl, quinoxalinyl, imidazopyridyl (e.g. imidazo[4,5-c]pyridyl), tetrahydroimidazopyridyl (e.g. 4,5,6,7-tetrahydroimidazo[4,5-c]pyridyl), etc.;

saturated condensed heterocyclic group containing 1 to 4 nitrogen atom(s), for example, 7-azabicyclo[2.2.1] heptyl, 3-azabicyclo[3.2.2]-nonanyl, etc.;

unsaturated 3 to 8-membered (more preferably 5 or 6-membered) heteromonocyclic group containing 1 or 2 oxygen atom(s) and 1 to 3 nitrogen atom(s), for example, oxazolyl, isoxazolyl, oxadiazolyl (e.g. 1,2,4-oxadiazolyl, 1,3,4-oxadiazolyl, 1,2,5-oxadiazolyl), etc.;

saturated 3 to 8-membered (more preferably 5 or 6-membered) heteromonocyclic group containing 1 or 2 oxygen atom(s) and 1 to 3 nitrogen atom(s), for example, morpholinyl (e.g. 2-morpholinyl, 3-morpholinyl, 4-morpholino), sydnonyl, etc.;

unsaturated condensed heterocyclic group containing 1 or 2 oxygen atom(s) and 1 to 3 nitrogen atom(s), for example, benzoxazolyl, benzoxadiazolyl, etc.;

unsaturated 3 to 8-membered (more preferably 5 or 6-membered) heteromonocyclic group containing 1 or 2 sulfur atom(s) and 1 to 3 nitrogen atom(s), for example, thiazolyl, isothiazolyl, thiadiazolyl (e.g. 1,2,3-thiadiazolyl, 1,2,4-thiadiazolyl, 1,3,4-thiadiazolyl, 1,2,5-thiadiazolyl), dihydrothiazinyl, etc.;

saturated 3 to 8-membered (more preferably 5 or 6-membered) heteromonocyclic group containing 1 or 2 sulfur atom(s) and 1 to 3 nitrogen atom(s), for example, thiazolidinyl, etc.;

unsaturated condensed heterocyclic group containing 1 or 2 sulfur atom(s) and 1 to 3 nitrogen atom(s), for example, benzothiazolyl, benzothiadiazolyl, etc.;

saturated condensed heterocyclic group containing 1 to 4 nitrogen atom(s);

unsaturated 3 to 8-membered (more preferably 5 or 6-membered) heteromonocyclic group containing 1 or 2 sulfur atom(s), for example, thienyl, dihydrodithiinyl, etc.;

unsaturated 3 to 8-membered (more preferably 5 or 6-membered) heteromonocyclic group containing an oxygen atom, for example, furyl, etc.;

unsaturated 3 to 8-membered (more preferably 5 or 6-membered) heteromonocyclic group containing an oxygen atom and 1 or 2 sulfur atom(s), for example, dihydrooxathiinyl, etc.;

unsaturated condensed heterocyclic group containing 1 or 2 sulfur atom(s), for example, benzothienyl, benzodithiinyl, etc.; and unsaturated condensed heterocyclic group containing an oxygen atom and 1 or 2 sulfur atom(s), for example, benzoxathiinyl, etc.

Suitable "substituent(s)" of "heterocyclic group" includes lower alkyl optionally substituted with hydroxy, protected hydroxy, amino, protected amino, alkyl-substituted amino, lower alkoxy, acylamino or N-containing heterocyclic group; N-protective group; lower alkoxy; haloalkyl; amino optionally substituted with lower alkyl, acyl or N-protective group; carbamoyl optionally substituted with lower alkyl; acyl; acylamino; aminoalkylamino optionally substituted with lower alkyl or N-protective group; and N-containing heterocyclic group optionally substituted with lower alkyl, amino optionally substituted with lower alkyl or N-protective group, Suitable "lower alkyl" and "lower alkyl" moiety in "optionally substituted with lower alkyl" include straight or branched ($C_1$-$C_6$)alkyl such as methyl, ethyl, propyl, isopropyl, butyl, isobutyl, tert-butyl, pentyl, 2-ethylpropyl and hexyl, in which the preferred one is ($C_1$-$C_4$)alkyl.

Suitable "lower alkoxy" and "lower alkoxy" moiety in "optionally substituted with lower alkoxy" include straight or branched ($C_1$–$C_6$)alkoxy such as methoxy, ethoxy, propoxy, isopropoxy, butoxy, isobutoxy, tert-butoxy, pentoxy, 2-ethylpropoxy and hexoxy, in which the preferred one is ($C_1$–$C_4$)alkoxy.

Suitable "N-protective group", "N-protective group" moiety in "optionally substituted with N-protective group" and amino-protective group of "a protected amino" include aryl(lower)alkyl such as mono- or di- or triphenyl(lower) alkyl (e.g. benzyl, phenethyl, 1-phenylethyl, benzhydryl, trityl) and acyl as explained hereinbelow.

Suitable "acyl", "acyl" moiety in "optionally substituted with acyl or acylamino" and "acyl" moiety in "acylamino" include aliphatic acyl, aromatic acyl, arylaliphatic acyl and heterocyclic-aliphatic acyl derived from caboxylic acid, carbonic acid, carbamic acid or sulfonic acid.

Suitable examples of the acyl group thus explained are lower alkanoyl (e.g. formyl, acetyl, propionyl, hexanoyl, pivaloyl), mono(or di or tri)halo(lower)alkanoyl (e.g. chloroacetyl, trifluoroacetyl), lower alkoxycarbonyl (e.g. methoxycarbonyl, ethoxycarbonyl, tert-butoxycarbonyl, tert-pentyloxycarbonyl, hexyloxycarbonyl), mono(or di or tri)halo(lower)alkoxycarbonyl (e.g. chloromethoxycarbonyl, dichloroethoxycarbonyl, trichloroethoxycarbonyl), aroyl (e.g. benzoyl, toluoyl, xyloyl, naphthoyl), aryl(lower)alkanoyl such as phenyl-(lower)alkanoyl (e.g. phenylacetyl, phenylpropionyl), aryloxycarbonyl (e.g. phenoxycarbonyl, naphthyloxycarbonyl), aryloxy(lower)alkanoyl such as phenoxy(lower)alkanoyl (e.g. phenoxyacetyl, phenoxypropionyl), arylglyoxyloyl (e.g. phenylglyoxyloyl, naphthylglyoxyloyl), aryl(lower) alkoxycarbonyl which may have suitable substituent(s) such as phenyl(lower)alkoxycarbonyl which may have nitro or lower alkoxy (e.g. benzyloxycarbonyl, phenethyloxycarbonyl, p-nitrobenzyloxy-carbonyl, p-methoxybenzyloxycarbonyl), thienylacetyl, imidazolylacetyl, furylacetyl, tetrazolylacetyl, triazolylacetyl, thiadiazolylacetyl, thienylpropionyl, thiadiazolylpropionyl, lower alkylsulfonyl (e.g. methylsulfonyl, ethylsulfonyl, propylsulfonyl, isopropylsulfonyl, pentylsulfonyl, butylsulfonyl), arylsulfonyl (e.g. phenylsulfonyl, tolylsufonyl, xylylsufonyl, naphthylsufonyl) and aryl(lower)alkylsufonyl such as phenyl(lower)alkylsufonyl (e.g. benzylsufonyl, phenethylsufonyl, benzhydrylsufonyl).

Examples of preferable "protected amino" are aryl(lower)alkylamino, lower alkanoylamino and lower alkoxycarbonylamino, more preferable ones are triphenyl (Ci4)alkylamino, ($C_1$–$C_4$)alkanoylamino and ($C_1$–$C_4$) alkoxycarbonylamino, and the most preferable ones are tritylamino, formamido, acetamido and tert-butoxycarbonylamino.

Suitable "alkyl" moiety in "alkyl-substituted amino", "haloalkyl" and "aminoalkylamino" include straight or branched ($C_1$–$C_6$)alkyl such as methyl, ethyl, propyl, isopropyl, butyl, isobutyl, tert-butyl, pentyl, 2-ethylpropyl and hexyl, in which the preferred one is ($C_1$–$C_4$)alkyl.

Examples of preferable "alkyl-substituted amino" are methylamino, ethylamino, propylamino, isopropylamino, butylamino, isobutylamino, tert-butylamino, pentylamino, hexylamino, dimethylamino, diethylamino, dipropylamino, diisopropylamino, dibutylamino, diisobutylamino, di-tert-butylamino, dipentylamino, dihexylamino or the like.

Examples of preferable "haloalkyl" are fluoromethyl, 1-fluoroethyl, 2-fluoroethyl, 1-fluoropropyl, 2-fluoropropyl, 3-fluoropropyl, 4-fluorobutyl, 5-fluoropentyl, 6-fluorohexyl, chloromethyl, 1-chloroethyl, 2-chloroethyl, 1-chloropropyl, 2-chloropropyl, 3-chloropropyl, 4-chlorobutyl, 5-chloropentyl, 6-chlorohexyl, bromomethyl, 1-bromoethyl, 2-bromoethyl, 1-bromopropyl, 2-bromopropyl, 3-bromopropyl, 4-bromobutyl, 5-bromopentyl, 6-bromohexyl, iodomethyl, 1-iodoethyl, 2-iodoethyl, 1-iodopropyl, 2-iodopropyl, 3-iodopropyl, 4-iodobutyl, 5-iodopentyl, 6-iodohexyl, trifluoromethyl, 2,2,2-trifluoroethyl, trichloromethyl, 2,2,2-chloroethyl tribromomethyl, triuodomethyl, or the like.

Examples of preferable "aminoalkylamino" and "aminoalkylamino" moiety in "optionally substituted with aminoalkylamino" are aminomethylamino, aminoethylamino, aminopropylamino, aminoisopropylamino, aminobutylamino, aminoisobutylamino, amino-tert-butylamino, aminopentylamino, aminohexylamino, di(aminomethyl)amino, di(aminoethyl)amino, di(aminopropyl)amino, di(aminoisopropyl)amino, di(aminobutyl)amino, di(aminoisobutyl)amino, di(amino-tert-butyl)amino, di(aminopentyl)amino, di(aminohexyl) amino or the like.

Suitable "N-containing heterocyclic group" and "N-containing heterocyclic group" moiety in "optionally substituted with N-containing heterocyclic group" include ones containing N atom(s) from among those exemplified above with regard to "heterocyclic group".

Suitable "protected hydroxy" includes hydroxy protected by a conventional protective group, for example, substituted lower alkoxy such as lower alkoxy(lower)alkoxy (e.g. methoxymethoxy), lower alkoxy(lower)alkoxy(lower) alkoxy (e.g. methoxyethoxymethoxy) and substituted or unsubstituted aryl(lower)alkoxy (e.g. benzyloxy, nitrobenzyloxy); acyloxy such as lower alkanoyloxy (e.g. acetoxy, propionyloxy, pivaloyloxy), aroyloxy (e.g. benzoyloxy, fluorenecarbonyloxy), lower alkoxycarbonyloxy (e.g. methoxycarbonyloxy, ethoxycarbonyloxy, propoxycarbonyloxy, isopropoxycarbonyloxy, butoxycarbonyloxy, isobutoxycarbonyloxy, tert-butoxycarbonyloxy, pentyloxycarbonyloxy, hexyloxycarbonyloxy), substituted or unsubstituted aryl (lower)alkoxycarbonyloxy (e.g. benzyloxy-carbonyloxy, bromobenzyloxycarbonyloxy), arenesulfonyloxy (e.g.

benzenesulfonyloxy, tosyloxy) and alkanesulfonyloxy (e.g. methanesulfonyloxy, ethanesulfonyloxy); tri(lower) alkylsilyloxy (e.g. trimethylsilyloxy); tetrahydropyranyloxy; and the like.

Examples of preferable "heterocyclic group" defined for A of the formula (I) are substituted or unsubstituted 1H-benzimidazol-4-yl such as 2-methyl-1-tert-butoxycarbonyl-1H-benzimidazol-4-yl, 2-methyl-1H-benzimidazol-4-yl, 2-phthaloylaminomethyl-1H-benzimidazol-4-yl, 2-aminomethyl-1H-benzimidazol-4-yl, 2-dimethylaminomethyl-1H-benzimidazol-4-yl, 2-methanesulfonylaminomethyl-1H-benzimidazol-4-yl, 2-(morpholin-4-yl)methyl-1H-benzimidazol-4-yl, 2-(4-tert-butoxycarbonylpiperazin-1-yl)methyl-1H-benzimidazol-4-yl, 2-(piperazin-1-yl) methyl-1H-benzimidazol-4-yl, 2-tert-butyldimethylsiloxymethyl-1H-benzimidazol-4-yl, 2-hydroxymethyl-1H-benzimidazol-4-yl, 2-(imidazol-1-yl)-1H-benzimidazol-4-yl, 2-tert-butoxycarbonylamino-1H-benzimidazol-4-yl, 2-amino-1H-benzimidazol-4-yl, 2-acetamido-1H-benzimidazol-4-yl, 2-methylsulfonylamino-1H-benzimidazol-4-yl, 2-trifluoromethyl-1H-benzimidazol-4-yl, 1,2-dimethyl-1H-benzimidazol-4-yl, 2-dimethylamino-1H-benzimidazol-4-yl, 1H-benzimidazol-4-yl, 2-methoxy-1H-benzimidazol-4-yl, 2-methoxymethyl-1H-benzimidazol-4-yl, 2-ethyl-1H-benzimidazol-4-yl, 1-tert-butoxycarbonyl-2-[2-(N-methyl-N-tert-butoxycarbonylamino)ethylamino]-1H-benzimidazol-4-yl, 2-[2-(methylamino)ethylamino]-1H-benzimidazol-4-yl, 2-n-propyl-1H-benzimidazol-4-yl, 2-(4-methylpiperazin-1-yl)-1H-benzimidazol-4-yl, 2-[N-[2-(dimethylamino)ethyl]-N-methylamino]-1H-benzimidazol-4-yl, 2-[2-(dimethylamino)ethylamino]-1H-benzimidazol-4-yl, 2-(morpholin-4-yl)-1H-benzimidazol-4-yl, 2-(imidazol-1-yl)methyl-1H-benzimidazol-4-yl, 2-[4-(dimethylamino)piperidin-1-yl]-1H-benzimidazol-4-yl, 2-(N,N-dimethylcarbamoyl)-1H-benzimidazol-4-yl, 1-tert-butoxycarbonyl-2-[N-(2-tert-butoxycarbonylaminoethyl)-N-methylamino]-1H-benzimidazol-4-yl and 2-[N-(aminoethyl)-N-methylamino]-1H-benzimidazol-4-yl;

substituted or unsubstituted 3H-benzimidazol-4-yl such as 2,3-dimethyl-3H-benzimidazol-4-yl;

substituted or unsubstituted benzoxazol-4-yl such as 2-methylbenzoxazol-4-yl; and substituted or unsubstituted 1H-indazol-7-yl.

"Condensed ring group" defined for B of the formula (I) may be saturated or unsaturated. Unsaturated condensed ring group includes partly unsaturated condensed ring group.

Suitable "substituent(s)" in "condensed ring group" defined for B of the formula (I) include lower alkyl, halogen, hydroxy, N-protective group, =O and =CH$_2$.

Suitable "lower alkyl" and "N-protective group" are the same as those defined above with regard to the substituents of "heterocyclic group".

Suitable "halogen" includes fluoro, chloro, bromo and iodo.

Examples of preferable "saturated or unsaturated condensed ring group" defined for B of the formula (I) are unsaturated benzazepinyl such as 2,3,4,5-tetrahydro-1H-1-benzazepin-1-yl, 2,3,4,5-tetrahydro-5-oxo-1H-1-benzazepin-1-yl, 2,3,4,5-tetrahydro-5-hydroxy-1H-1-benzazepin-1-yl, 2,3,4,5-tetrahydro-5-methylene-1H-1-benzazepin-1-yl, 2,3,4,5-tetrahydro-7-methyl-1H-1-benzazepin-1-yl, 2,3,4,5-tetrahydro-7-chloro-1H-1-benzazepin-1-yl and 2,3,4,5-tetrahydro-9-methyl-1H-1-benzazepin-1-yl;

unsaturated benzodiazepinyl such as 2,3,4,5-tetrahydro-4-oxo-1H-1,5-benzodiazepin-1-yl, 2,3,4,5-tetrahydro-5-oxo-1H-1,4-benzodiazepin-1-yl, 3-methyl-4-oxo-2,3,4,5-tetrahydro-1H-1,3-benzodiazepin-1-yl and 4-methyl-2,3,4,5-tetrahydro-1H-1,4-benzodiazepin-1-yl;

unsaturated pyridoazepinyl such as 6,7,8,9-tetrahydro-5H-pyrido[2,3-b]azepin-9-yl, 2,3,4,5-tetrahydro-1H-pyrido[3,4-b]azepin-1-yl, 2-methyl-6,7,8,9-tetrahydro-5H-pyrido[3,2-b]azepin-5-yl and 2,3,4,5-tetrahydro-1H-pyrido[4,3-b]azepin-1-yl;

unsaturated pyridodiazepinyl such as 5-methyl-2,3,4,5-tetrahydro-1H-pyrido[2,3-b][1,4]diazepin-1-yl;

unsaturated thienoazepinyl such as 2,3-dimethyl-5,6,7,8-tetrahydro-4H-thieno[2,3-b]azepin-8-yl and 5,6,7,8-tetrahydro-4H-thieno[3,2-b]azepin-4-yl;

unsaturated benzoxazepinyl such as 2,3,4,5-tetrahydro-1,5-benzoxazepin-5-yl and 1,2,3,5-tetrahydro-4,1-benzoxazepin-1-yl;

unsaturated benzothiazepinyl such as 2,3,4,5-tetrahydro-1,5-benzothiazepin-5-yl, 1-oxo-2,3,4,5-tetrahydro-1,5-benzothiazepin-5-yl, 1,1-dioxo-2,3,4,5-tetrahydro-1,5-benzothiazepin-5-yl, 1,2,3,5-tetrahydro-4,1-benzothiazepin-1-yl, 4-oxo-1,2,3,5-tetrahydro-4,1-benzothiazepin-1-yl and 4,4-dioxo-1,2,3,5-tetrahydro-4,1-benzothiazepin-1-yl;

unsaturated imidazobenzazepinyl such as 2-methyl-1,4,5,6-tetrahydro-imidazo[4,5-d][1]benzazepin-6-yl;

unsaturated pyridobenzoxazepinyl such as 5,6-dihydro-pyrido[2,3-b][1,5]benzoxazepin-6-yl; and substituted indolinyl such as 3,3-dimethylindolin-1-yl.

The processes for preparing the object compound of the present invention are explained in detail in the following.

Process 1

The object compound (I) or a salt thereof can be prepared by reacting a compound (III) or its reactive derivative at the carboxyl group or a salt thereof, with a compound (IV) or its reactive derivative at the amino group or a salt thereof.

Suitable salts of the compounds (III) and (IV) may be the same as those exemplified above with regard to the compound (I).

Suitable reactive derivative at the carboxy group of the compound (III) includes an acid halide, an acid anhydride, an activated amide and an activated ester. Examples of suitable reactive derivatives may be an acid chloride; an acid azide; a mixed acid anhydride with an acid such as substituted phosphoric acid (e.g. dialkylphosphoric acid, phenylphosphoric acid, diphenylphosphoric acid, dibenzylphosphoric acid, halogenated phosphoric acid), dialkylphosphorous acid, sulfurous acid, thiosulfuric acid, sulfuric acid, sulfonic acid (e.g. methanesulfonic acid), aliphatic carboxylic acid (e.g. acetic acid, propionic acid, butyric acid, isobutyric acid, pivalic acid, pentanoic acid, isopentanoic acid, 2-ethylbutyric acid, trichloroacetic acid), or aromatic carboxylic acid (e.g. benzoic acid); a symmetrical acid anhydride; an activated amide with imidazole, 4-substituted imidazole, dimethylpyrazole, triazole, tetrazole or 1-hydroxy-1H-benzotriazole; or an activated ester (e.g. cyanomethyl ester, methoxymethyl ester, dimethyliminomethyl [(CH$_3$)$_2$N$^+$=CH—] ester, vinyl ester, propargyl ester, p-nitrophenyl ester, 2,4-dinitrophenyl ester, trichlorophenyl ester, pentachlorophenyl ester, mesylphenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester) or an ester with a N-hydroxy compound (e.g. N,N- dimethylhydroxylamine, 1-hydroxy-2-(1H)-pyridone, N-hydroxysuccinimide, N-hydroxyphthalimide, 1-hydroxy-1H-benzotriazole). These reactive derivatives can optionally be selected according to the kind of the compound (III) to be used.

Suitable salts of the compound (III) and its reactive derivative can be referred to the ones as exemplified for the compound (I).

Suitable reactive derivative at the amino group of the compound (IV) includes Schiff's base type imino or its tautomeric enamine type isomer formed by the reaction of the compound (IV) with a carbonyl compound such as aldehyde or ketone; a silyl derivative formed by the reaction of the compound (IV) with a silyl compound such as bis(trimethylsilyl)acetamide, mono(trimethylsilyl)acetamide or bis(trimethylsilyl)urea; and a derivative formed by reaction of the compound (IV) with phosphorus trichloride or phosgene.

Suitable salts of the compound (IV) and its reactive derivative can be referred to the ones as exemplified for the compound (I).

The reaction is usually carried out in a conventional solvent such as water, an alcohol (e.g. methanol, ethanol), acetone, dioxane, acetonitrile, chloroform, methylene chloride, ethylene chloride, tetrahydrofuran, ethyl acetate, N,N-dimethylacetamide, N,N-dimethylformamide, pyridine or any other organic solvent which does not adversely influence the reaction. These conventional solvents may also be used in a mixture with water.

In this reaction, when the compound (III) is used in a free acid form or its salt form, the reaction is preferably carried out in the presence of a conventional condensing agent such as N,N'-dicyclohexylcarbodiimide; N-cyclohexyl-N'-morpholinoethylcarbodiimide; N-cyclohexyl-N'-(4-diethylaminocyclohexyl)carbodiimide; N,N'-diethylcarbodiimide; N,N'-diisopropylcarbodiimide; N-ethyl-N'-(3-dimethylaminopropyl)carbodiimide; N,N'-carbonylbis-(2-methylimidazole); pentamethyleneketene-N-cyclohexylimine; diphenylketene-N-cyclohexylimine; ethoxyacetylene; 1-alkoxy-1-chloroethylene; trialkyl phosphite; ethyl polyphosphate; isopropyl polyphosphate; phosphorus oxychloride (phosphoryl chloride); phosphorus trichloride; phosphorus pentachloride; thionyl chloride; mesyl chloride; oxalyl chloride; lower alkyl haloformate (e.g. ethyl chloroformate, isopropyl chloroformate); triphenylphosphine; 2-ethyl-7-hydroxybenzisoxazolium salt; 2-ethyl-5-(m-sulfophenyl) isoxazolium hydroxide intramolecular salt; 1-(p-chlorobenzenesulfonyloxy)-6-chloro-1H-benzotriazole; or so-called Vilsmeier reagent prepared by the reaction of N,N-dimethylformamide with thionyl chloride, phosgene, trichloromethyl chloroformate, phosphorus oxychloride or methanesulfonyl chloride.

The reaction may also be carried out in the presence of an inorganic or organic base such as alkali metal carbonates, alkali metal hydrogencarbonates, tri(lower)alkylamine, pyridide, N-(lower)alkylmorpholine or N,N-di(lower)alkylbenzylamine.

The reaction temperature is not critical, and the reaction is usually carried out under cooling to warming.

Process 2

The object compound (Ib) or a salt thereof can be prepared by subjecting a compound (Ia) or a salt thereof to elimination reaction of the N-protective group in A' and/or B'.

Suitable salts of the compounds (Ia) and (Ib) may be the same as those exemplified above with regard to the compound (I).

This reaction is carried out in accordance with a conventional method such as hydrolysis or reduction.

The hydrolysis is preferably carried out in the presence of a base or an acid including Lewis acid.

Suitable base includes, for example, inorganic bases such as alkali metal hydroxides (e.g. sodium hydroxide, potassium hydroxide), alkaline earth metal hydroxides (e.g. magnesium hydroxide, calcium hydroxide), alkali metal carbonates (e.g. sodium carbonate, potassium carbonate), alkaline earth metal carbonates (e.g. magnesium carbonate, calcium carbonate), alkali metal hydrogencarbonates (e.g. sodium hydrogencarbonate, potassium hydrogencarbonate); and organic bases such as trialkylamines (e.g. trimethylamine, triethylamine), picoline, 1,5-diazabicyclo[4.3.0]non-5-ene, 1,4-diazabicyclo[2.2.2]octane, and 1,8-diazabicyclo[5.4.0]undec-7-ene.

Suitable acid includes organic acids (e.g. formic acid, acetic acid, propionic acid, trichloroacetic acid, trifluoroacetic acid) and inorganic acids (e.g. hydrochloric acid, hydrobromic acid, sulfuric acid).

The elimination using Lewis acid such as trihaloacetic acid (e.g. trichloroacetic acid, trifluoroacetic acid) is preferably carried out in the presence of cation trapping agents (e.g. anisole, phenol).

The reaction is usually carried out in a solvent such as water, an alcohol (e.g. methanol, ethanol), methylene chloride, tetrahydrofuran, a mixture thereof or any other solvent which does not adversely influence the reaction. A liquid base or acid can be also used as the solvent. The reaction temperature is not critical and the reaction is usually carried out under cooling to warming.

The reaction method applicable to the elimination reaction includes chemical reduction and catalytic reduction.

Suitable reducing agent to be used in chemical reduction is a combination of a metal (e.g. tin, zinc, iron) or metallic compound (e.g. chromium chloride, chromium acetate) and an organic or inorganic acid (e.g. formic acid, acetic acid, propionic acid, trifluoroacetic acid, p-toluenesulfonic acid, hydrochloric acid, hydrobromic acid).

Suitable catalysts to be used in catalytic reduction are conventional ones such as platinum catalysts (e.g. platinum plate, spongy platinum, platinum black, colloidal platinum, platinum oxide, platinum wire), palladium catalysts (e.g. spongy palladium, palladium black, palladium oxide, palladium on carbon, colloidal palladium, palladium on barium sulfate, palladium on barium carbonate), nickel catalysts (e.g. reduced nickel, nickel oxide, Raney nickel), cobalt catalysts (e.g. reduced cobalt, Raney cobalt), iron catalysts (e.g. reduced iron, Raney iron) and copper catalysts (e.g. reduced copper, Raney copper, Ullman copper).

The reduction is usually carried out in a conventional solvent which does not adversely influence the reaction, such as water, methanol, ethanol, propanol, N,N-dimethylformamide, or a mixture thereof. Additionally, in case that the above-mentioned acids to be used in chemical reduction are liquid, they can also be used as a solvent. Further, a suitable solvent to be used in catalytic reduction may be the above-mentioned solvents, and other conventional solvents such as diethyl ether, dioxane and tetrahydrofuran, or a mixture thereof.

The reaction temperature of this reduction is not critical and the reaction is usually carried out under cooling to warming.

Process 3

The object compound (Id) or a salt thereof can be prepared by subjecting a compound (Ic) or a salt thereof to reduction of =O in $B^3$.

Suitable salts of the compounds (Ic) and (Id) may be the same as those exemplified above with regard to the compound (I).

This reaction is carried out in accordance with a conventional method using a reducing agent.

Suitable reducing agent includes alkali metal borohydride (e.g. sodium borohydride, sodium cyanoborohydride).

The reaction is usually carried out in a conventional solvent which does not adversely influence the reaction, such as water, alcohol (e.g. methanol, ethanol, propanol), or a mixture thereof.

The reaction temperature of this reaction is not critical and the reaction is usually carried out under cooling to warming.

Process 4

The object compound (If) or a salt thereof can be prepared by subjecting a compound (Ie) or a salt thereof to hydrolysis.

Suitable salts of the compounds (Ie) and (If) may be the same as those exemplified above with regard to the compound (I).

This reaction is carried out in accordance with a conventional method using a base or an acid including Lewis acid.

Suitable base includes an inorganic or organic base such as alkaline metals (e.g. sodium, potassium), alkaline earth metals (e.g. magnesium, calcium), hydrides thereof, hydroxides thereof, carbonate salts thereof, bicarbonate salts thereof, alkylamine (e.g. methylamine, trimethylamine, triethylamine), picoline, 1,5-diazabicyclo[4.3.0]non-5-ene, 1,4-diazabicyclo[2.2.2]octane, 1,8-diazabicyclo[5.4.0]undec-7-ene.

Suitable acid includes organic acids (e.g. formic acid, acetic acid, propionic acid, trichloroacetic acid, trifluoroacetic acid), inorganic acids (e.g. hydrochloric acid, hydrobromic acid, sulfuric acid, hydrogen chloride, hydrogen bromide, hydrogen fluoride) and acid addition salt compounds (e.g. pyridine hydrochloride).

The reaction is usually carried out in a conventional solvent which does not adversely influence the reaction, such as water, dioxane, alcohol (e.g. methanol, ethanol, propanol), acetonitrile, tetrahydrofuran, acetic acid, N,N-dimethylformamide, or a mixture thereof.

The reaction temperature of this reaction is not critical and the reaction is usually carried out under cooling to warming.

Process 5

The object compound (Ih) or a salt thereof can be prepared by reacting a compound (Ig) or a salt thereof with an alkylating agent.

Suitable salts of the compounds (Ig) and (Ih) may be the same as those exemplified above with regard to the compound (I).

This reaction is carried out in accordance with a conventional method using a conventional alkylating agent.

Suitable alkylating agent includes lower alkyl halides (e.g. methyl iodide, ethyl iodide); combination of carbonyl compounds such as aliphatic ketones (e.g. acetone, ethylmethylketone), carboaldehydes (e.g. formaldehyde, ethanal) and orthocarbonates (e.g. orthoformate), and reducting agents such as formic acid, sodium borohydride, sodium cyanoborohydride, palladium-carbon used in chemical reduction or catalytic reduction.

In case that a lower alkyl halide is used as an alkylating agent, the reaction may preferably be carried out in the presence of alkaline metals (e.g. sodium, potassium), alkaline earth metals (e.g. magnesium, calcium), hydride thereof, hydroxide thereof, carbonate salts thereof, bicarbonate salts thereof, and organic base (e.g. tri(lower)alkylamine, N,N-di(lower)alkylaniline).

The reaction is usually carried out in a conventional solvent which does not adversely influence the reaction, such as water, dioxane, alcohol (e.g. methanol, ethanol, propanol), acetonitrile, tetrahydrofuran, acetic acid, N,N-dimethylformamide, or a mixture thereof.

Additionally, in case that the above-mentioned alkylating agent or base to be used in the reaction are liquid, they can also be used as a solvent.

The reaction temperature of this reaction is not critical and the reaction is usually carried out under cooling to warming.

Process 6

The object compound (Ii) or a salt thereof can be prepared by reacting a compound (Ig) or a salt thereof with an acylating agent.

Suitable salts of the compounds (Ig) and (Ii) may be the same as those exemplified above with regard to the compound (I).

This reaction is carried out in accordance with a conventional method using a conventional acylating agent.

Suitable acylating agent includes an organic acid represented by the formula: R'—OH wherein R' is acyl or substituted acyl as illustrated above, or its reactive derivative.

Suitable organic acid derivative includes conventional ones such as acid halides (e.g. acid chlorides, acid bromides), acid azides, acid anhydrides, activated amides and activated esters.

In case that acylating agent is used in a free acid form or its salt form, the acylation may preferably be carried out in the presence of a conventional condensing agent as explained in Process 1.

The reaction is usually carried out in a conventional solvent which does not adversely influence the reaction, such as water, acetone, dioxane, chloroform, methylene chloride, acetonitrile, ethylene chloride, tetrahydrofuran, acetic acid, N,N-dimethylform-amide, pyridine, or a mixture thereof.

Additionally, the reaction may preferably be carried out in the presence of a conventional base such as triethylamine, pyridine and sodium hydroxide.

The reaction temperature of this reaction is not critical and the reaction is usually carried out under cooling to warming.

Process 7

The object compound (Ik) or a salt thereof can be prepared by subjecting a compound (Ij) or a salt thereof to elimination reaction of the hydroxy-protective group in $A^8$.

Suitable salts of the compounds (Ij) and (Ik) may be the same as those exemplified above with regard to the compound (I).

This reaction can be carried out in substantially the same manner as in Process 2, and therefore, the reaction mode and reaction conditions (e.g. base, acid, catalyst, solvent, reaction temperature) of this reaction are to be referred to those explained in Process 2.

Processes 8, 9

The object compound (Im) or a salt thereof can be prepared by subjecting a compound (Il) or a salt thereof to oxidation of S atom in $B^5$. The object compound (In) or a salt thereof can be prepared by subjecting a compound (Im) or a salt thereof to oxidation of S atom in $B^6$.

Suitable salts of the compounds (Il), (Im) and (In) may be the same as those exemplified above with regard to the compound (I).

This reaction is carried out in accordance with a conventional method using an oxidizing agent.

Suitable oxidizing agent includes hydrogen peroxide, Jones reagent, peracids (e.g. peracetic acid, perbenzoic acid, m-chloroperbenzoic acid), chromic acid, potassium permanganate, and alkali metal periodates (e.g. sodium periodate).

The reaction is usually carried out in a conventional solvent which does not adversely influence the reaction, such as water, organic acid (e.g. acetic acid, trifluoroacetic acid), acetone, ethyl acetate, alcohol (e.g. methanol, ethanol), dichloromethane, chloroform, or a mixture thereof.

The reaction temperature of this reaction is not critical and the reaction is usually carried out under cooling to warming.

The compounds obtained by the above processes can be isolated and purified by a conventional method such as pulverization, recrystallization, column chromatography, reprecipitation or the like.

The object compound (I) thus obtained can be converted to a pharmaceutically acceptable salt in a conventional manner.

It is to be noted that the object compound (I) may include one or more stereoisomer(s) such as optical isomer(s) and geometrical isomer(s) due to asymmetric carbon atom(s) or double bond(s), and all such isomers and mixtures thereof are included within the scope of this invention.

The object compound (I) and pharmaceutically acceptable salts of the present invention exhibit activities such as vasopressin antagonistic activity, vasodilating activity, hypotensive activity, activity of inhibiting saccharide release in liver, activity of inhibiting growth of mesangium cells, diuretic activity, platelet aggregation inhibitory activity, oxytocin antagonistic activity, antidepressant activity, anti-anxiety activity and the like, and are useful for the treatment and/or prophylaxis of hypertension, heart failure, renal insufficiency, edema, ascites, vasopressin parasecretion syndrome, hepatocirrhosis, hyponatremia, hypokalemia, diabetes mellitus, circulation disorder, cerebrovascular disease (e.g. cerebral edema, cerebral infarction, etc.), Meniere's syndrome (e.g. Meniere's disease, etc.), motion sickness, depressant, anxiety and the like in human beings and animals.

In order to illustrate the usefulness of the object compound (I), the pharmacological data of the compound (I) are shown in the following.

Test 1

Vasopressin 1 (VI) Receptor Binding (i) Test Method

Blood was obtained from normal subject by venipuncture. Platelet-rich plasma (PRP) was prepared by centrifugation of whole blood at 200×g for 10 minutes. PRP was centrifuged at 45,000×g for 30 minutes. The remaining pellet was resuspended in 10 volume of ice-cold 100 mM Tris-HCl buffer (pH 7.4, containing 5 mM $MgCl_2$, 0.1% bovine serum albumin and 1 mM EDTA), and again centrifuged at 45,000×g for 30 minutes. The final pellet was resuspended in 100 mM Tris-HCl buffer. The resulting suspension was used immediately for the binding assay.

Competition assays were conducted at equilibrium (15 minutes at 30° C.) by using 1.5 nM $^3$H-vasopressin (40–87 Ci/mmol; New England Nuclear) in 100 mM Tris-HCl buffer (pH 7.4). Nonspecific binding was determined by using 1 μM vasopressin. After incubation, the reaction was terminated by adding 5 ml of ice-cold 100 mM Tris-HCl buffer (pH 7.4), and then filtered immediately through Whatman glass filter (GF/C). The filter was washed twice with the same buffer. The glass filter was placed in a liquid scintillation cocktail, and the radioactivity thereof was counted by using a liquid scintillation counter. Competition activity of the test compound was represented by $IC_{50}$ values.

(ii) Test Result

| Test Compound | $IC_{50}$ (nM) | |
|---|---|---|
| (Example No.) | human | rat |
| 2 | 0.41 | 2.1 |
| 50 | 0.55 | 1.8 |
| 55 | 0.7 | 1.7 |
| 73 | 0.5 | 2.2 |
| 76 | 0.08 | 0.2 |

Test 2

Vasopressin 2 (V2) Receptor Binding (i) Test Method

For binding assays, a receptor cDNA was permanently expressed in Chinese hamster ovary (CHO) cells. A vector directing expression of the cDNA of a human V2 receptor was transfected into the CHO cells, and the clonal cell lines expressing the human V2 receptor were established essentially as described previously (Nakajima, Y., et. al. J. Biol. chem., 267, 2437, 1992).

DNA-transfected cells were harvested and homogenized in ice-cold 250 nm Tris-HCl (pH 7.4), 10 mM $MgCl_2$, 1 mM EDTA and 5 μg/ml p-amidinophenylmethylsulfonyl fluoride (A-PMSF). The homogenate was centrifuged at 500×g for 10 minutes. The supernatant was centrifuged at 100,00×g for 1 hour. The final pellet was suspended in 25 mM Tris-HCl buffer (pH 7.4, containing 10 mM $MgCl_2$, 1 mM EDTA and 5 μg/ml A-PMSF), and stored in small aliquots at −80° C.

Competition assays were conducted at equilibrium (2 hours at 22° C.) by using 0.5 nm $^3$H-vasopressin (40–87 Ci/mmol; New England Nuclear) in 100 mM Tris-HCl buffer (pH 7.4, containing 5 mM $MgCl_2$, 5 μg/ml A-PMSF, 4 μg/ml leupeptin, 40 μg/ml bacitracin, 20 μg/ml chymostatin and 0.1% bovine serum albimin). Nonspecific binding was determined by using 1 μM vasopressin. After incubation, the reaction mixture was immediately filtered through Whatman glass filter (GF/C). The filter was washed twice with the same buffer. The radioactivity was counted by using a liquid scintillation counter. Competition activity of the test compound was represented by $IC_{50}$ values.

(ii) Test Result

| Test Compound (Example No.) | $IC_{50}$ (nM) human |
|---|---|
| 2 | 241 |
| 50 | 69 |
| 55 | 104 |
| 73 | 159 |
| 76 | 140 |

For therapeutic purposes, the compound (I) or pharmaceutically acceptable salts threrof of the present invention can be used in the form of pharmaceutical preparation containing compound (I) or pharmaceutical acceptable salts threrof, as an active ingredient, in admixture with a pharmaceutically acceptable carrier such as an organic or inorganic solid, semi-solid or liquid excipient suitable for oral, parenteral or external (topical) administration. The pharmaceutical preparation may be in the form of capsules, tablets, dragees, granules, suppositories, solution, lotion, suspension, emulsion, ointment, gel, or the like. If desired, there may be included, in these preparations, auxiliary substances, stabilizing agent, wetting or emulsifying agent, buffer and other commonly used additives.

While the dosage of the compound (I) or pharmaceutically acceptable salts threrof will vary depending upon the age and condition of patients, an average single dose of about 0.1 mg, 1 mg, 10 mg, 50 mg, 100 mg, 250 mg, 500 mg or 1000 mg of the compound (I) may be effective for treating the above-mentioned diseases. In general, amounts between 0.1 mg/body and about 1,000 mg/body may be administered per day.

The following Preparations and Examples are given for the purpose of illustrating this invention.

PREPARATION 1

To a solution of 3-methoxy-4-methoxycarbonylbenzoic acid (286 mg) in dichloromethane (10 ml) were added oxalyl chloride (0.145 ml) and a drop of N,N-dimethylformamide, and the solution was stirred at room temperature for 1 hour. The solvent was evaporated in vacuo to give an acid chloride as an oil. To an ice-bath-cooled mixture of 2,3,4,5-tetrahydro-1H-1-benzazepine (200 mg) and triethylamine (0.284 ml) in dichloromethane (10 ml) was added dropwise a solution of the above acid chloride in dichloromethane (3 ml), and the mixture was stirred at room temperature for 2 hours. The solution was washed successively with water, 1N hydrochloric acid and brine and the organic solution was dried over magnesium sulfate. The solvent was evaporated in vacuo and the residue was solidified with ether to give methyl 2-methoxy-4-(2,3,4,5-tetrahydro-1H-1-benzazepin-1-yl)carbonylbenzoate (453 mg). $^1$H-NMR (300 MHz, CDCl$_3$, δ):

1.54(m, 1H), 1.91–2.28(m, 3H), 2.73–2.94(m, 2H), 3.03 (m, 1H), 3.69(s, 3H), 3.82(s, 3H), 5.00(m, 1H), 6.62(d, J=8 Hz, 1H), 6.75(d, J=8 Hz, 1H), 6.81(s, 1H), 6.91(t, J=8 Hz, 1H), 7.08(t, J=8 Hz, 1H), 7.21(d, J=8 Hz, 1H), 7.56(d, J=8 Hz, 1H).

PREPARATION 2

A solution of methyl 2-methoxy-4-(2,3,4,5-tetrahydro-1H-1-benzazepin-1-yl)carbonylbenzoate (450 mg) in a mixture of methanol (15 ml) and 1 N aqueous sodium hydroxide (3 ml) was stirred at 60° C. for 2 hours and the solution was cooled to room temperature. The solution was adjusted to pH 2–3 with 1N hydrochloric acid and extracted with chloroform. The organic layer was washed with water and brine and dried over magnesium sulfate. The solvent was evaporated in vacuo and the residue was solidified with ether to give 2-methoxy-4-(2,3,4,5-tetrahydro-1H-1-benzazepin-1-yl)carbonylbenzoic acid (410 mg).

$^1$H-NMR (300 MHz, CDCl$_3$, δ): 1.55(m, 1H), 1.93–2.19 (m, 3H), 2.78–3.08(m, 3H), 3.90(s, 3H), 4.99(m, 1H), 6.61 (d, J=8 Hz, 1H), 6.80(d, J=8 Hz, 1H), 6.93(t, J=8 Hz, 1H), 7.00(s, 1H), 7.11(t, J=8 Hz, 1H), 7.24(d, J=8 Hz, 1H), 7.89(d, J=8 Hz, 1H).

EXAMPLE 1

A mixture of 2-methoxy-4-(2,3,4,5-tetrahydro-1H-1-benzazepin-1-yl)-carbonylbenzoic acid (200 mg), 4-amino-1-tert-butoxycarbonyl-2-methyl-1H-benzimidazole (152 mg), WSCD·HCl [water soluble carbodiimide, 1-ethyl-3-(3-dimethylaminopropyl)carbodiimide hydrochloride, 141 mg] and 1-hydroxybenzotiazole (100 mg) in N,N-dimethylformamide (5 ml) was stirred at room temperature overnight, and the mixture was diluted with ethyl acetate. The solution was washed successively with saturated aqueous sodium hydrogencarbonate solution, water, and brine and dried over magnesium sulfate. The solvent was evaporated and the residue was purified by silica gel column chromatography using chloroform as an eluent to give 2-methoxy-N-[2-methyl-1-(tert-butoxycarbonyl)-1H-benzimidazol-4-yl]-4-(2,3,4,5-tetrahydro-1H-1-benzazepin-1-yl)-carbonylbenzamide (185 mg).

$^1$H-NMR (300 MHz, CDCl$_3$, δ): 1.57(m, 1H), 1.72(s, 9H), 1.92–2.18(m, 3H), 2.77–3.13(m, 3H), 2.80(s, 3H), 3.98(s, 3H), 5.01(m, 1H), 6.65(d, J=8 Hz, 1H), 6.84(d, J=8 Hz, 1H), 6.91(t, J=8 Hz, 1H), 6.98(s, 1H), 7.10(t, J=8 Hz, 1H), 7.20–7.30(m, 2H), 7.57(d, J=8 Hz, 1H), 8.05(d, J=8 Hz, 1H), 8.40(d, J=8 Hz, 1H).

EXAMPLE 2

A solution of 2-methoxy-N-[2-methyl-1-(tert-butoxycarbonyl)-1H-1-benzimidazol-4-yl]-4-(2,3,4,5-tetrahydro-1H-benzazepin-1-yl)carbonylbenzamide (175 mg) in 90% aqueous trifluoroacetic acid (5 ml) was stirred at room temperature for 1 hour and the solvent was evaporated in vacuo. The residue was dissolved in chloroform and the solution was washed successively with saturated aqueous sodium hydrogencarbonate solution, water and brine. The solution was dried over magnesium sulfate and the solvent was evaporated in vacuo. The residue was solidified with ether to give 2-methoxy-N-(2-methyl-1H-benzimidazol-4-yl)-4-(2,3,4,5-tetrahydro-1H-1-benzazepin-1-yl)-carbonylbenzamide (90 mg).

$^1$H-NMR (300 MHz, CDCl$_3$, δ): 1.54(m, 1H), 1.90–2.20 (m, 3H), 2.61(s, 3H), 2.75–3.11(m, 3H), 3.91(s, 3H), 5.02 (m, 1H), 6.65(d, J=8 Hz, 1H), 6.86(d, J=8 Hz, 1H), 6.94(t, J=8 Hz, 1H), 6.98(s, 1H), 7.07–7.18(m, 2H), 7.20–7.27(m, 2H), 8.03(d, J=8 Hz, 1H).

PREPARATION 3

Methyl 2-methoxy-4-(2,3,4,5-tetrahydro-4-oxo-1H-1,5-benzodiazepin-1-yl)carbonylbenzoate was obtained in substantially the same manner as in Preparation 1.

$^1$H-NMR (300 MHz, CDCl$_3$, δ): 2.59–2.93(m, 2H), 3.72 (s, 3H), 3.83(s, 3H), 3.87(m, 1H), 4.87(m, 1H), 6.71–6.77 (m, 2H), 6.86(s, 1H), 6.90(t, J=8 Hz, 1H), 7.12(d, J=8 Hz, 1H), 7.21(d, J=8 Hz, 1H), 7.53(d, J=8 Hz, 1H), 8.41 (br, 1H).

PREPARATION 4

2-Methoxy-4-(2,3,4,5-tetrahydro-4-oxo-1H-1,5-benzodiazepin-1-yl)carbonylbenzoic acid was obtained in substantially the same manner as in Preparation 2.

1H-NMR (300 MHz, CDCl$_3$, δ): 2.60–2.94(m, 2H), 3.87 (m, 1H), 3.90(s, 3H), 4.89(m, 1H), 6.75(d, J=8 Hz, 1H), 6.80(d, J=8 Hz, 1H), 6.92(t, J=8 Hz, 1H), 7.00(s, 1H), 7.15(d, J=8 Hz, 1H), 7.24(t, J=8 Hz, 1H), 7.87(d, J=8 Hz, 1H), 8.83 (br, 1H).

EXAMPLE 3

2-Methoxy-N-[2-methyl-1-(tert-butoxycarbonyl)-1H-benzimidazol-4-yl]-4-(2,3,4,5-tetrahydro-4-oxo-1H-1,5-benzodiazepin-1-yl)carbonylbenzamide was obtained in substantially the same manner as in Example 1.

$^1$H-NMR (300 MHz, CDCl$_3$, δ): 1.70(s, 9H), 2.61–2.95 (m, 2H), 2.82(s, 3H), 3.90(m, 1H), 4.03(s, 3H), 4.90(m, 1H), 6.78(d, J=8 Hz, 1H), 6.83(d, J=8 Hz, 1H), 6.90(t, J=8 Hz, 1H), 7.02(s, 1H), 7.13(d, J=8 Hz, 1H), 7.20–7.31(m, 2H), 7.57(d, J=8 Hz, 1H), 8.07(d, J=8 Hz, 1H), 8.38 (br, 1H), 8.40(d, J=8 Hz, 1H).

EXAMPLE 4

2-Methoxy-N-(2-methyl-1H-benzimidazol-4-yl)-4-(2,3,4,5-tetrahydro-4-oxo-1H-1,5-benzodiazepin-1-yl) carbonylbenzamide was obtained in substantially the same manner as in Example 2.

$^1$H-NMR (300 MHz, CDCl$_3$, δ): 2.60(s, 3H), 2.63–2.94 (m, 2H), 3.88(m, 1H), 3.91(s, 3H), 4.90(m, 1H), 6.73–6.81 (m, 2H), 6.91(d, J=8 Hz, 1H), 6.97(s, 1H), 7.10–7.19(m, 3H), 7.20–7.26(m, 2H), 7.97(d, J=8 Hz, 1H), 8.66 (br, 1H).

PREPARATION 5

Methyl 2-methoxy-4-(2,3,4,5-tetrahydro-5-oxo-1H-1-benzazepin-1-yl)carbonylbenzoate was obtained in substantially the same manner as in Preparation 1.

$^1$H-NMR (300 MHz, CDCl$_3$, δ): 2.15(br, 4H), 3.85–3.91 (m, 2H), 3.69(s, 3H), 3.82(s, 3H), 6.68–6.82(m, 3H), 7.19–7.32(m, 2H), 7.57(d, J=8 Hz, 1H), 7.80(t, J=8 Hz, 1H).

PREPARATION 6

2-Methoxy-4-(2,3,4,5-tetrahydro-5-oxo-1H-1-benzazepin-1-yl)carbonylbenzoic acid was obtained in substantially the same manner as in Preparation 2.

$^1$H-NMR (300 MHz, CDCl$_3$, δ): 2.0–2.4 (br, 4H), 2.87(t, J=7.5 Hz, 2H), 3.86(s, 3H), 6.71(d, J=8 Hz, 1H), 6.83(s, 1H), 6.93(d, J=8 Hz, 1H), 7.20–7.35(m, 2H), 7.79(d, J=8 Hz, 1H), 7.97(d, J=8 Hz, 1H).

EXAMPLE 5

2-Methoxy-N-(2-methyl-1H-benzimidazol-4-yl)-4-(2,3,4,5-tetrahydro-5-oxo-1H-1-benzazepin-1-yl) carbonylbenzamide was obtained in substantially the same manner as in Example 1.

$^1$H-NMR (300 MHz, CDCl$_3$, δ): 1.9–2.4(br, 4H), 2.59(s, 3H), 2.90(t, J=7.5 Hz, 2H), 3.90(s, 3H), 6.73(d, J=8 Hz, 1H), 6.84(s, 1H), 6.98(d, J=8 Hz, 1H), 7.14(t, J=8 Hz, 1H), 7.20–7.33(m, 3H), 7.50 (br, 1H), 7.81(d, J=8 Hz, 1H), 8.10(d, J=8 Hz, 1H).

EXAMPLE 6

To an ice-bath-cooled solution of 2-methoxy-N-(2-methyl-1H-benzimidazol-4-yl) -4-(2,3,4,5-tetrahydro-5-oxo-1H-1-benzazepin-1-yl)carbonylbenzamide (123 mg) in methanol (5 ml) was added sodium borohydride (10 mg), and the mixture was stirred at the same temperature for 1 hour. The reaction mixture was diluted with chloroform and the solution was washed with water and brine. The solution was dried over magnesium sulfate and the solvent was evaporated in vacuo. The residue was triturated with ether to give 2-methoxy-N-(2-methyl-1H-benzimidazol-4-yl)-4-(2,3,4,5-tetrahydro-5-hydroxy-1H-1-benzazepin-1-yl) carbonylbenzamide (123 mg).

$^1$H-NMR (300 MHz, CDCl$_3$, δ): 1.$^6$0–1.96(m, 2H), 2.12 (m, 1H), 2.29(m, 1H), 2.51(s, 3H×⅓), 2.53(s, 3H×⅔), 2.88(m, 1H), 3.69(s, 3H×⅓), 3.81(s, 3H×⅔), 4.80–5.18(m, 2H), 6.58–6.62(m, 2H), 6.77(d, J=8 Hz, 1H), 6.90(s, 1H), 6.93–7.90(m, 5H), 7.72(d, J=8 Hz, 1H), 7.91(d, J=8 Hz, 1H), 8.03(d, J=8 Hz, 1H).

PREPARATION 7

Methyl 2-methoxy-4-(2,3,4,5-tetrahydro-5-oxo-1H-1,4-benzodiazepin-1-yl)carbonylbenzoate was obtained in substantially the same manner as in Preparation 1.

$^1$H-NMR (300 MHz, CDCl$_3$, δ): 3.93.(s, 3H), 4.02(s, 3H), 4.20(t, J=9 Hz, 2H), 4.45(t, J=9 Hz, 2H), 7.04(t, J=8 Hz, 1H), 7.54(t, J=8 Hz, 1H), 7.69(d, J=8 Hz, 1H), 7.77(s, 1H), 7.89–7.96(m, 2H), 8.97(d, J=8 Hz, 1H).

PREPARATION 8

2-Methoxy-4-(2,3,4,5-tetrahydro-5-oxo-1H-1,4-benzodiazepin-1-yl)carbonylbenzoic acid was obtained in substantially the same manner as in Preparation 2.

$^1$H-NMR (300 MHz, CDCl$_3$, δ): 4.15(s, 3H), 4.20(t, J=9 Hz, 2H), 4.44(t, J=9 Hz, 2H), 7.18(t, J=8 Hz, 1H), 7.54(t, J=8 Hz, 1H), 7.80(d, J=8 Hz, 1H), 7.83(s, 1H), 7.92(d, J=8 Hz, 1H), 8.25(d, J=8 Hz, 1H), 8.91(d, J=8 Hz, 1H).

EXAMPLE 7

2-Methoxy-N-(2-methyl-1H-benzimidazol-4-yl)-4-(2,3,4,5-tetrahydro-5-oxo-1H-1,4-benzodiazepin-1-yl) carbonylbenzamide was obtained in substantially the same manner as in Example 1.

$^1$H-NMR (300 MHz, CDCl$_3$, δ): 2.65(s, 3H), 4.21(t, J=9 Hz, 2H), 4.23(s, 3H), 4.48(t, J=9 Hz, 2H), 7.11–7.23(m, 2H), 7.56(t, J=8 Hz, 1H), 7.79–7.86(m, 2H), 7.92(d, J=8 Hz, 1H), 8.40(d, J=8 Hz, 1H), 8.92(d, J=8 Hz, 1H).

EXAMPLE 8

2-Methoxy-N-(2-phthaloylaminomethyl-1H-benzimidazol-4-yl)-4-(2,3,4,5-tetrahydro-1H-1-benzazepin-1-yl)carbonylbenzamide was obtained in substantially the same manner as in Example 1.

$^1$H-NMR (300 MHz, CDCl$_3$, δ): 1.57(m, 1H), 1.91–2.19 (m, 3H), 2.79–2.99(m, 2H), 3.10(m, 1H), 4.00(s, 3H), 5.02 (m, 1H), 5.11(s, 2H), 6.65(d, J=8 Hz, 1H), 6.80–6.99(m, 3H), 7.10(m, 1H), 7.18–7.25(m, 2H), 7.66–7.78(m, 2H), 7.85–7.91(m, 2H), 8.00(s, 1H), 8.06(d, J=8 Hz, 1H), 8.21(d, J=8 Hz, 1H).

EXAMPLE 9

A mixture of 2-methoxy-N-(2-phthaloylaminomethyl-1H-benzimidazol-4-yl)-4-(2,3,4,5-tetrahydro-1H-1-benzazepin-1-yl)carbonylbenzamide (530 mg) and hydrazine hydrate (221 mg) in ethanol (15 ml) was stirred at room temperature overnight. After removing insoluble material by filtration, the solvent was evaporated in vacuo and the residue was subjected to silica gel column chromatography (1% methanol in chloroform). The objective fraction was evaporated in vacuo to give N-(2-aminomethyl-1H-benzimidazol-4-yl)-2-methoxy-4-(2,3,4,5-tetrahydro-1H-1-benzazepin-1-yl)carbonylbenzamide (370 mg).

$^1$H-NMR (300 MHz, CDCl$_3$, δ): 1.54(m, 1H), 1.91–2.18 (m, 3H), 2.75–2.97(m, 2H), 3.05(m, 1H), 3.91(s, 3H), 4.17 (s, 2H), 5.01 (m, 1H), 6.67(d, J=8 Hz, 1H), 6.85(d, J=8 Hz, 1H), 6.92–6.66(m, 2H), 7.04–7.35(m, 5H), 8.03(d, J=8 Hz, 1H).

EXAMPLE 10

N-(2-Aminomethyl-1H-benzimidazol-4-yl)-2-methoxy-4-(2,3,4,5-tetrahydro-1H-1-benzazepin-1-yl) carbonylbenzamide (150 mg) was dissolved in a mixture of 1N hydrochloric acid (0.7 ml) and water (5 ml), and the solution was lyophilized to give N-(2-aminomethyl-1H-benzimidazol-4-yl)-2-methoxy-4-(2,3,4,5-tetrahydro-1H-1-benzazepin-1-yl)carbonylbenzamide dihydrochloride (132 mg).

$^1$H-NMR (300 MHz, DMSO-$d_6$, δ): 1.42(m, 1H), 1.82–1.97(m, 2H), 2.07(m, 1H), 2.72(m, 1H), 2.90(m, 1H), 3.08(m, 1H), 3.90(s, 3H), 4.39(s, 2H), 4.83(m, 1H), 6.81(d, J=8 Hz, 1H), 6.90–7.00(m, 3H), 7.11(t, J=8 Hz, 1H), 7.22–7.40(m, 4H), 7.83(d, J=8 Hz, 1H), 8.00(d, J=8 Hz, 1H), 8.83(br, 2H).

EXAMPLE 11

A mixture of N-(2-aminomethyl-1H-benzimidazol-4-yl)-2-methoxy-4-(2,3,4,5-tetrahydro-1H-1-benzazepin-1-yl)carbonylbenzamide (190 mg), 37% formaldehyde solution (122 mg) and sodium cyanoborohydride (50.8 mg) in methanol (15 ml) was stirred at room temperature for 6 hours. The mixture was diluted with chloroform and the solution was washed with saturated aqueous sodium hydrogencarbonate solution and brine. The organic layer was dried over magnesium sulfate and the solvent was evaporated in vacuo. The crude product was purified by silica gel column chromatography (1% methanol in chloroform) to give N-(2-dimethylaminomethyl-1H-benzimidazol-4-yl)-2-methoxy-4-(2,3,4,5-tetrahydro-1H-1-benzazepin-1-yl) carbonylbenzamide (68 mg).

$^1$H-NMR (300 MHz, CDCl$_3$, δ): 1.53(m, 1H), 1.90–2.19(m, 3H), 2.32(s, 6H), 2.73–3.13(m, 3H), 3.76(s, 3H), 3.97(br, 2H), 5.02(m, 1H), 6.63(d, J=8 Hz, 1H), 6.75–7.34(m, 8H), 8.06(d, J=8 Hz, 1H).

EXAMPLE 12

N-(2-Dimethylaminomethyl-1H-benzimidazol-4-yl)-2-methoxy-4-(2,3,4,5-tetrahydro-1H-1-benzazepin-1-yl)carbonylbenzamide dihydrochloride was obtained in substantially the same manner as in Example 10.

$^1$H-NMR (300 MHz, DMSO-$d_6$, δ): 1.44(m, 1H), 1.81–1.96(m, 2H), 2.07(m, 1H), 2.75(m, 1H), 2.86–3.18(m, 2H), 2.98(s, 6H), 3.92(s, 3H), 4.61(s, 2H), 4.86(m, 1H), 6.81(d, J=8 Hz, 1H), 6.88–7.00(m, 2H), 7.04(s, 1H), 7.01(t, J=8 Hz, 1H), 7.21–7.37(m, 3H), 7.87(d, J=8 Hz, 1H), 8.09(d, J=8 Hz, 1H).

EXAMPLE 13

To an ice-bath-cooled solution of N-(2-aminomethyl-1H-benzimidazol-4-yl)-2-methoxy-4-(2,3,4,5-tetrahydro-1H-1-benzazepin-1-yl)carbonylbenzamide (100 mg) in pyridine (5 ml) was added methanesulfonyl chloride (24.4 mg) and the solution was stirred at room temperature for 4 hours. After removing the solvent by evaporation, the product was purified by silica gel column chromatography (chloroform) to give a syrup and the syrup was solidified with ether to give 2-methoxy-N-(2-methanesulfonylaminomethyl-1H-benzimidazol-4-yl)-4-(2,3,4,5-tetrahydro-1H-1-benzazepin-1-yl)carbonylbenzamide (98 mg).

$^1$H-NMR (300 MHz, CDCl$_3$, δ):
1.52(m, 1H), 1.90–2.17(m, 3H), 2.75–3.10(m, 3H), 2.99(s, 3H), 3.82(m, 3H), 4.51(m, 2H), 5.00(m, 1H), 5.93(br, 1H), 6.62(d, J=8 Hz, 1H), 6.82(d, J=8 Hz, 1H), 6.83(s, 1H), 6.90(t, J=8 Hz, 1H), 7.08–7.29(m, 5H), 7.991(d, J=8 Hz, 1H).

PREPARATION 9

Methyl 2-methoxy-4-(2,3,4,5-tetrahydro-7-methyl-1H-1-benzazepin-1-yl)carbonylbenzoate was obtained in substantially the same manner as in Preparation 1.

$^1$H-NMR (300 MHz, CDCl$_3$, δ):
1.51(m, 1H), 1.90–2.15(m, 2H), 2.24(s, 3H), 2.70–2.85(m, 2H), 2.96(m, 1H), 3.69(s, 3H), 3.82(s, 3H), 4.98(m, 1H), 6.50(d, J=8 Hz, 1H), 6.70(d, J=8 Hz, 1H), 6.76(d, J=8 Hz, 1H), 6.81(s, 1H), 7.00(s, 1H), 7.56(d, J=8 Hz, 1H).

PREPARATION 10

2-Methoxy-4-(2,3,4,5-tetrahydro-7-methyl-1H-1-benzazepin-1-yl)carbonylbenzoic acid was obtained in substantially the same manner as in Preparation 2.

$^1$H-NMR (300 MHz, CDCl$_3$, δ): 1.51(m, 1H), 1.90–2.01(m, 2H), 2.10(m, 1H), 2.23(s, 3H), 2.72–2.87(m, 2H), 2.98(m, 1H), 3.90(s, 3H), 4.95(m, 1H), 6.47(d, J=8 Hz, 1H), 6.70(d, J=8 Hz, 1H), 6.77(d, J=8 Hz, 1H), 6.99–7.04(m, 2H), 7.89(d, J=8 Hz, 1H).

EXAMPLE 14

2-Methoxy-N-(2-methyl-1H-benzimidazol-4-yl)-4-(2,3,4,5-tetrahydro-7-methyl-1H-1-benzazepin-1-yl)carbonylbenzamide was obtained in substantially the same manner as in Example 1.

$^1$H-NMR (300 MHz, CDCl$_3$, δ): 1.52(m, 1H), 1.90–2.05(m, 2H), 2.10(m, 1H), 2.26(s, 3H), 2.60(s, 3H), 2.72–2.90(m, 2H), 2.01(m, 1H), 3.94(s, 3H), 5.00(m, 1H), 6.51(d, J=8 Hz, 1H), 6.68–6.76(m, 2H), 6.84(d, J=8 Hz, 1H), 6.93–7.21(m, 4H), 8.03(d, J=8 Hz, 1H).

EXAMPLE 15

2-Methoxy-N-(2-methyl-1H-benzimidazol-4-yl)-4-(2,3,4,5-tetrahydro-7-methyl-1H-1-benzazepin-1-yl)carbonylbenzamide hydrochloride was obtained in substantially the same manner as in Example 10.

$^1$H-NMR (300 MHz, DMSO-$d_6$, δ): 1.40(m, 1H), 1.80–1.93(m, 2H), 2.01(m, 1H), 2.24(s, 3H), 2.68(m, 1H), 2.78(s, 3H), 2.81(m, 1H), 3.02(m, 1H), 3.78(s, 3H), 4.83(m, 1H), 6.72(d, J=8 Hz, 1H), 6.80(d, J=8 Hz, 1H), 6.87(d, J=8 Hz, 1H), 7.00(s, 1H), 7.11(s, 1H), 7.47(t, J=8 Hz, 1H), 7.52–7.68(m, 3H).

EXAMPLE 16

2-Methoxy-N-(2-methylbenzoxazol-4-yl)-4-(2,3,4,5-tetrahydro-1H-1-benzazepin-1-yl)carbonylbenzamide was obtained in substantially the same manner as in Example 1.

$^1$H-NMR (300 MHz, CDCl$_3$, δ): 1.53(m, 1H), 1.91–2.19(m, 3H), 2.62(s, 3H), 2.73–2.97(m, 2H), 3.08(m, 1H), 3.97(s, 3H), 5.02(m, 1H), 6.65(d, J=8 Hz, 1H), 6.82(d, J=8 Hz, 1H), 6.9s(t, J=8 Hz, 1H), 6.98(s, 1H), 7.10(t, J=8 Hz, 1H), 7.15–7.30(m, 3H), 8.03(d, J=8 Hz, 1H), 8.37(d, J=8 Hz, 1H).

PREPARATION 11

To an ice-bath-cooled solution of methyl 2-methoxy-4-(2,3,4,5-tetrahydro-1H-1-benzazepin-1-yl)carbonylbenzoate (350 mg) in tetrahydrofuran (15 ml) was added dropwise a 1M solution of borane-tetrahydrofuran complex (3.1 ml), and the mixture was stirred at room temperature for 6 hours. After quenching the reaction with 1N hydrochloric acid (10 ml), the mixture was adjusted to pH 8–9 with concentrated ammonia solution and extracted with chloroform. The solution was washed with brine. The organic layer was dried over magnesium sulfate and the solvent was evaporated in vacuo. The crude product was purified by silica gel column chromatography (10% ethyl acetate in hexane) to give methyl 2-methoxy-4-(2,3,4,5-tetrahydro-1H-1-benzazepin-1-yl)methylbenzoate (255 mg).

¹H-NMR (300 MHz, CDCl₃, δ): 1.60–1.69(m, 4H), 2.82–2.91(m, 4H), 3.87(s, 3H), 3.89(s, 3H), 4.32(s, 2H), 6.87–6.98(m, 2H), 7.02(d, J=8 Hz, 1H), 7.10–7.18(m, 3H), 7.80(d, J=8 Hz, 1H).

PREPARATION 12

2-Methoxy-4-(2,3,4,5-tetrahydro-1H-1-benzazepin-1-yl)methylbenzoic acid was obtained in substantially the same manner as in Preparation 2.

¹H-NMR (300 MHz, CDCl₃, δ): 1.60–1.70(m, 4H), 2.83–2.90(m, 4H), 4.06(s, 3H), 4.38(s, 2H), 6.87–6.95(m, 2H), 7.10–7.22(m, 4H), 8.13(d, J=8 Hz, 1H).

EXAMPLE 17

2-Methoxy-N-(2-methyl-1H-benzimidazol-4-yl)-4-(2,3,4,5-tetrahydro-1H-1-benzazepin-1-yl)methylbenzamide was obtained in substantially the same manner as in Example 1.

¹H-NMR (300 MHz, CDCl₃, δ): 1.60–1.70(m, 4H), 2.63 (s, 3H), 2.86–2.94(m, 4H), 4.08(s, 3H), 4.38(s, 2H), 6.87–7.00(m, 3H), 7.10–7.26(m, 7H), 8.26(d, J=8 Hz, 1H).

EXAMPLE 18

2-Methoxy-N-(2-methyl-1H-benzimidazol-4-yl)-4-(2,3,4,5-tetrahydro-1H-1-benzazepin-1-yl)methylbenzamide dihydrochloride was obtained in substantially the same manner as in Example 10. ¹H-NMR (300 MHz, DMSO-d₆, δ): 1.42–1.80(m, 4H), 2.61–3.04(m, 4H), 2.80(s, 3H), 3.92 (s, 3H), 4.48(br, 2H), 7.04–7.27(m, 5H), 7.43–7.81(m, 6H).

EXAMPLE 19

2-Methoxy-N-[2-(morpholin-4-yl)methyl-1H-benzimidazol-4-yl]-4-(2,3,4,5-tetrahydro-1H-1-benzazepin-1-yl)carbonylbenzamide was obtained in substantially the same manner as in Example 1.

¹H-NMR (300 MHz, CDCl₃, δ): 1.53(m, 1H), 1.92–2.19 (m, 3H), 2.59(t, J=7 Hz, 4H), 2.72–3.12(m, 3H), 3.76(t, J=7 Hz, 4H), 3.81(s, 2H), 3.90–4.00(m, 3H), 5.02(m, 1H), 6.64(m, 1H), 6.77–7.03(m, 4H), 7.04–7.26(m, 3H), 8.08(m, 1H), 8.32(m, 1H).

EXAMPLE 20

2-Methoxy-N-[2-(morpholin-4-yl)methyl-1H-benzimidazol-4-yl)-4-(2,3,4,5-tetrahydro-1H-1-benzazepin-1-yl)rcarbonylbenzamide dihydrochloride was obtained in substantially the same manner as in Example 10.

¹H-NMR (300 MHz, DMSO-d₆, δ): 1.41(m, 1H), 1.82–1.95(m, 2H), 2.03(m, 1H), 2.73(m, 1H), 2.90(m, 1H), 3.08(m, 1H), 3.31–3.46(m, 2H), 3.79–3.90(m, 2H), 3.91(s, 3H), 4.64(s, 2H), 4.85(m, 1H), 6.80(d, J=8 Hz, 1H), 6.90(d, J=8 Hz, 1H), 6.97(t, J=8 Hz, 1H), 7.02(s, 1H), 7.10(t, J=8 Hz, 1H), 7.19–7.40(m, 3H), 7.84(d, J=8 Hz, 1H), 8.07(d, 1H).

PREPARATION 13

To a solution of methyltriphenylphosphonium bromide (607 mg) in N,N-dimethylformamide (10 ml) was added potassium-tert-butoxide (191 mg), and the mixture was stirred at room temperature for 30 minutes. Methyl 2-methoxy-4-(2,3,4,5-tetrahydro-5-oxo-1H-1-benzazepin-1-yl)carbonylbenzoate (300 mg) was added to the resulting solution, and the mixture was stirred at room temperature overnight. The mixture was diluted with ethyl acetate and the solution was washed successively with 1N hydrochloric acid, water and brine. The organic layer was dried over magnesium sulfate and the solvent was evaporated in vacuo to give an oil. The crude product was purified by silica gel column chromatography (10% ethyl acetate in hexane) to give methyl 2-methoxy-4-(2,3,4,5-tetrahydro-5-methylene-1H-1-benzazepin-1-yl)carbonylbenzoate (65 mg).

¹H-NMR (300 Mz, CDCl₃, δ): 1.90–2.13(m, 2H), 2.43(m, 1H), 2.73(m, 1H), 3.03(m, 1H), 3.67(s, 3H), 3.82(s, 3H), 4.93(m, 1H), 5.18(s, 1H), 5.30(s, 1H), 6.62(d, J=8 Hz, 1H), 6.72(s, 1H), 6.86(d, J=8 Hz, 1H), 6.97(t, J=8 Hz, 1H), 7.14(t, J=8 Hz, 1H), 7.32(d, J=8 Hz, 1H), 7.59(d, J=8 Hz, 1H).

PREPARATION 14

2-Methoxy-4-(2,3,4,5-tetrahydro-5-methylene-1H-1-benzazepin-1-yl)carbonylbenzoic acid was obtained in substantially the same manner as in Preparation 2.

¹H-NMR (300 MHz, CDCl₃, δ): 1.59(m, 1H), 2.02(m, 1H), 2.43(m, 1H), 2.74(m, 1H), 3.05(m, 1H), 3.86(s, 3H), 4.91(m, 1H), 5.19(s, 1H), 5.31(s, 1H), 6.62(d, J=8 Hz, 1H), 6.88(s, 1H), 6.91(d, J=8 Hz, 1H), 7.00(t, J=8 Hz, 1H), 7.19(t, J=8 Hz, 1H), 7.33(d, J=8 Hz, 1H), 7.93(d, J=8 Hz, 1H).

EXAMPLE 21

2-Methoxy-N-(2-methyl-1H-benzimidazol-4-yl)-4-(2,3,4,5-tetrahydro-5-methylene-1H-1-benzazepin-1-yl)carbonylbenzamide was obtained in substantially the same manner as in Example 1.

¹H-NMR (300 MHz, CDCl₃, δ): 1.62(m, 1H), 2.05(m, 1H), 2.49(m, 1H), 2.61(s, 3H), 2.76(m, 1H), 3.07(m, 1H), 3.90(s, 3H), 4.94(m, 1H), 5.19(s, 1H), 5.31(s, 1H), 6.64(d, J=8 Hz, 1H), 6.85(s, 1H), 6.92–7.00(m, 3H), 7.10–7.20(m, 3H), 7.33(d, J=8 Hz, 1H), 8.07(d, J=8 Hz, 1H).

EXAMPLE 22

2-Methoxy-N-(2-methyl-1H-benzimidazol-4-yl)-4-(2,3,4,5-tetrahydro-5-methylene-1H-1-benzazepin-1-yl)carbonylbenzamide hydrochloride was obtained in substantially the same manner as in Example 10.

¹H-NMR (300 MHz, DMSO-d₆, δ): 1.83–1.94(m, 2H), 2.31–2.60(m, 2H), 2.74(s, 3H), 3.01(m, 1H), 3.72(s, 3H), 4.78(m, 1H), 5.23(s, 1H), 5.36(s, 1H), 6.75–6.90(m, 3H), 7.08(t, J=8 Hz, 1H), 7.22(t, J=8 Hz, 1H), 7.36(d, J=8 Hz, 1H), 7.43(d, J=8 Hz, 1H), 7.50–7.59(m, 2H), 7.66(d, J=8 Hz, 1H).

EXAMPLE 23

2-Methoxy-N-[2-(4-tert-butoxycarbonylpiperazin-1-yl)methyl-1H-benzimidazol-4-yl]-4-(2,3,4,5-tetrahydro-1H-1-benzazepin-1-yl)carbonylbenzamide was obtained in substantially the same manner as in Example 1.

MS (ES–): 637 (M–H)

EXAMPLE 24

2-Methoxy-N-[2-(piperazin-1-yl)methyl-1H-benzimidazol-4-yl]-4-(2,3,4,5-tetrahydro-1H-1-benzazepin-1-yl)carbonylbenzamide was obtained in substantially the same manner as in Example 2.

¹H-NMR (300 MHz, CDCl₃, δ): 1.53(m, 1H), 1.84–2.17 (m, 3H), 2.54–2.61(m, 4H), 2.73–3.09(m, 7H), 3.80(s, 2H), 3.94(s, 3H), 5.01(m, 1H), 6.63(d, J=8 Hz, 1H), 6.80(d, J=8 Hz, 1H), 6.89–7.00(m, 3H), 7.11(t, J=8 Hz, 1H), 7.15–7.26 (m, 3H), 8.05(d, J=8 Hz, 1H).

EXAMPLE 25

2-Methoxy-N-[2-(piperazin-1-yl)methyl-1H-benzimidazol-4-yl]-4-(2,3,4,5-tetrahydro-1H-1-benzazepin- 1-yl)carbonylbenzamide trihydrochloride was obtained in substantially the same manner as in Example 10.

¹H-NMR (300 MHz, DMSO-d₆, δ): 1.44(m, 1H), 1.81–1.96(m, 2H), 2.07(m, 1H), 2.71(m, 1H), 2.87(m, 1H), 2.95–3.10(m, 5H), 3.17–3.29(m, 4H), 3.80(s, 3H), 4.29(s, 2H), 4.83(m, 1H), 6.80–6.90(m, 1H), 6.92–7.01(m, 2H) 7.01(t, J=8 Hz, 1H), 7.31(d, J=8 Hz, 1H), 7.40(d, J=8 Hz, 1H), 7.49(d, J=8 Hz, 1H), 7.70(d, J=8 Hz, 1H), 7.89(d, J=8 Hz, 1H), 9.20(br, 1H).

EXAMPLE 26

2-Methoxy-N-(2-tert-butyldimethylsiloxymethyl-1H-benzimidazol-4-yl)-4-(2,3,4,5-tetrahydro-1H-1-benzazepin-1-yl)carbonylbenzamide was obtained in substantially the same manner as in Example 1.

¹H-NMR (300 MHz, CDCl₃, δ): 0.16(s, 6H), 0.97(s, 9H), 1.54(m, 1H), 1.93–2.19(m, 3H), 2.77–3.11(m, 3H), 3.90(s, 3H×½), 3.97(s, 3H×½), 5.00(s, 2H), 5.02(m, 1H), 6.61–7.28 (m, 8H), 8.05(d, J=8 Hz, 1H), 8.35(d, J=8 Hz, 1H), 9.41(br, 1H).

EXAMPLE 27

A mixture of 2-methoxy-N-(2-tert-butyldimethylsiloxymethyl-1H-benzimidazol-4-yl)-4-(2,3, 4,5-tetrahydro-1H-1-benzazepin-1-yl)carbonylbenzamide (250 mg) and tetrabutylammonium fluoride (1 mol solution in tetrahydrofuran 0.9 ml) in tetrahydrofuran (15 ml) was stirred at room temperature for 4 hours, and the solvent was removed by evaporation. The residue was purified by silica gel column chromatography (1% methanol in chloroform) to give 2-methoxy-N-(2-hydroxymethyl-1H-benzimidazol-4-yl)-4-(2,3,4,5-tetrahydro-1H-1-benzazepin-1-yl) carbonylbenzamide (125 mg).

¹H-NMR (300 MHz, CDCl₃, δ): 1.48–2.17(m, 4H), 2.73–3.12(m, 3H), 3.81(s, 3H), 4.85(s, 2H), 5.00(m, 1H), 1.62(d, J=8 Hz, 1H), 6.80–6.84(m, 2H), 6.91(t, J=8 Hz, 1H), 7.05–7.26(m, 5H), 8.00(d, J=8 Hz, 1H).

EXAMPLE 28

2-Methoxy-N-(2-hydroxymethyl-1H-benzimidazol-4-yl)-4-(2,3,4,5-tetrahydro-1H-1-benzazepin-1-yl) carbonylbenzamide hydrochloride was obtained in substantially the same manner as in Example 10.

¹H-NMR (300 MHz, DMSO-d₆, δ): 1.45–1.70(m, 2H), 1.90(m, 1H), 2.04(m, 1H), 2.72(m, 1H), 2.90–3.21(m, 4H), 3.73(s, 3H), 4.84(m, 1H), 4.91(s, 2H), 6.81–6.90(m, 2H), 6.94–7.02(m, 2H), 7.11(t, J=8 Hz, 1H), 7.31(d, J=8 Hz, 1H), 7.40–7.53(m, 2H), 7.62(d, J=8 Hz, 1H), 7.78(d, J=8 Hz, 1H).

PREPARATION 15

Methyl 2-methoxy-4-(2,3,4,5-tetrahydro-7-chloro-1H-1-benzazepin-1-yl)carbonylbenzoate was obtained in substantially the same manner as in Preparation 1.

¹H-NMR (300 MHz, CDCl₃, δ): 1.51(m, 1H), 1.89–2.00 (m, 2H), 2.09(m, 1H), 2.70–3.06(m, 3H), 3.73(s, 3H), 3.83 (s, 2H), 4.98(m, 1H), 6.55(d, J=8 Hz, 1H), 6.67(d, J=8 Hz, 1H), 6.87(s, 1H), 6.89(d, J=8 Hz, 1H), 7.21(s, 1H), 7.56(d, J=8 Hz, 1H).

PREPARATION 16

2-Methoxy-4-(2,3,4,5-tetrahydro-7-chloro-1H-1-benzazepin-1-yl)carbonylbenzoic acid was obtained in substantially the same manner as in Preparation 2.

¹H-NMR (300 MHz, CDCl₃, δ): 1.55(m, 1H), 1.91–2.02 (m, 2H), 2.72–3.04(m, 3H), 3.96(s, 3H), 4.97(m, 1H), 6.55 (d, J=8 Hz, 1H), 6.74(d, J=8 Hz, 1H), 6.90(dd, J=8, 1.5 Hz, 1H), 7.03(s, 1H), 7.27(d, J=1.5 Hz, 1H), 7.92(d, J=8 Hz, 1H).

EXAMPLE 29

2-Methoxy-N-(2-methyl-1H-benzimidazol-4-yl)-4-(2,3, 4,5-tetrahydro-7-chloro-1H-1-benzazepin-1-yl) carbonylbenzamide was obtained in substantially the same manner as in Example 1.

¹H-NMR (300 MHz, CDCl₃, δ): 1.53(m, 1H), 1.90–2.03 (m, 2H), 2.11(m, 1H), 2.60(s, 3H), 2.70–3.09(m, 3H), 3.98 (s, 3H), 5.00(m, 1H), 6.58(d, J=8 Hz, 1H), 6.75(m, 1H), 6.79(d, J=8 Hz, 1H), 6.90(d, J=8 Hz, 1H), 7.02–7.21(m, 4H), 7.50(m, 1H), 8.04(d, J=8 Hz, 1H).

EXAMPLE 30

2-Methoxy-N-(1H-indazol-7-yl)-4-(2,3,4,5-tetrahydro-1H-1-benzazepin-1-yl)carbonylbenzamide was obtained in substantially the same manner as in Example 1.

¹H-NMR (300 MHz, CDCl₃, δ): 1.55(m, 1H), 1.92–2.07 (m, 2H), 2.11(m, 1H), 2.76–3.02(m, 3H), 4.92(s, 2H), 5.02 (m, 1H), 6.65(d, J=8 Hz, 1H), 6.84(d, J=8 Hz, 1H), 6.90–6.99(m, 2H), 7.02(s, 1H), 7.07–7.14(m, 2H), 7.25(m, 1H), 7.58(d, J=8 Hz, 1H), 8.03–8.10(m, 2H).

PREPARATION 17

Methyl 2-methoxy-4-(2,3,4,5-tetrahydro-9-methyl-1H-1-benzazepin-1-yl)carbonylbenzoate was obtained in substantially the same manner as in Preparation 1.

¹H-NMR (300 MHz, CDCl₃, δ): 1.50(m, 1H), 1.84(s, 3H), 1.93(m, 1H), 1.99–2.16(m, 2H), 2.71(m, 1H), 2.86(m, 1H), 3.10(m, 1H), 3.60(s, 3H), 3.83(s, 3H), 4.97(m, 1H), 6.8i(s, 1H), 6.82–6.88(m, 2H), 7.01–7.12(m, 2H), 7.56(d, J=8 Hz, 1H).

PREPARATION 18

2-Methoxy-4-(2,3,4,5-tetrahydro-9-methyl-1H-1-benzazepin-1-yl)carbonylbenzoic acid was obtained in substantially the same manner as in Preparation 2.

¹H-NMR (300 MHz, CDCl₃, δ): 1.52(m, 1H), 1.85(s, 3H), 1.92(m, 1H), 2.00–2.17(m, 2H), 2.74(m, 1H), 2.89(m, 1H), 3.08(m, 1H), 3.80(s, 3H), 4.94(m, 1H), 6.88(d, J=8 Hz, 1H), 6.92–6.97(m, 2H), 7.04–7.15(m, 2H), 7.90(d, J=8 Hz, 1H).

EXAMPLE 31

2-Methoxy-N-(2-methyl-1H-benzimidazol-4-yl)-4-(2,3, 4,5-tetrahydro-9-methyl-1H-1-benzazepin-1-yl) carbonylbenzamide was obtained in substantially the same manner as in Example 1.

¹H-NMR (300 MHz, CDCl₃, δ): 1.53(m, 1H), 1.88(s, 3H), 1.95(m, 1H), 2.03–2.20(m, 2H), 2.60(s, 3H), 2.74(m, 1H), 2.90(m, 1H), 3.13(m, 1H), 3.83(s, 3H), 4.97(m, 1H), 6.73(m, 1H), 6.84–6.96(m, 2H), 6.98–7.20(m, 4H), 7.51(m, 1H), 8.04(d, J=8 Hz, 1H).

EXAMPLE 32

2-Methoxy-N-(2-methyl-1H-benzimidazol-4-yl)-4-(2,3, 4,5-tetrahydro-9-methyl-1H-1-benzazepin-1-yl) carbonylbenzamide hydrochloride was obtained in substantially the same manner as in Example 10.

¹H-NMR (300 MHz, DMSO-d₆, δ): 1.42(m, 1H), 1.84–2.13(m, 3H), 1.88(s, 3H), 2.70(m, 1H), 2.76(s, 3H), 2.90(m, 1H), 3.11(m, 1H), 3.65(s, 3H), 4.80(m, 1H), 6.83(s,

1H), 6.91–7.00(m, 2H), 7.07–7.14(m, 2H), 7.21(d, J=8 Hz, 1H), 7.46(d, J=8 Hz, 1H), 7.50–7.60(m, 2H), 7.66(d, J=8 Hz, 1H).

EXAMPLE 33

N-[2-(Imidazol-1-yl)-1H-benzimidazol-4-yl]-2-methoxy-4-(2,3,4,5-tetrahydro-1H-1-benzazepin-1-yl) carbonylbenzamide was obtained in substantially the same manner as in Example 1.

$^1$H-NMR (300 MHz, DMSO-d$_6$, δ): 1.33–1.53(m, 1H), 1.80–2.00(m, 2H), 2.00–2.15(m, 1H), 2.68–2.81(m, 1H), 2.81–2.98(m, 1H), 2.98–3.17(m, 1H), 4.00(s, 3H), 4.79–4.91(m, 1H), 6.81(d, J=8 Hz, 1H), 6.90–7.01(m, 2H), 7.03(s, 1H), 7.10(t, J=8 Hz, 1H), 7.18–7.40(m, 4H), 7.84–8.00(m, 2H), 8.19(br, 1H), 8.47(s, 1H).

EXAMPLE 34

N-[2-(Imidazol-1-yl)-1H-benzimidazol-4-yl]-2-methoxy-4-(2,3,4,5-tetrahydro-1H-1-benzazepin-1-yl) carbonylbenzamide dihydrochloride was obtained in substantially the same manner as in Example 10.

$^1$H-NMR (300 MHz, DMSO-d$_6$, δ): 1.33–1.53(m, 1H), 1.83–1.99(m, 2H), 2.67–2.83(m, 1H), 2.83–2.99(m, 1H), 3.00–3.15(m, 1H), 3.99(s, 3H), 4.79–4.90(m, 1H), 6.83(d, J=8 Hz, 1H), 6.90–7.01(m, 2H), 7.05(s, 1H), 7.11(t, J=8 Hz, 1H), 7.23–7.40(m, 3H), 7.61(br, 1H), 7.90(d, J=8 Hz, 1H), 8.13–8.25(m, 2H), 9.16(br, 1H).

EXAMPLE 35

N-[2-(tert-Butoxycarbonylamino)-1H-benzimidazol-4-yl]-2-methoxy-4-(2,3,4,5-tetrahydro-1H-1-benzazepin-1-yl) carbonylbenzamide was obtained in substantially the same manner as in Example 1.

$^1$H-NMR (300 MHz, DMSO-d$_6$, δ): 1.34–1.55(m, 1H), 1.67(s, 9H), 1.81–1.97(m, 1H), 1.97–2.14(m, 1H), 2.67–2.83(m, 1H), 2.83–2.97(m, 1H), 3.00–3.15(m, 1H), 3.95(s, 3H), 4.77–4.90(m, 1H), 6.80(d, J=8 Hz, 1H), 6.88–7.01(m, 3H), 7.11(t, J=8 Hz, 1H), 7.26–7.42(m, 3H), 7.88(d, J=8 Hz, 1H), 8.10(d, J=8 Hz, 1H).

EXAMPLE 36

N-(2-Amino-1H-benzimidazol-4-yl)-2-methoxy-4-(2,3,4,5-tetrahydro-1H-1-benzazepin-1-yl)carbonylbenzamide was obtained in substantially the same manner as in Example 2.

$^1$H-NMR (300 MHz, DMSO-d$_6$, δ): 1.33–1.53(m, 1H), 1.79–1.99(m, 2H), 1.99–2.13(m, 1H), 2.66–2.81(m, 1H), 2.81–2.98(m, 1H), 2.98–3.15(m, 1H), 3.89(s, 3H), 4.77–4.91(m, 1H), 6.25(br, 2H), 6.73–6.84(m, 2H), 6.84–7.01(m, 4H), 7.10(t, J=8 Hz, 1H), 7.31(d, J=8 Hz, 1H), 7.81(br, 2H).

EXAMPLE 37

N-(2-Amino-1H-benzimidazol-4-yl)-2-methoxy-4-(2,3,4,5-tetrahydro-1H-1-benzazepin-1-yl)carbonylbenzamide hydrochloride was obtained in substantially the same manner as in Example 10.

$^1$H-NMR (300 MHz, DMSO-d$_6$, δ): 1.33–1.51(m, 1H), 1.81–1.96(m, 2H), 1.99–2.11(m, 1H), 2.66–2.81(m, 1H), 2.81–2.96(m, 1H), 2.96–3.11(m, 1H), 3.71(s, 3H), 4.77–4.90(m, 1H), 6.80–6.90(m, 2H), 6.92–7.03(m, 2H), 7.13(t, J=8 Hz, 1H), 7.15–7.23(m, 2H), 7.28–7.35(m, 2H), 7.53(d, J=8 Hz, 1H), 8.26(br, 2H).

EXAMPLE 38

A mixture of N-(2-amino-1H-benzimidazol-4-yl)-2-methoxy-4-(2,3,4,5-tetrahydro-1H-1-benzazepin-1-yl) carbonylbenzamide (90 mg) and acetic anhydride (1.0 ml) was stirred for 1 hour at room temperature and allowed to stand overnight at the same temperature. The reaction mixture was concentrated in vacuo and the residue was dissolved in chloroform. The resulting solution was washed with saturated aqueous sodium hydrogencarbonate solution, water and brine, and dried over magnesium sulfate. The solvent was evaporated in vacuo. The residue was purified by preparative thin-layer chromatography (chloroform-ethyl acetate=10-1) to give N-(2-acetamido-1H-benzimidazol-4-yl)-2-methoxy-4-(2,3,4,5-tetrahydro-1H-1-benzazepin-1-yl) carbonylbenzamide (42 mg).

$^1$H-NMR (300 MHz, DMSO-d$_6$, δ): 1.33–1.52(m, 1H), 1.80–1.98(m, 2H), 1.98–2.13(m, 1H), 2.21(s, 3H), 2.66–2.81(m, 1H), 2.81–2.97(m, 1H), 2.97–3.15(m, 1H), 3.98(s, 3H), 4.78–4.90(m, 1H), 6.80(d, J=8 Hz, 1H), 6.87–7.07(m, 4H), 7. 7.11(t, J=8 Hz, 1H), 7.21(d, J=8 Hz, 1H), 7.31(d, J=8 Hz, 1H), 7.88(d, J=8 Hz, 1H), 8.03(d, J=8 Hz, 1H).

EXAMPLE 39

N-(2-Acetamido-1H-benzimidazol-4-yl)-2-methoxy-4-(2,3,4,5-tetrahydro-1H-1-benzazepin-1-yl) carbonylbenzamide hydrochloride was obtained in substantially the same manner as in Example 10.

$^1$H-NMR (300 MHz, DMSO-d$_6$, δ): 1.41(br, 1H), 1.81–1.98(m, 2H), 1.98–2.13(m, 1H), 2.22(s, 3H), 2.66–2.81(m, 1H), 2.81–2.96(m, 1H), 3.00–3.14(m, 1H), 3.87(s, 3H), 4.77–4.90(m, 1H), 6.81(d, J=8 Hz, 1H), 6.89(d, J=8 Hz, 1H), 6.93–7.02(m, 2H), 7.09–7.20(m, 2H), 7.25–7.36(m, 2H), 7.70(d, J=8 Hz, 1H), 7.88(d, J=8 Hz, 1H).

EXAMPLE 40

2-Methoxy-N-(2-methylsulfonylamino-1H-benzimidazol-4-yl)-4-(2,3,4,5-tetrahydro-1H-1-benzazepin-1-yl)carbonylbenzamnide was obtained in substantially the same manner as in Example 13.

$^1$H-NMR (300 MHz, CDCl$_3$, δ): 1.43–1.63(m, 1H), 1.81–2.05(m, 2H), 2.05–2.19(m, 1H), 2.73–2.99(m, 2H), 2.99–3.13(m, 1H), 3.21(s, 3H), 3.95(s, 3H), 4.95–5.06(m, 1H), 5.58(br, 2H), 6.63(d, J=8 Hz, 1H), 6.81(d, J=8 Hz, 1H), 6.91(t, J=8 Hz, 1H), 6.98(s, 1H), 7.05–7.19(m, 2H), 7.21–7.28(m, 1H), 7.36(d, J=8 Hz, 1H), 8.03(d, J=8 Hz, 1H), 8.38(d, J=8 Hz, 1H).

EXAMPLE 41

2-Methoxy-N-(2-methylsulfonylamino-1H-benzimidazol-4-yl)-4-(2,3,4,5-tetrahydro-1H-1-benzazepin-1-yl)carbonylbenzamide hydrochloride was obtained in substantially the same manner as in Example 10.

$^1$H-NMR (300 MHz, DMSO-d$_6$, δ): 1.43(br, 1H), 1.83–1.98(m, 2H), 1.98–2.13(m, 1H), 2.68–2.81(m, 1H), 2.81–2.97(m, 1H), 2.97–3.14(m, 1H), 3.94(s, 3H), 4.78–4.89(m, 1H), 6.80(d, J=8 Hz, 1H), 6.88–7.16(m, 5H), 7.23–7.37(m, 2H), 7.85(d, J=8 Hz, 1H), 8.17(d, J=8 Hz, 1H).

EXAMPLE 42

2-Methoxy-4-[(2,3,4,5-tetrahydro-1H-1-benzazepin-1-yl) carbonyl]-N-(2-trifluoromethyl-1H-benzimidazol-4-yl) benzamide was obtained in substantially the same manner as in Example 1.

$^1$H-NMR (300 MHz, DMSO-d$_6$, δ): 1.42(br, 1H), 1.83–1.97(m, 2H), 1.97–2.11(m, 1H), 2.67–2.81(m, 1H), 2.81–2.96(m, 1H), 3.00–3.15(m, 1H), 3.93(s, 3H), 4.79–4.89(m, 1H), 6.81(d, J=8 Hz, 1H), 6.88–7.00(m, 2H), 7.02(s, 1H), 7.11(t, J=8 Hz, 1H), 7.29–7.43(m, 3H), 7.89(br, 1H), 8.22(br, 1H).

EXAMPLE 43

N-(1,2-Dimethyl-1H-benzimidazol-4-yl)-2-methoxy-4-(2,3,4,5-tetrahydro-1H-1-benzazepin-1-yl) carbonylbenzamide was obtained in substantially the same manner as in Example 1.

$^1$H-NMR (300 MHz, DMSO-d$_6$, δ): 1.43(br, 1H), 1.81–1.98(m, 2H), 1.98–2.13(m, 1H), 2.58(s, 3H), 2.67–2.81(m, 1H), 2.85–2.96(m, 1H), 3.01–3.14(m, 1H), 3.73(s, 3H), 3.94(s, 3H), 4.78–4.90(m, 1H), 6.80(d, J=8 Hz, 1H), 6.87–7.03(m, 3H), 7.05–7.25(m, 3H), 7.31(d, J=8 Hz, 1H), 7.88(d, J=8 Hz, 1H), 8.01(d, J=8 Hz, 1H).

EXAMPLE 44

N-(1,2-Dimethyl-1H-benzimidazol-4-yl)-2-methoxy-4-(2,3,4,5-tetrahydro-1H-1-benzazepin-1-yl) carbonylbenzamide hydrochloride was obtained in substantially the same manner as in Example 10.

$^1$H-NMR (300 MHz, DMSO-d$_6$, δ): 1.43(br, 1H), 1.82–1.96(m, 2H), 1.96–2.13(m, 1H), 2.66–2.83(m, 4H), 2.83–2.95(m, 1H), 2.99–3.13(m, 1H), 3.78(s, 3H), 3.89(s, 3H), 4.78–4.90(m, 1H), 6.82(d, J=8 Hz, 1H), 6.88(d, J=8 Hz, 1H), 6.94–7.03(m, 2H), 7.11(t, J=8 Hz, 1H), 7.31(d, J=8 Hz, 1H), 7.41–7.55(m, 1H), 7.60–7.73(m, 3H).

EXAMPLE 45

N-(2,3-Dimethyl-3H-benzimidazol-4-yl)-2-methoxy-4-(2,3,4,5-tetrahydro-1H-1-benzazepin-1-yl) carbonylbenzamide was obtained in substantially the same manner as in Example 1.

$^1$H-NMR (300 MHz, CDCl$_3$, δ): 1.46–1.69(m, 1H), 1.93–2.19(m, 3H), 2.54(s, 3H), 2.74–2.97(m, 2H), 2.97–3.13(m, 1H), 3.76(s, 3H), 3.90(s, 3H), 4.46–5.06(m, 1H), 6.68(d, J=8 Hz, 1H), 6.81(d, J=8 Hz, 1H), 6.95(t, J=8 Hz, 1H), 7.04–7.22(m, 4H), 7.22–7.31(m, 1H), 7.60(d, J=8 Hz, 1H), 8.01(d, J=8 Hz, 1H), 9.42(s, 1H).

EXAMPLE 46

N-(2,3-Dimethyl-3H-benzimidazol-4-yl)-2-methoxy-4-(2,3,4,5-tetrahydro-1H-1-benzazepin-1-yl) carbonylbenzamide hydrochloride was obtained in substantially the same manner as in Example 10.

$^1$H-NMR (300 MHz, DMSO-d$_6$, δ): 1.43(br, 1H), 1.81–1.98(m, 2H), 1.98–2.11(m, 1H), 2.68–2.83(m, 4H), 2.83–2.95(m, 1H), 2.99–3.12(m, 1H), 3.74(s, 3H), 3.94(s, 3H), 4.77–4.90(m, 1H), 6.81–6.90(m, 2H), 6.95–7.05(m, 2H), 7.12(t, J=8 Hz, 1H), 7.32(d, J=8 Hz, 1H), 7.40(d, J=8 Hz, 1H), 7.50(t, J=8 Hz, 1H), 7.55(d, J=8 Hz, 1H), 7.67(d, J=8 Hz, 1H).

EXAMPLE 47

N-(2-Dimethylamino-1H-benzimidazol-4-yl)-2-methoxy-4-(2,3,4,5-tetrahydro-1H-1-benzazepin-1-yl) carbonylbenzamide was obtained in substantially the same manner as in Example 1.

$^1$H-NMR (300 MHz, DMSO-d$_6$, δ): 1.41(br, 1H), 1.80–1.97(m, 2H), 1.97–2.11(m, 1H), 2.67–2.81(m, 1H), 2.81–2.94(m, 1H), 3.00–3.19(m, 7H), 3.92(s, 3H), 4.77–4.90(m, 1H), 6.75–7.03(m, 6H), 7.11(t, J=8 Hz, 1H), 7.31(d, J=8 Hz, 1H), 7.91(d, J=8 Hz, 1H), 7.99(d, J=8 Hz, 1H).

EXAMPLE 48

N-(2-Dimethylamino-1H-benzimidazol-4-yl)-2-methoxy-4-(2,3,4,5-tetrahydro-1H-1-benzazepin-1-yl) carbonylbenzamide hydrochloride was obtained in substantially the same manner as in Example 10.

$^1$H-NMR (300 MHz, DMSO-d$_6$, δ): 1.42(br, 1H), 1.81–1.98(m, 2H), 1.98–2.11(m, 1H), 2.66–2.80(m, 1H), 2.84–2.96(m, 1H), 2.96–3.12(m, 1H), 3.21(s, 6H), 3.71(s, 3H), 4.78–4.89(m, 1H), 6.78–6.89(m, 2H), 6.95(s, 1H), 7.00(t, J=8 Hz, 1H), 7.06–7.26(m, 3H), 7.31(d, J=8 Hz, 1H), 7.54(br, 1H), 7.68(br, 1H).

EXAMPLE 49

N-(1H-Benzimidazol-4-yl)-2-methoxy-4-(2,3,4,5-tetrahydro-1H-1-benzazepin-1-yl)carbonylbenzamide was obtained in substantially the same manner as in Example 1.

$^1$H-NMR (300 MHz, DMSO-d$_6$, δ): 1.43(br, 1H), 1.81–1.98(m, 2H), 1.98–2.13(m, 1H), 2.68–2.81(m, 1H), 2.83–2.96(m, 1H), 3.00–3.15(m, 1H), 3.91(s, 3H), 4.79–4.90(m, 1H), 6.81(d, J=8 Hz, 1H), 6.89–7.03(m, 3H), 7.06–7.22(m, 2H), 7.22–7.35(m, 2H), 7.89(br, 1H), 8.15(br, 1H), 8.22(s, 1H).

EXAMPLE 50

N-(1H-Benzimidazol-4-yl)-2-methoxy-4-(2,3,4,5-tetrahydro-1H-1-benzazepin-1-yl)carbonylbenzamide hydrochloride was obtained in substantially the same manner as in Example 10.

$^1$H-NMR (300 MHz, DMSO-d$_6$, δ): 1.43(br, 1H), 1.81–1.98(m, 2H), 1.98–2.13(m, 1H), 2.66–2.81(m, 1H), 2.81–2.97(m, 1H), 3.00–3.14(m, 1H), 3.80(s, 3H), 4.78–4.90(m, 1H), 6.83(d, J=8 Hz, 1H), 6.89(d, J=8 Hz, 1H), 6.95–7.05(m, 2H), 7.13(t, J=8 Hz, 1H), 7.32(d, J=8 Hz, 1H), 7.43(t, J=8 Hz, 1H), 7.54(d, J=8 Hz, 1H), 7.69(d, J=8 Hz, 1H), 7.79(d, J=8 Hz, 1H), 9.13(br, 1H).

EXAMPLE 51

2-Methoxy-N-(2-methoxy-1H-benzimidazol-4-yl)-4-(2,3,4,5-tetrahydro-1H-1-benzazepin-1-yl)carbonylbenzamide was obtained in substantially the same manner as in Example 1.

$^1$H-NMR (300 MHz, DMSO-d$_6$, δ): 1.42(br, 1H), 1.82–1.98(m, 2H), 1.98–2.11(m, 1H), 2.66–2.81(m, 1H), 2.81–2.96(m, 1H), 2.96–3.14(m, 1H), 3.94(s, 3H), 4.11(s, 3H), 4.78–4.90(m, 1H), 6.80(d, J=8 Hz, 1H), 6.89–7.06(m, 5H), 7.10(t, J=8 Hz, 1H), 7.31(d, J=8 Hz, 1H), 7.90(br, 1H), 8.06(br, 1H).

EXAMPLE 52

2-Methoxy-N-(2-methoxymethyl-1H-benzimidazol-4-yl)-4-(2,3,4,5-tetrahydro-1H-1-benzazepin-1-yl) carbonylbenzamide was obtained in substantially the same manner as in Example 1.

$^1$H-NMR (300 MHz, DMSO-d$_6$, δ): 1.43(br, 1H), 1.81–1.97(m, 2H), 1.97–2.13(m, 1H), 2.66–2.83(m, 1H), 1.83–2.97(m, 1H), 3.00–3.15(m, 1H), 3.39(s, 3H), 3.94(s, 3H), 4.68(s, 2H), 4.79–4.90(m, 1H), 6.81(d, J=8 Hz, 1H), 6.88–7.04(m, 3H), 7.04–7.24(m, 3H), 7.31(d, J=8 Hz, 1H), 7.90(d, J=8 Hz, 1H), 8.10(d, J=8 Hz, 1H).

EXAMPLE 53

2-Methoxy-N-(2-methoxymethyl-1H-benzimidazol-4-yl)-4-(2,3,4,5-tetrahydro-1H-1-benzazepin-1-yl)

rcarbonylbenzamide hydrochloride was obtained in substantially the same manner as in Example 10.

$^1$H-NMR (300 MHz, DMSO-d$_6$, δ): 1.43(br, 1H), 1.83–1.97(m, 2H), 1.99–2.12(m, 1H), 2.66–2.81(m, 1H), 2.85–2.95(m, 1H), 3.00–3.14(m, 1H), 3.45(s, 3H), 3.80(s, 3H), 4.77–4.89(m, 3H), 6.83(d, J=8 Hz, 1H), 6.89(d, J=8 Hz, 1H), 6.93–7.03(m, 2H), 7.13(t, J=8 Hz, 1H), 7.31(d, J=8 Hz, 1H), 7.35–7.50(m, 2H), 7.70(d, J=8 Hz, 1H), 7.83(d, J=8 Hz, 1H).

EXAMPLE 54

N-(2-Ethyl-1H-benzimidazol-4-yl)-2-methoxy-4-(2,3,4,5-tetrahydro-1H-1-benzazepin-1-yl)carbonylbenzamide was obtained in substantially the same manner as in Example 1.

$^1$H-NMR (300 MHz, DMSO-d$_6$, δ): 1.31–1.51(m, 4H), 1.82–1.96(m, 2H), 2.00–2.12(m, 1H), 2.65–2.81(m, 1H), 2.81–2.96(m, 3H), 3.00–3.15(m, 1H), 3.94(s, 3H), 4.78–4.90(m, 1H), 6.80(d, J=8 Hz, 1H), 6.88–7.03(m, 3H), 7.03–7.18(m, 3H), 7.32(d, J=8 Hz, 1H), 7.90(d, J=8 Hz, 1H), 8.08(d, J=8 Hz, 1H).

EXAMPLE 55

N-(2-Ethyl-1H-benzimidazol-4-yl)-2-methoxy-4-(2,3,4,5-tetrahydro-1H-1-benzazepin-1-yl)carbonylbenzamide hydrochloride was obtained in substantially the same manner as in Example 10.

$^1$H-NMR (300 MHz, DMSO-d$_6$, δ): 1.33–1.50(m, 4H), 1.83–1.97(m, 2H), 1.97–2.11(m, 1H), 2.66–2.81(m, 1H), 2.81–2.96(m, 1H), 3.00–3.17(m, 3H), 3.76(s, 3H), 14.78–4.90(m, 1H), 6.83(d, J=8 Hz, 1H), 6.88(d, J=8 Hz, 1H), 6.94–7.04(m, 2H), 7.13(t, J=8 Hz, 1H), 7.33(d, J=8 Hz, 1H), 7.38–7.49(m, 1H), 7.49–7.56(m, 1H), 7.60–7.70(m, 1H).

EXAMPLE 56

N-[(1-tert-Butoxycarbonyl)-2-[2-(N-methyl-N-tert-butoxycarbonyl-amino)ethylamino]-1H-benzimidazol-4-yl]-2-methoxy-4-(2,3,4,5-tetrahydro-1H-1-benzazepin-1-yl)carbonylbenzamide was obtained in substantially the same manner as in Example 1.

$^1$H-NMR (300 MHz, CDCl$_3$, δ): 1.36–1.64(m, 10H), 1.70(s, 9H), 1.92–2.07(m, 2H), 2.07–2.20(m, 1H), 2.75–2.98(m, 5H), 3.01–3.14(m, 1H), 3.57–3.66(m, 2H), 3.74(br, 2H), 3.95(s, 3H), 4.95–5.08(m, 1H), 6.64(d, J=8 Hz, 1H), 6.83(d, J=8 Hz, 1H), 6.92(t, J=8 Hz, 1H), 6.95–7.07(m, 2H), 7.10(t, J=8 Hz, 1H), 7.22–7.34(m, 2H), 7.44(br, 1H), 8.07(d, J=8 Hz, 1H), 8.38(d, J=8 Hz, 1H).

EXAMPLE 57

2-Methoxy-N-[2-[2-(methylamino)ethylamino]-1H-benzimidazol-4-yl]-4-(2,3,4,5-tetrahydro-1H-1-benzazepin-1-yl)carbonylbenzamide was obtained in substantially the same manner as in Example 2.

$^1$H-NMR (300 MHz, DMSO-d$_6$, δ): 1.43(br, 1H), 1.90(br, 2H), 1.99–2.11(m, 1H), 2.38(s, 3H), 2.65–2.98(m, 4H), 3.00–3.13(m,1H), 3.26–3.52(m, 2H), 3.90(s, 3H), 4.78–4.90(m, 1H), 6.64(br, 1H), 6.75–6.85(m, 2H), 6.85–7.01(m, 4H), 7.11(t, J=8 Hz, 1H), 7.31(d, J=8 Hz, 1H), 7.78–7.91(m, 2H).

EXAMPLE 58

2-Methoxy-N-[2-[2-(methylamino)ethylamino]-1H-benzimidazol-4-yl]-4-(2,3,4,5-tetrahydro-1H-1-benzazepin-1-yl) carbonylbenzamide dihydrochoride was obtained in substantially the same manner as in Example 10.

$^1$H-NMR (300 MHz, DMSO-d$_6$, δ): 1.41(br, 1H), 1.81–1.95(m, 2H), 1.95–2.11(m, 1H), 2.62(s, 3H), 2.67–2.80(m, 1H), 2.82–2.94(m, 1H), 2.94–3.12(m, 1H), 3.17–3.29(m, 2H), 3.71(s, 3H), 3.73–3.85(m, 2H), 4.79–4.90(m, 1H), 6.83(d-like, 2H), 6.93(s, 1H), 7.00(t, J=8 Hz, 1H), 7.12(t, J=8 Hz, 1H), 7.18–7.29(m, 2H), 7.32(d, J=8 Hz, 1H), 7.46–7.58(m, 2H), 9.01(br, 3H).

EXAMPLE 59

2-Methoxy-N-(2-n-propyl-1H-benzimidazol-4-yl)-4-(2,3,4,5-tetrahydro-1H-1-benzazepin-1-yl)carbonylbenzamide was obtained in substantially the same manner as in Example 1.

$^1$-NMR (300 MHz, DMSO-d$_6$, δ): 0.99(t, J=7.5 Hz, 3H), 1.41(br, 1H), 1.76–1.98(m, 4H), 2.05(br, 1H), 2.16–2.96(m, 4H), 3.01–3.14(m, 1H), 3.94(s, 3H), 4.79–4.90(m, 1H), 6.80(d, J=8 Hz, 1H), 6.87–7.02(m, 3H), 7.02–7.20(m, 3H), 7.33(d, J=8 Hz, 1H), 7.90(d, J=8 Hz, 1H), 8.08(d, J=8 Hz, 1H).

EXAMPLE 60

2-Methoxy-N-(2-n-propyl-1H-benzimidazol-4-yl)-4-(2,3,4,5-tetrahydro-1H-1-benzazepin-1-yl)carbonylbenzamide hydrochloride was obtained in substantially the same manner as in Example 10.

$^1$H-NMR (300 MHz, DMSO-d$_6$, δ): 0.97(t, J=7.5 Hz, 3H), 1.41(br, 1H), 1.78–1.98(m, 4H), 1.98–2.12(m, 1H), 2.66–2.80(m, 1H), 2.83–2.98(m, 1H), 2.98–3.15(m, 3H), 3.75(s, 3H), 4.79–4.91(m, 1H), 6.83(d, J=8 Hz, 1H), 6.88(d, J=8 Hz, 1H), 6.96(s, 1H), 7.00(t, J=8 Hz, 1H), 7.13(t, J=8 Hz, 1H), 7.31(d, J=8 Hz, 1H), 7.40–7.50(m, 1H), 7.50–7.60(m, 1H), 7.60–7.71(m, 2H).

EXAMPLE 61

2-Methoxy-N-[2-(4-methylpiperazin-1-yl)-1H-benzimidazol-4-yl]-4-(2,3,4,5-tetrahydro-1H-1-benzazepin-1-yl)carbonylbenzamide was obtained in substantially the same manner as in Example 1.

$^1$H-NMR (300 MHz, DMSO-d$_6$, δ): 1.42(br, 1H), 1.81–1.98(m, 2H), 1.98–2.11(m, 1H), 2.23(s, 3H), 2.38–2.53(m, 4H), 2.66–2.80(m, 1H), 2.80–2.95(m, 1H), 3.00–3.15(m, 1H), 3.49–3.59(m, 4H), 3.91(s, 3H), 4.79–4.90(m, 1H), 6.75–7.04(m, 6H), 7.10(t, J=8 Hz, 1H), 7.31(d, J=8 Hz, 1H), 7.90(d, J=8 Hz, 1H), 8.00(d, J=8 Hz, 1H).

EXAMPLE 62

2-Methoxy-N-[2-(4-methylpiperazin-1-yl)-1H-benzimidazol-4-yl]-4-(2,3,4,5-tetrahydro-1H-1-benzazepin-1-yl)carbonylbenzamide dihydrochloride was obtained in substantially the same manner as in Example 10.

$^1$H-NMR (300 MHz, DMSO-d$_6$, δ): 1.43(br, 1H), 1.81–1.98(m, 2H), 1.98–2.13(m, 1H), 2.65–2.96(m, 5H), 2.96–3.13(m, 1H), 3.13–3.33(m, 2H), 3.33–3.88(m, 7H), 4.25–4.40(m, 2H), 4.78–4.90(m, 1H), 6.78–6.90(m, 2H), 6.93–7.03(m, 2H), 7.07–7.28(m, 3H), 7.31(d, J=8 Hz, 1H), 7.63(br, 1H), 7.78(br, 1H).

EXAMPLE 63

N-[2-[N-[2-(Dimethylamino)ethyl]-N-methylamino]-1H-benzimidazol-4-yl]-2-methoxy-4-(2,3,4,5-tetrahydro-1H-1-benzazepin-1-yl)-carbonylbenzamide was obtained in substantially the same manner as in Example 1.

$^1$H-NMR (300 MHz, DMSO-d$_6$, δ): 1.42(br, 1H), 1.82–1.95(m, 2H), 1.95–2.12(m, 1H), 2.21(s, 6H), 2.44–2.54(m, 2H), 2.67–2.80(m, 1H), 2.83–2.95(m, 1H), 2.99–3.15(m, 4H), 3.56–3.66(m, 2H), 3.92(s, 3H), 4.78–4.90(m, 1H), 6.76–6.86(m, 2H), 6.86–7.01(m, 4H), 7.11(t, J=8 Hz, 1H), 7.31(d, J=8 Hz, 1H), 7.90(d, J=8 Hz, 1H), 7.98(d, J=8 Hz, 1H).

EXAMPLE 64

N-[2-[N-[2-(Dimethylamino)ethyl]-N-methylamino]-1H-benzimidazol-4-yl]-2-methoxy-4-(2,3,4,5-tetrahydro-1H-1-benzazepin-1-yl)-carbonylbenzamide dihydrochloride was obtained in substantially the same manner as in Example 10.

$^1$H-NMR (300 MHz, DMSO-d$_6$, δ): 1.42(br, 1H), 1.81–1.98(m, 2H), 1.98–2.11(m, 1H), 2.66–2.81(m, 1H), 2.81–2.96(m, 7H), 2.96–3.11(m, 1H), 3.25(s, 3H), 3.35–3.56(m, 2H), 3.70(s, 3H), 4.02–4.13(m, 2H), 4.78–4.91(m, 1H), 6.76–6.85(m, 2H), 6.92(s, 1H), 7.00(t, J=8 Hz, 1H), 7.13(t, J=8 Hz, 1H), 7.21(br, 2H), 7.32(d, J=8 Hz, 1H), 7.46(br, 1H), 7.82(br, 1H).

PREPARATION 19

To a solution of 2-[2-(dimethylamino)ethylamino]-4-nitro-1H-benzimidazole (105 mg) in ethanol (4 ml) were added iron (reduced, 118 mg) and acetic acid (0.24 ml) at room temperature and the mixture was refluxed for 6 hours. The precipitate was filtered off and the filtrate was evaporated in vacuo. The residue was dissolved in a mixture of chloroform and methanol (5-1) and the organic layer was washed with saturated aqueous sodium hydrogencarbonate solution, and dried over magnesium sulfate. The solvent was evaporated in vacuo. The residue was purified by preparative thin-layer chromatography (chloroform-methanol-ammonia solution (28%)=160-32-1) to give 4-amino-2-[2-(dimethylamino)-ethylamino]-1H-benzimidazole (80 mg).

$^1$H-NMR (300 MHz, CDCl$_3$, δ): 2.35(s, 6H), 2.56–2.64 (m, 2H), 3.35–3.42(m, 2H), 6.45(d, J=8 Hz, 1H), 6.67(d, J=8 Hz, 1H), 6.84(t, J=8 Hz, 1H).

EXAMPLE 65

N-[2-[2-(Dimethylamino)ethylamino]-1H-benzimidazol-4-yl]-2-methoxy-4-(2,3,4,5-tetrahydro-1H-1-benzazepin-1-yl)carbonylbenzamide was obtained in substantially the same manner as in Example 1.

$^1$H-NMR (300 MHz, DMSO-d$_6$, δ): 1.42(br, 1H), 1.82–1.98(m, 2H), 1.98–2.12(m, 1H), 2.20(s, 6H), 2.41–2.53(m, 2H), 2.66–2.82(m, 1H), 2.82–2.96(m, 1H), 3.00–3.15(m, 1H), 3.37–3.50(m, 2H), 3.93(s, 3H), 4.78–4.90(m, 1H), 6.98(t-like, 1H), 6.74–6.84(m, 2H), 6.84–7.02(m, 4H), 7.10(t, J=8 Hz, 1H), 7.30(d, J=8 Hz, 1H), 7.89(d, J=8 Hz, 1H), 7.94(d, J=8 Hz, 1H).

EXAMPLE 66

N-[2-[2-(Dimethylamino)ethylamino]-1H-benzimidazol-4-yl]-2-methoxy-4-(2,3,4,5-tetrahydro-1H-1-benzazepin-1-yl)carbonylbenzamide dihydrochloride was obtained in substantially the same manner as in Example 10.

$^1$H-NMR (300 MHz, DMSO-d$_6$, δ): 1.43(br, 1H), 1.80–1.98(m, 2H), 1.98–2.11(m, 1H), 2.65–2.79(m, 1H), 2.79–2.95(m, 7H), 2.95–3.12(m, 1H), 3.28–3.48(m, 2H), 3.70(s, 3H), 3.81–3.93(m, 2H), 4.78–4.90(m, 1H), 6.80–6.88(m, 2H), 6.93(s, 1H), 7.00(t, J=8 Hz, 1H), 7.12(t, J=8 Hz, 1H), 7.16–7.27(m, 2H), 7.31(d, J=8 Hz, 1H), 7.46–7.57(m, 2H), 9.00(br, 1H).

PREPARATION 20

A mixture of 2-chloro-4-nitro-1H-benzimidazole (300 mg) and morpholine (1 ml) was stirred at 50° C. for 8 hours. The reaction mixture was poured into saturated aqueous sodium hydrogencarbonate solution and extracted with chloroform. The organic layer was washed with brine, and dried over magnesium sulfate. The solvent was evaporated in vacuo. The residue was washed with isopropyl ether and collected by vacuum filtration to give 2-(morpholin-4-yl)-4-nitro-1H-benzimidazole (288 mg).

$^1$H-NMR (300 MHz, DMSO-d$_6$, δ): 3.59–3.68(m, 4H), 3.68–3.79(m, 4H), 7.12(t, J=8 Hz, 1H), 7.59(d, J=8 Hz, 1H), 7.78(d, J=8 Hz, 1H).

PREPARATION 21

4-Amino-2-(morpholin-4-yl)-1H-benzimidazole was obtained in substantially the same manner as in Preparation 19.

$^1$H-NMR (300 MHz, DMSO-d$_6$, δ): 3.35–3.54(m, 4H), 3.66–3.80(m, 4H), 4.71(brs, 2H×⅔), 4.81(brs, 2H×⅓), 6.18–6.29(m, 1H), 6.48(d, J=8 Hz, 1H×⅓), 6.52(d, J=8 Hz, 1H×⅓), 6.60–6.75(m, 1H).

EXAMPLE 67

2-Methoxy-N-[2-(morpholin-4-yl)-1H-benzimidazol-4-yl]-4-(2,3,4,5-tetrahydro-1H-1-benzazepin-1-yl) carbonylbenzamide was obtained in substantially the same manner as in Example 1.

$^1$H-NMR (300 MHz, DMSO-d$_6$, δ): 1.44(br, 1H), 1.90(br, 2H), 1.99–2.13(m, 1H), 2.67–2.83(m, 1H), 2.83–3.00(m, 1H), 3.00–3.14(m, 1H), 3.46–3.58(m, 4H), 3.71–3.83(m, 4H), 3.91(s, 3H), 4.79–4.90(m, 1H), 6.80(d, J=8 Hz, 1H), 6.83–7.02(m, 5H), 7.10(t, J=8 Hz, 1H), 7.32(d, J=8 Hz, 1H), 7.91(d, J=8 Hz, 1H), 8.02(d, J=8 Hz, 1H).

EXAMPLE 68

2-Methoxy-N-[2-(morpholin-4-yl)-1H-benzimidazol-4-yl]-4-(2,3,4,5-tetrahydro-1H-1-benzazepin-1-yl) carbonylbenzamide hydrochloride was obtained in substantially the same manner as in Example 10.

$^1$H-NMR (300 MHz, DMSO-d$_6$, δ): 1.43(br, 1H), 1.83–1.98(m, 2H), 1.98–2.12(m, 1H), 2.66–2.80(m, 1H), 2.83–2.95(m, 1H), 2.95–3.11(m, 1H), 3.60–3.70(m, 4H), 3.73(s, 3H), 3.75–3.84(m, 4H), 4.77–4.89(m, 1H), 6.79–6.88(m, 2H), 6.95(s, 1H), 6.98(t, J=8 Hz, 1H), 7.11(t, J=8 Hz, 1H), 7.20(br, 2H), 7.31(d, J=8 Hz, 1H), 7.57(br, 1H), 7.66(br, 1H).

EXAMPLE 69

N-[2-(Imidazol-1-yl)methyl-1H-benzimidazol-4-yl]-2-methoxy-4-(2,3,4,5-tetrahydro-1H-1-benzazepin-1-yl) carbonylbenzamide was obtained in substantially the same manner as in Example 1.

$^1$H-NMR (300 MHz, DMSO-d$_6$, δ): 1.41(br, 1H), 1.81–1.98(m, 2H), 1.98–2.12(m, 1H), 2.67–2.82(m, 1H), 2.82–2.96(m, 1H), 3.01–3.16(m, 1H), 3.81(s, 3H), 4.77–4.88(m, 1H), 5.51(s, 2H), 6.79(d, J=8 Hz, 1H), 6.89–7.01(m, 4H), 7.06–7.25(m, 3H), 7.25–7.36(m, 2H), 7.84(s, 1H), 7.90(d, J=8 Hz, 1H), 8.13(d, J=8 Hz, 1H).

EXAMPLE 70

N-[2-(Imidazol-1-yl)methyl-1H-benzimidazol-4-yl]-2-methoxy-4-(2,3,4,5-tetrahydro-1H-1-benzazepin-1-yl) carbonylbenzamide dihydrochloride was obtained in substantially the same manner as in Example 10.

$^1$H-NMR (300 MHz, DMSO-d$_6$, δ): 1.43(br, 1H), 1.83–1.96(m, 2H), 1.96–2.13(m, 1H), 2.66–2.81(m, 1H), 2.81–2.97(m, 1H), 2.97–3.14(m, 1H), 3.77(s, 3H), 4.79–4.90(m, 1H), 5.83(s, 2H), 6.80(d, J=8 Hz, 1H), 6.86–7.02(m, 3H), 7.11(t, J=8 Hz, 1H), 7.20(t, J=8 Hz, 1H), 7.25–7.36(m, 2H), 7.78(s, 1H), 7.84(d, J=8 Hz, 1H), 7.91(s, 1H), 8.08(br, 1H).

PREPARATION 22

2-[4-(Dimethylamino)piperidin-1-yl)]-4-nitro-1H-benzimidazole was obtained in substantially the same manner as in Preparation 20.

$^1$H-NMR (300 MHz, DMSO-$d_6$, δ): 1.34–1.51(m, 2H), 1.79–1.90(m, 2H), 2.19(s, 6H), 2.31–2.43(m, 1H), 2.99–3.13(m, 2H), 4.21–4.35(m, 2H), 7.08(br, 1H), 7.52(br, 1H), 7.74(d, J=8 Hz, 1H).

PREPARATION 23

4-Amino-2-[4-(dimethylamino)piperidin-1-yl)]-1H-benzimidazole was obtained in substantially the same manner as in Preparation 19.

$^1$H-NMR (300 MHz, DMSO-$d_6$, δ): 1.32–1.50(m, 2H), 1.74–1.87(m, 2H), 2.19(s, 6H), 2.21–2.36(m, 1H), 2.81–2.97(m, 2H), 2.96–4.10(m, 2H), 6.21(d, J=8 Hz, 1H), 6.46(d, J=8 Hz, 1H), 6.63(t, J=8 Hz, 1H).

EXAMPLE 71

N-[2-[4-(Dimethylamino)piperidin-1-yl]-1H-benzimidazol-4-yl]-2-methoxy-4-(2,3,4,5-tetrahydro-1H-1-benzazepin-1-yl)carbonylbenzamide was obtained in substantially the same manner as in Example 1.

$^1$H-NMR (300 MHz, DMSO-$d_6$, δ): 1.35–1.55(m, 3H), 1.80–1.99(m, 4H), 1.99–2.12(m, 1H), 2.21(s, 6H), 2.30–2.43(m, 1H), 2.67–2.82(m, 1H), 2.82–2.96(m, 1H), 2.96–3.15(m, 3H), 3.93(s, 3H), 4.10–4.25(m, 2H), 4.79–4.90(m, 1H), 6.77–7.05(m, 6H), 7.11(t, J=8 Hz, 1H), 7.32(d, J=8 Hz, 1H), 7.91(d, J=8 Hz, 1H), 8.00(d, J=8 Hz, 1H).

EXAMPLE 72

N-[2-[4-(Dimethylamino)piperidin-1-yl]-1H-benzimidazol-4-yl]-2-methoxy-4-(2,3,4,5-tetrahydro-1H-1-benzazepin-1-yl)carbonylbenzamide dihydrochloride was obtained in substantially the same manner as in Example 10.

$^1$H-NMR (300 MHz, DMSO-$d_6$, δ): 1.43(br, 1H), 1.71–2.00(m, 4H), 2.00–2.13(m, 1H), 2.13–2.30(m, 2H), 2.67–2.84(m, 7H), 2.84–2.98(m, 1H), 2.98–3.14(m, 1H), 3.20–3.64(m, 3H), 3.72(s, 3H), 4.23–4.40(m, 2H), 4.78–4.90(m, 1H), 6.76–6.89(m, 2H), 6.93(s, 1H), 7.00(t, J=8 Hz, 1H), 7.13(d, J=8 Hz, 1H), 7.20(br, 2H), 7.32(d, J=8 Hz, 1H), 7.54(br, 1H), 7.72(br, 1H).

EXAMPLE 73

N-[2-(N,N-Dimethylcarbamoyl)-1H-benzimidazol-4-yl]-2-methoxy-4-(2,3,4,5-tetrahydro-1H-1-benzazepin-1-yl)carbonylbenzamide was obtained in substantially the same manner as in Example 1.

$^1$H-NMR (300 MHz, DMSO-$d_6$, δ): 1.42(br, 1H), 1.90(br, 2H), 1.99–2.12(m, 1H), 2.68–2.81(m, 1H), 2.83–2.95(m, 1H), 3.00–3.16(m, 4H), 3.73(s, 3H), 3.92(s, 3H), 4.79–4.89 (m, 1H), 6.81(d, J=8 Hz, 1H), 6.86–7.00(m, 2H), 7.04(s, 1H), 7.11(t, J=8 Hz, 1H), 7.20–7.35(m, 3H), 7.86–7.96(m, 1H), 8.20–8.30(m, 1H).

EXAMPLE 74

N-[1-(tert-Butoxycarbony)-2-[N-[2-(tert-butoxycarbonyamino)ethyl]-N-methylamino]-1H-benzimidazol-4-yl]-2-methoxy-4-(2,3,4,5-tetrahydro-1H-1-benzazepin-1-yl)carbonylbenzamide was obtained in substantially the same manner as in Example 1.

$^1$H-NMR (300 MHz, CDCl$_3$, δ): 1.40(br, 1H), 1.59(s, 9H), 1.69(s, 9H), 2.00(br, 2H), 2.04–2.20(m, 1H), 2.76–2.98(m, 2H), 3.00–3.14(m, 4H), 3.42–3.52(m, 2H), 3.60–3.71(m, 2H), 3.95(s, 3H), 4.97–5.07(m, 1H), 5.47(br, 1H), 6.65(d, J=8 Hz, 1H), 6.84(d, J=8 Hz, 1H), 6.92(t, J=8 Hz, 1H), 6.98(s, 1H), 7.08–7.16(m, 2H), 7.22–7.30(m, 1H), 7.39(d, J=8 Hz, 1H), 8.08(d, J=8 Hz, 1H), 8.41(d, J=8 Hz, 1H).

EXAMPLE 75

N-[2-[N-(2-Aminoethyl)-N-methylamino]-1H-benzimidazol-4-yl]-2-methoxy-4-(2,3,4,5-tetrahydro-1H-1-benzazepin-1-yl)carbonylbenzamide was obtained in substantially the same manner as in Example 2.

$^1$H-NMR (300 MHz, CDCl$_3$, δ): 1.43–1.63(m, 1H), 1.91–2.20(m, 3H), 2.75–2.97(m, 2H), 2.97–3.13(m, 3H), 3.20(s, 3H), 3.51(t-like, 2H), 3.92(s, 3H), 4.96–5.07(m, 1H), 6.55(d, J=8 Hz, 1H), 6.83(d, J=8 Hz, 1H), 6.89–7.03(m, 3H), 7.03–7.15(m, 2H), 7.21–7.29(m, 2H), 8.03(d, J=8 Hz, 1H).

EXAMPLE 76

N-[2-[N-(2-Aminoethyl)-N-methylamino]-1H-benzimidazol-4-yl]-2-methoxy-4-(2,3,4,5-tetrahydro-1H-1-benzazepin-1-yl)carbonylbenzamide dihydrochloride was obtained in substantially the same manner as in Example 10.

$^1$H-NMR (300 MHz, DMSO-$d_6$, δ): 1.43(br, 1H), 1.80–1.97(m, 2H), 1.97–2.12(m, 1H), 2.65–2.80(m, 1H), 2.83–2.95(m, 1H), 2.98–3.11(m, 1H), 3.13–3.30(m, 5H), 3.71(br 3H), 3.90(br 2H), 4.77–4.89(m, 1H), 6.81(d-like, 2H), 6.94(s, 1H), 6.98(t, J=8 Hz, 1H), 7.07–7.27(m, 3H), 7.31(d, J=8 Hz, 1H), 7.51(br, 1H), 7.76(br, 1H), 8.22(br, 3H).

PREPARATION 24

Methyl 4-(6,7,8,9-tetrahydro-5H-pyrido[2,3-b]azepin-9-yl)carbonyl-2-metoxybenzoate was obtained in substantially the same manner as in Preparation 1.

$^1$H-NMR (300 MHz, CDCl$_3$, δ): 1.70–2.04(m, 4H), 2.86–2.99(m, 2H), 3.77(s, 3H), 3.82(s, 3H), 6.61(d, J=8 Hz, 1H), 6.97–7.07(m, 2H), 7.46–7.61(m, 2H), 7.99(m, 1H).

PREPARATION 25

4-(6,7,8,9-Tetrahydro-5H-pyrido[2,3-b]azepin-9-yl)carbonyl-2-metoxybenzoic acid was obtained in substantially the same manner as in Preparation 2.

$^1$H-NMR (300 MHz, CDCl$_3$, δ): 1.73–1.92(m, 2H), 1.93–2.07(m, 2H), 2.89–3.01(m, 2H), 4.02(s, 3H), 6.55(d, J=8 Hz, 1H), 7.06(m, 1H), 7.29(s, 1H), 7.59(d, J=8 Hz, 1H), 7.81(d, J=8 Hz, 1H), 7.98(m, 1H).

EXAMPLE 77

2-Methoxy-N-(2-methyl-1H-benzimidazol-4-yl)-4-(6,7,8,9-tetrahydro-5H-pyrido[2,3-b]azepin-9-yl)carbonylbenzamide was obtained in substantially the same manner as in Example 1.

$^1$H-NMR (300 MHz, CDCl$_3$, δ): 1.65–2.09(m, 4H), 2.60(s, 3H), 2.92–3.03(m, 2H), 4.04(s, 3H), 6.62(d, J=8 Hz, 1H), 7.04(m, 1H), 7.15(dd, J=8, 8 Hz, 1H), 7.21–7.30(m, 3H), 7.59(d, J=8 Hz, 1H), 7.92–8.03(m, 2H).

EXAMPLE 78

2-Methoxy-N-(2-methyl-1H-benzimidazol-4-yl)-4-(6,7,8,9-tetrahydro-5H-pyrido[2,3-b]azepin-9-yl)

carbonylbenzamide dihydrochloride was obtained in substantially the same manner as in Example 10.

$^1$H-NMR (300 MHz, DMSO-d$_6$, δ): 1.64–1.98(m, 4H), 2.80(s, 3H), 2.96–3.08(m, 2H), 3.74(s, 3H), 4.35–4.72(br, 2H), 6.85(d, J=8 Hz, 1H), 6.96(s, 1H), 7.22(m, 1H), 7.48(dd, J=8, 8 Hz, 1H), 7.52–7.65(m, 3H), 7.84(d, J=8 Hz, 1H), 8.03(m, 1H).

PREPARATION 26

A solution of methyl 4-(5-oxo-2,3,4,5-tetrahydro-1H-1-benzazepin-1-yl)carbonyl-2-methoxybenzoate (200 mg) and copper bromide (291 mg) in chloroform (10 ml) and ethyl acetate (1 ml) was gently refluxed under heating for 2 hours. After cooling, the reaction mixture was diluted with ethyl acetate and washed successively with 1N hydrochloric acid, saturated aqueous sodium hydrogencarbonate solution and brine. Evaporation of the dried (Mg$_2$SO$_4$) organic layer gave methyl 4-(4-bromo-5-oxo-2,3,4,5-tetrahydro-1H-1-benzazepin-1-yl)carbonyl-2-methoxybenzoate (245 mg).

$^1$H-NMR (300 MHz, CDCl$_3$, δ): 2.39–3.14(br, 2H), 3.68 (s, 3H), 3.83(s, 3H), 4.92(m, 1H), 6.59–6.92(m, 3H), 7.18–7.39(m, 2H), 7.60(m, 1H), 7.69(m, 1H).

PREPARATION 27

To a suspension of methyl 4-(4-bromo-5-oxo-2,3,4,5-tetrahydro-1H-1-benzazepin-1-yl)carbonyl-2-methoxybenzoate (240 mg) and potassium carbonate (767 mg) in acetonitrile (8 ml) was added acetamidine hydrochloride (472 mg) and the mixture was heated at 90° C. for 3 hours. After cooling, the reaction mixture was diluted with chloroform and washed with water. The organic layer was dried over sodium sulfate and the solvent was evaporated in vacuo. The residue was purified by column chromatography (SiO$_2$; 30 g, ethyl acetate) to give methyl 4-(2-methyl-1,4,5,6-tetrahydro-imidazo[4,5-d][1]benzazepin-6-yl)carbonyl-2-methoxybenzoate (95 mg).

$^1$H-NMR (300 MHz, CDCl$_3$, δ): 2.45(s, 3H), 2.93(brd, J=17 Hz, 1H), 3.10(m, 1H), 3.45(m, 1H), 3.59(s, 3H), 3.82(s, 3H), 5.08(m, 1H), 6.64(d, J=8 Hz, 1H), 6.68–6.76(m, 2H), 6.87(dd, J=8, 8 Hz, 1H), 7.20(dd, J=8, 8 Hz, 1H), 7.51(d, J=8 Hz, 1H), 8.12(br, 1H).

PREPARATION 28

A solution of methyl 4-(2-methyl-1,4,5,6-tetrahydro-imidazo[4,5-d][1]benzazepin-6-yl)carbonyl-2-methoxybenzoate (95 mg) in dichloromethane (10 ml) was treated with triethylamine (49 mg), N,N-dimethylaminopyridine (catalytic amount) and di-tert-butyl dicarbonate (79.5 mg). The resulting solution was stirred for 20 hours at room temperature and concentrated in vacuo. The residue was purified by preparative thin-layer chromatography (ethyl acetate/hexane=1/1) to give methyl 4-[1-(tert-butoxycarbonyl)-2-methyl-1,4,5,6-tetrahydro-imidazo[4,5-d][1]benzazepin-6-yl]carbonyl-2-methoxybenzoate (70 mg).

$^1$H-NMR (300 MHz, CDCl$_3$, δ): 1.66(s, 9H), 2.96–3.10 (m, 1H), 3.22(brd, J=17 Hz, 1H), 3.52–3.69(m, 4H), 3.83(s, 3H), 5.09–5.20(m, 1H), 6.62(d, J=8 Hz, 1H), 6.70(d, J=8 Hz, 1H), 6.76(s, 1H), 6.92(dd, J=8, 8 Hz, 1H), 7.24(dd, J=8, 8 Hz, 1H), 7.50(d, J=8 Hz, 1H), 8.30(d, J=8 Hz, 1H).

PREPARATION 29

4-(2-Methyl-1,4,5,6-tetrahydro-imidazo[4,5-d][1]benzazepin-6-yl)-carbonyl-2-methoxybenzoic acid was obtained in substantially the same manner as in Preparation 2.

MS (ES+): 378 (M+H)

EXAMPLE 79

2-Methoxy-N-(2-methyl-1H-benzimidazol-4-yl)-4-(2-methyl-1,4,5,6-tetrahydro-imidazo[4,5-d][1]benzazepin-6-yl)carbonylbenzamide was obtained in substantially the same manner as in Example 1.

$^1$H-NMR (300 MHz, CDCl$_3$, δ): 2.46(s, 3H), 2.52(s, 3H), 2.97(brd, J=17 Hz, 1H), 3.06–3.20(m, 1H), 3.32(s, 3H), 3.42–3.58(m, 1H), 4.18–4.40(br, 1H), 5.06–5.17(m, 1H), 6.06(d, J=8 Hz, 1H), 6.51(d, J=8 Hz, 1H), 6.67–6.76(m, 2H), 6.77–6.90(m, 2H), 6.95(dd, J=8, 8 Hz, 1H), 7.18–7.29(m, 2H).

EXAMPLE 80

2-Methoxy-N-(2-methyl-1H-benzimidazol-4-yl)-4-(2-methyl-1,4,5,6-tetrahydro-imidazo[4,5-d][1]benzazepin-6-yl)carbonylbenzamide dihydrochloride was obtained in substantially the same manner as in Example 10.

$^1$H-NMR (300 MHz, DMSO-d$_6$, δ): 2.30(s, 3H), 2.66 and 2.67(s, total 3H), 3.00–3.23(m, 2H), 3.26–3.59(m, 4H), 4.88–5.03(m, 1H), 6.45–6.87(m, 3H), 6.89–7.01(m, 1H), 7.02–7.28(m, 3H), 7.32–7.49(m, 2H), 8.03–8.13(m, 1H).

PREPARATION 30

Methyl 4-(2,3-dimethyl-4-oxo-5,6,7,8-tetrahydro-4H-thieno[2,3-b]azepin-8-yl)carbonyl-2-methoxybenzoate was obtained in substantially the same manner as in Preparation 1.

$^1$H-NMR (300 MHz, CDCl$_3$, δ): 2.07–2.25(m, 8H), 2.72–2.83(m, 2H), 3.80(s, 3H), 3.88(s, 3H), 3.91–4.07(m, 2H), 6.90–7.02(m, 2H), 7.70(d, J=8 Hz, 1H).

PREPARATION 31

Methyl 4-(2,3-dimethyl-4-hydroxy-5,6,7,8-tetrahydro-4H-thieno[2,3-b]azepin-8-yl)carbonyl-2-methoxybenzoate was obtained in substantially the same manner as in Example 6.

$^1$H-NMR (300 MHz, CDCl$_3$, δ): 1.73–2.46(m, 10H), 3.03–3.27(br, 1H), 3.76(s, 3H), 3.86(s, 3H), 4.59–4.82(br, 1H), 4.92–5.01(m, 1H), 7.14(d, J=8 Hz, 1H), 7.26(s, 1H), 7.70(d, J=8 Hz, 1H).

PREPARATION 32

A solution of sodium iodide (462 mg), chlorotrimethylsilane (335 mg) and acetonitrile (0.2 ml) in hexane (0.5 ml) was cooled to 0° C. To the solution was added methyl 4-(2,3-dimethyl-4-hydroxy-5,6,7,8-tetrahydro-4H-thieno[2,3-b]azepin-8-yl)carbonyl-2-methoxybenzoate (200 mg) in acetonitrile (1.0 ml). The mixture was stirred at room temperature for 5 hours. The reaction mixture was diluted with ethyl acetate and washed with aqueous sodium hydrogencarbonate solution. The organic layer was dried over magnesium sulfate. After evaporation of the solvent, the residue was purified by silica gel column chromatography (SiO$_2$; 30 g, CHCl$_3$) to give methyl 4-(2,3-dimethyl-5,6,7,8-tetrahydro-4H-thieno[2,3-b]azepin-8-yl)carbonyl-2-methoxybenzoate (150 mg).

$^1$H-NMR (300 MHz, CDCl$_3$, δ): 1.61–1.79(m, 2H), 1.90–2.06(m, 5H), 2.12(s, 3H), 2.60–2.73(m, 2H), 3.67–4.06(m, 8H), 6.90(d, J=8 Hz, 1H), 6.98(s, 1H), 7.65(d, J=8 Hz, 1H).

PREPARATION 33

4-(2,3-Dimethyl-5,6,7,8-tetrahydro-4H-thieno[2,3-b]azepin-8-yl)carbonyl-2-methoxybenzoic acid was obtained in substantially the same manner as in Preparation 2.

¹H-NMR (300 MHz, CDCl₃, δ): 1.60–1.82(m, 2H), 1.93–2.10(m, 5H), 2.14(s, 3H), 2.62–2.76(m, 2H), 3.66–4.25(m, 2H), 4.01(s, 3H), 6.96(d, J=8 Hz, 1H), 7.16(s, 1H), 7.98(d, J=8 Hz, 1H).

EXAMPLE 81

N-[1-(tert-Butoxycarbonyl)-2-methyl-1H-benzimidazol-4-yl]-4-(2,3-dimethyl-5,6,7,8-tetrahydro-4H-thieno[2,3-b]azepin-8-yl)carbonyl-2-methoxybenzamide was obtained in substantially the same manner as in Example 1.

¹H-NMR (300 MHz, CDCl₃, δ): 1.66–1.79(m, 11H), 1.94–2.08(m, 5H), 2.13(s, 3H), 2.65–2.77(m, 2H), 2.83(s, 3H), 4.10(s, 3H), 7.00(brd, J=8 Hz, 1H), 7.14(s, 1H), 7.29 (dd, J=8, 8 Hz, 1H), 7.58(d, J=8 Hz, 1H), 8.15(brd, J=8 Hz, 1H), 8.43(d, J=8 Hz, 1H).

EXAMPLE 82

4-(2,3-Dimethyl-5,6,7,8-tetrahydro-4H-thieno[2,3-b]azepin-8-yl)carbonyl-2-methoxy-N-(2-methyl-1H-benzimidazol-4-yl)benzamide was obtained in substantially the same manner as in Example 2.

¹H-NMR (300 MHz, DMSO-d₆, δ): 1.56–1.73(m, 2H), 1.83–2.02(m, 5H), 2.10(brs, 3H), 2.54(s, 3H), 2.64–2.81(m, 2H), 3.52–3.89(m, 2H), 4.02(brs, 3H), 7.00–7.25(m, 5H), 8.00(m, 1H), 8.10(d, J=8 Hz, 1H).

PREPARATION 34

A solution of 1-acetyl-5-methyl-2,3,4,5-tetrahydro-1H-pyrido[2,3-b][1,4]diazepine (1.7 g) in 6N hydrochloric acid (60 ml) was heated at 100° C. for 6 hours. After cooling, the mixture was basified with aqueous sodium hydroxide and extracted with ethyl acetate. The extracted organic layer was washed with brine and dried over sodium sulfate and concentrated in vacuo. The residue was washed with hexane to give 5-methyl-2,3,4,5-tetrahydro-1H-pyrido[2,3-b][1,4]diazepine (1.3 g).

¹H-NMR (300 MHz, CDCl₃, δ): 1.83–1.96(m, 2H), 3.05 (s, 3H), 3.16–3.25(m, 2H), 3.25–3.32(m, 2H), 6.58(m, 1H), 6.82(d, J=8 Hz, 1H), 7.81(d, J=2 Hz, 1H).

PREPARATION 35

Methyl 4-(5-methyl-2,3,4,5-tetrahydro-1H-pyrido[2,3-b](1,4]diazepin-1-yl)carbonyl-2-methoxybenzoate was obtained in substantially the same manner as in Preparation 1.

¹H-NMR (300 MHz, CDCl₃, δ): 2.00–2.24(br, 2H), 3.13 (s, 3H), 3.13–3.34(br, 2H), 3.70(s, 3H), 3.73–3.87(m, 1H), 3.83(s, 3H), 4.56–4.76(br, 1H), 6.39(m, 1H), 6.75(d, J=8 Hz, 1H), 6.80(s, 1H), 6.89(d, J=8 Hz, 1H), 7.61(d, J=8 Hz, 1H), 8.02(d, J=3 Hz, 1H).

PREPARATION 36

4-(5-Methyl-2,3,4,5-tetrahydro-1H-pyrido[2,3-b][i,4]diazepin-1-yl)carbonyl-2-methoxybenzoic acid was obtained in substantially the same manner as in Preparation 2.

¹H-NMR (300 MHz, CDCl₃, δ): 2.00–2.25(br, 2H), 3.03–3.36(m, 5H), 3.69–3.92(m, 4H), 4.56–4.77(br, 1H), 6.39(m, 1H), 6.76(d, J=8 Hz, 1H), 6.89(s, 1H), 6.99(d, J=8 Hz, 1H), 7.97(d, J=8 Hz, 1H), 8.06(d, J=3 Hz, 1H).

EXAMPLE 83

N-[1-(tert-Butoxycarbonyl)-2-methyl-1H-benzimidazol-4-yl]-2-methoxy-4-(5-methyl-2,3,4,5-tetrahydro-1H-pyrido[2,3-b][1,4]diazepin-1-yl)carbonylbenzamide was obtained in substantially the same manner as in Example 1.

¹H-NMR (300 MHz, CDCl₃, δ): 1.72(s, 9H), 2.03–2.27 (br, 2H), 2.82(s, 3H), 3.17(s, 3H), 3.18–3.38(br, 2H), 3.73–3.94(br, 1H), 3.97(s, 3H), 4.59–4.80(br, 1H), 6.39(m, 1H), 6.78(d, J=8 Hz, 1H), 6.90(s, 1H), 7.03(d, J=8 Hz, 1H), 7.29(dd, J=8, 8 Hz, 1H), 7.57(d, J=8 Hz, 1H), 8.04(m, 1H), 8.14(d, J=8 Hz, 1H), 8.41(d, J=8 Hz, 1H).

EXAMPLE 84

2-Methoxy-N-(2-methyl-1H-benzimidazol-4-yl)-4-(5-methyl-2,3,4,5-tetrahydro-1H-pyrido[2,3-b][1,4]diazepin-1-yl)carbonylbenzamide was obtained in substantially the same manner as in Example 2.

¹H-NMR (300 MHz, CDCl₃, δ): 2.02–2.26(br, 2H), 2.61 (s, 3H), 3.16(s, 3H), 3.19–3.40(br, 2H), 3.70–4.00(m, 4H), 4.57–4.80(br, 1H), 6.40(m, 1H), 6.70–6.82(m, 2H) 6.84–6.95(br, 1H), 7.05(d, J=8 Hz, 1H), 7.09–7.22(m, 1H), 7.44–7.58(br, 1H), 8.06(m, 1H), 8.12(d, J=8 Hz, 1H).

EXAMPLE 85

2-Methoxy-N-(2-methyl-1H-benzimidazol-4-yl)-4-(5-methyl-2,3,4,5-tetrahydro-1H-pyrido[2,3-b][1,4]diazepin-1-yl)carbonylbenzamide trihydrochloride was obtained in substantially the same manner as in Example 10.

¹H-NMR (300 MHz, DMSO-d₆, δ): 2.08–2.29(br, 21H), 2.79(s, 3H), 3.33(s, 3H), 3.38–3.58(br, 2H), 3.83(brs, 3H), 4.08–4.27(br, 1H), 4.37–4.59(br, 1H), 6.63–6.79(br, 1H), 6.90–7.02(br, 1H), 7.08–7.20(br, 1H), 7.41–7.69(m, 4H), 7.69–7.80(br, 1H), 7.84–7.97(br, 1H).

PREPARATION 37

Methyl 4-(5,6,7,8-tetrahydro-4H-thieno[3,2-b]azepin-4-yl)carbonyl-2-methoxybenzoate was obtained in substantially the same manner as in Preparation 1.

¹H-NMR (300 MHz, CDCl₃, δ): 1.73–1.88(m, 2H), 1.97–2.12(m, 2H), 2.87–2.99(m, 2H), 3.76(s, 3H), 3.86(s, 3H), 3.70–4.06(br, 2H), 6.17(d, J=3 Hz, 1H), 6.65(d, J=3 Hz, 1H), 6.85(d, J=8 Hz, 1H), 6.90(s, 1H), 7.62(d, J=8 Hz, 1H).

PREPARATION 38

4-(5,6,7,8-Tetrahydro-4H-thieno[3,2-b]azepin-4-yl) carbonyl-2-methoxybenzoic acid was obtained in substantially the same manner as in Preparation 2.

¹H-NMR (300 MHz, CDCl₃, δ): 1.73–1.90(m, 2H), 1.97–2.12(m, 2H), 2.89–3.00(m, 2H), 3.72–4.18(br, 1H), 3.96(s, 3H), 6.17(d, J=3 Hz, 1H), 6.68(d, J=3 Hz, 1H), 6.92(d, J=8 Hz, 1H), 7.04(s, 3H), 7.97(d, J=8 Hz, 1H).

EXAMPLE 86

N-[1-(tert-Butoxycarbonyl)-2-methyl-1H-benzimidazol-4-yl]-2-methoxy-4-(5,6,7,8-tetrahydro-4H-thieno[3,2-b]azepin-4-yl)carbonylbenzamide was obtained in substantially the same manner as in Example 1.

¹H-NMR (300 MHz, CDCl₃, δ): 1.72(s, 9H), 1.75–1.88 (m, 2H), 2.00–2.12(m, 2H), 2.82(s, 3H), 2.91–3.00(m, 2H), 4.05(s, 3H), 6.19(d, J=3 Hz, 1H), 6.66(d, J=3 Hz, 1H), 6.97(d, J=8 Hz, 1H), 7.03(s, 1H), 7.29(dd, J=8, 8 Hz, 1H), 7.58(d, J=8 Hz, 1H), 8.14(d, J=8 Hz, 1H), 8.41(d, J=8 Hz, 1H).

EXAMPLE 87

2-Methoxy-N-(2-methyl-1H-benzimidazol-4-yl)-4-(5,6,7,8-tetrahydro-4H-thieno[3,2-b)azepin-4-yl)

carbonylbenzamide was obtained in substantially the same manner as in Example 2.

$^1$H-NMR (300 MHz, CDCl$_3$, δ): 1.76–1.89(m, 2H), 2.00–2.13(m, 2H), 2.60(s, 3H), 2.91–3.02(m, 2H), 3.71–4.21(m, 5H), 6.20(d, J=3 Hz, 1H), 6.68(d, J=3 Hz, 1H), 6.70–6.89(br, 1H), 6.93–7.07(m, 2H), 7.16(dd, J=8, 8 Hz, 1H), 7.37–7.61(br, 1H), 8.12(d, J=8 Hz, 1H).

PREPARATION 39

Methyl 4-(3,3-dimethylindolin-1-yl)carbonyl-2-methoxybenzoate was obtained in substantially the same manner as in Preparation 1.

$^1$H-NMR (300 MHz, CDCl$_3$, δ): 1.33(s, 6H), 3.63–3.90 (br, 2H), 3.92(s, 3H), 3.93(s, 3H), 7.00–7.36(m, 7H), 7.84(d, J=8 Hz, 1H).

PREPARATION 40

4-(3,3-Dimethylindolin-1-yl)carbonyl-2-methoxybenzoic acid was obtained in substantially the same manner as in Preparation 2.

$^1$H-NMR (300 MHz, CDCl$_3$, δ): 1.34(brs, 6H), 3.63–3.97 (br, 2H), 4.11(s, 3H), 7.00–7.44(m, 5H), 8.10–8.36(m, 2H).

EXAMPLE 88

N-[1-(tert-Butoxycarbonyl)-2-methyl-1H-benzimidazol-4-yl]-4-(3,3-dimethylindolin-1-yl)carbonyl-2-methoxybenzamide was obtained in substantially the same manner as in Example 1.

$^1$H-NMR (300 MHz, CDCl$_3$, δ): 1.34(brs, 6H), 1.72(s, 9H), 2.85(s, 3H), 3.72–3.97(br, 2H), 4.22(s, 3H), 7.00–7.38 (m, 7H), 7.61(d, J=8 Hz, 1H), 8.40(d, J=8 Hz, 1H), 8.47(d, J=8 Hz, 1H).

EXAMPLE 89

4-(3,3-Dimethylindolin-1-yl)carbonyl-2-methoxy-N-(2-methyl-1H-benzimidazol-4-yl)benzamide was obtained in substantially the same manner as in Example 2.

$^1$H-NMR (300 MHz, DMSO-d$_6$, δ): 1.26(s, 6H), 2.53(s, 3H), 3.80(s, 2H), 4.18(s, 3H), 7.04–7.44(m, 6H), 7.50(s, 1H), 8.00–8.32(m, 3H).

PREPARATION 41 tert-Butyl 2-methoxy-4-(3-methyl-4-oxo-2,3,4,5-tetrahydro-1H-1,3-benzodiazepin-1-yl)carbonylbenzoate was obtained in substantially the same manner as in Preparation 1.

$^1$H-NMR (300 MHz, CDCl$_3$, δ): 1.56(s, 9H), 3.11(s, 3H), 3.72(s, 3H), 4.10(s, 2H), 5.36(s, 2H), 6.64(d, J=8 Hz, 1H), 6.78(d, J=8 Hz, 1H), 6.89(s, 1H), 6.98(dd, J=8, 8 Hz, 1H), 7.13(dd, J=8, 8 Hz, 1H), 7.23(d, J=8 Hz, 1H), 7.53(d, J=8 Hz, 1H).

PREPARATION 42

2-Methoxy-4-(3-methyl-4-oxo-2,3,4,5-tetrahydro-1H-1,3-benzodiazepin-1-yl)carbonylbenzoic acid was obtained in substantially the same manner as in Example 2.

$^1$H-NMR (300 MHz, CDCl$_3$, δ): 3.16(s, 3H), 3.90(s, 3H), 4.18(s, 2H), 5.42(s, 2H), 6.63(d, J=8 Hz, 1H), 6.94(d, J=8 Hz, 1H), 6.97–7.07(m, 2H), 7.20(dd, J=8, 8 Hz, 1H), 7.29(d, J=8 Hz, 1H), 7.98(d, J=8 Hz, 1H).

EXAMPLE 90

N-[1-(tert-Butoxycarbonyl)-2-methyl-1H-benzimidazol-4-yl]-2-methoxy-4-(3-methyl-4-oxo-2,3,4,5-tetrahydro-1H-1,3-benzodiazepin-1-yl)carbonylbenzamide was obtained in substantially the same manner as in Example 1.

$^1$H-NMR (300 MHz, CDCl$_3$, δ): 1.72(s, 9H), 2.83(s, 3H), 3.14(s, 3H), 4.00(s, 3H), 4.13(s, 2H), 5.41(s, 2H), 6.65(d, J=8 Hz, 1H), 6.92–7.03(m, 3H), 7.14(dd, J=8, 8 Hz, 1H), 7.22–7.33(m, 2H), 7.58(d, J=8 Hz, 1H), 8.16(d, J=8 Hz, 1H), 8.41(d, J=8 Hz, 1H).

EXAMPLE 91

2-Methoxy-N-(2-methyl-1H-benzimidazol-4-yl)-4-(3-methyl-4-oxo-2,3,4,5-tetrahydro-1H-1,3-benzodiazepin-1-yl)carbonylbenzamide was obtained in substantially the same manner as in Example 2.

$^1$H-NMR (300 MHz, CDCl$_3$, δ): 2.63(s, 3H), 3.14(brs, 3H), 3.92 and 3.98(s, total 3H), 4.11–4.17(m, 2H), 5.36–5.37(m, 2H), 6.64(d, J=8 Hz, 1H), 6.71–7.60(m, 7H), 8.09–8.21(m, 1H), 8.32 and 9.26(m, Total 1H).

EXAMPLE 92

2-Methoxy-N-(2-methyl-1H-benzimidazol-4-yl)-4-(3-methyl-4-oxo-2,3,4,5-tetrahydro-1H-1,3-benzodiazepin-1-yl)carbonylbenzamide hydrochloride was obtained in substantially the same manner as in Example 10.

$^1$H-NMR (300 MHz, DMSO-d$_6$, δ): 2.79(s, 3H), 2.93(s, 3H), 3.78(s, 3H), 4.12(s, 2H), 5.40(s, 2H), 6.84–6.96(m, 2H), 7.04(dd, J=8, 8 Hz, 1H), 7.10–7.21(m, 2H), 7.33(d, J=8 Hz, 1H), 7.47(dd, J=8, 8 Hz, 1H), 7.56(d, J=8 Hz, 1H), 7.60–7.72(m, 2H).

PREPARATION 43

Methyl 4-(5,6-dihydro-pyrido(2,3-b)[1,5]benzoxazepin-6-yl)carbonyl-2-methoxybenzoate was obtained in substantially the same manner as in Preparation 1.

$^1$H-NMR (300 MHz, CDCl$_3$, δ): 3.71(s, 3H), 3.83(s, 3H), 6.77(m, 1H), 6.86–6.97(m, 2H), 7.00(d, J=8 Hz, 1H), 7.12 (m, 1H), 7.24(dd, J=8, 8 Hz, 1H), 7.43(d, J=8 Hz, 1H), 7.58–7.71(m, 2H), 8.28(m, 1H).

PREPARATION 44

4-(5,6-Dihydro-pyrido[2,3-b][1,5]benzoxazepin-6-yl) carbonyl-2-methoxybenzoic acid was obtained in substantially the same manner as in Preparation 2.

$^1$H-NMR (300 MHz, CDCl$_3$, δ): 3.87(s, 3H), 6.78(d, J=8 Hz, 1H), 6.96(dd, J=8, 8 Hz, 1H), 7.02(s, 1H), 7.10–7.20(m, 2H), 7.27(dd, J=8, 8 Hz, 1H), 7.46(d, J=8 Hz, 1H), 7.67(d, J=8 Hz, 1H), 8.00(d, J=8 Hz, 1H), 8.32(m, 1H).

EXAMPLE 93

N-(1-(tert-Butoxycarbonyl)-2-methyl-1H-benzimidazol-4-yl]-4-(5,6-dihydropyrido[2,3-b][1,5]benzoxazepin-6-yl) carbonyl-2-methoxybenzamide was obtained in substantially the same manner as in Example 1.

$^1$H-NMR (300 MHz, CDCl$_3$, δ): 1.72(s, 9H), 2.82(s, 3H), 3.98(s, 3H), 6.80(brd, J=8 Hz, 1H), 6.93(dd, J=8, 8 Hz, 1H), 7.00(s, 1H), 7.10–7.33(m, 5H), 7.47(d, J=8 Hz, 1H), 7.57(d, J=8 Hz, 1H), 7.66(brd, J=8 Hz, 1H), 8.20(d, J=8 Hz, 1H), 8.30(d, J=3 Hz, 1H), 8.40(d, J=8 Hz, 1H).

EXAMPLE 94

4-(5,6-Dihydro-pyrido[2,3-b][1,5]benzoxazepin-6-yl) carbonyl-2-methoxy-N-(2-methyl-1H-benzimidazol-4-yl) benzamide was obtained in substantially the same manner as in Example 2.

¹H-NMR (300 MHz, CDCl₃, δ): 2.62(s, 3H), 3.85–4.01 (m, 3H), 6.67–7.33(m, 8H), 7.41–7.73(m, 3H), 8.17(m, 1H), 8.32(d, J=3 Hz, 1H).

EXAMPLE 95

4-(5, 6-Dihydro-pyrido [2,3-b][1,5]benzoxazepin-6-yl) carbonyl-2-methoxy-N-(2-methyl-1H-benzimidazol-4-yl) benzamide dihydrochloride was obtained in substantially the same manner as in Example 10.

¹H-NMR (300 MHz, CDCl₃, δ): 2.80(s, 3H), 3.80(s, 3H), 6.96(d, J=8 Hz, 1H), 7.03–7.23(m, 3H), 7.24–7.53(m, 4H), 7.54–7.71(m, 3H), 7.92(m, 1H), 8.28(d, J=4 Hz, 1H).

PREPARATION 45

To a solution of 5,6,7,8-tetrahydro-8-oxo-isoquinoline (850 mg) in pyridine (10 ml) was added hydroxylamine hydrochloride (803 mg), and the mixture was stirred at room temperature for 15 hours. The reaction mixture was concentrated in vacuo, and the residue was dissolved in ethyl acetate and washed with saturated aqueous sodium hydrogen-carbonate solution and brine. Evaporation of the dried (Na₂SO₄) organic layer gave 8-hydroxyimino-5,6,7,8-tetrahydroisoquinoline (970 mg).

¹H-NMR (300 MHz, CDCl₃, δ): 1.83–1.96(m, 2H), 2.71–2.89(m, 4H), 7.11(d, J=5 Hz, 1H), 8.35(d, J=5 Hz, 1H), 9.22(s, 1H).

PREPARATION 46

To a solution of 8-hydroxyimino-5,6,7,8-tetrahydroisoquinoline (960 mg) and p-toluenesulfonyl chloride (1.69 g) in acetone was added 1N sodium hydroxide (8.88 ml) and the mixture was heated at 55° C. for 2 hours. The acetone was evaporated and the aqueous reaction mixture was extracted with ethyl acetate. The extract was washed with brine and dried over sodium sulfate and concentrated in vacuo to give 8-(4-methylphenylsulfonyl) oxyimino-5,6,7,8-tetrahydroisoquinoline (1.25 g).

¹H-NMR (300 MHz, CDCl₃, δ): 1.80–1.96(m, 2H), 2.45 (s, 3H), 2.67–2.80(m, 2H), 2.81–2.92(m, 2H), 7.09(d, J=5 Hz, 1H), 7.37(d, J=8 Hz, 2H), 7.96(d, J=8 Hz, 2H), 8.47(d, J=5 Hz, 1H), 9.02(s, 1H).

PREPARATION 47

A solution of 8-(4-methylphenylsulfonyl)oxyimino-5,6,7,8-tetrahydroisoquinoline (1.2 g) and potassium acetate (7.45 g) in ethanol (25 ml) and water (30 ml) was heated at 95° C. for 23 hours. The solvent was evaporated at reduced pressure, and the residue was basified with saturated aqueous sodium hydrogencarbonate solution and extracted with chloroform. The dried extract (dried over sodium sulfate) was evaporated at reduced pressure to give crude product. After partial purification by column chromatography (SiO₂; 30 g, AcOEt/hexane=2/1, then 5% MeOH—CHCl₃), the obtained solid was washed with ether to give 2,3,4,5-tetrahydro-1H-pyrido[3,4-b]azepin-2-one (170 mg).

¹H-NMR (300 MHz, CDCl₃, δ): 2.22–2.36(m, 2H), 2.41 (t, J=7 Hz, 2H), 2.86(t, J=7 Hz, 2H), 7.19(d, J=5 Hz, 1H), 8.11(br, 1H), 8.31(s, 1H), 8.37(d, J=5 Hz, 1H).

PREPARATION 48

A solution of 2,3,4,5-tetrahydro-1H-pyrido[3,4-b]azepin-2-one (470 mg) in tetrahydrofuran (20 ml) was treated with lithium aluminum hydride (990 mg) and stirred at room temperature for 30 minutes. The excess hydride was decomposed with 28% ammonium hydroxide at 0° C. The resulting mixture was filtered through a bed of Celite and the Celite was washed with tetrahydrofuran, and the filtrate was concentrated. The residual aqueous layer was extracted with chloroform, dried over sodium sulfate, concentrated and purified by silica gel column chromatography (SiO₂; 20 g, 1% methanol in chloroform) to give 2,3,4,5-tetrahydro-1H-pyrido[3,4-b]azepine (370 mg).

¹H-NMR (300 MHz, CDCl₃, δ): 1.58–1.70(m, 2H), 1.76–1.88(m, 2H), 2.68–2.80(m, 2H1), 3.00–3.11(m, 2H), 3.90(brs, 1H), 6.98(d, J=5 Hz, 1H), 8.03(d, J=5 Hz, 1H), 8.07(s, 1H).

PREPARATION 49

Methyl 2-methoxy-4-(2,3,4,5-tetrahydro-1H-pyrido[3,4-b]azepin-1-yl)carbonylbenzoate was obtained in substantially the same manner as in Preparation 1.

¹H-NMR (300 MHz, CDCl₃, δ): 1.40–1.61(m, 1H), 1.80–2.27(m, 3H), 2.66–3.14(m, 3H), 3.76(s, 3H), 3.82(s, 3H), 5.07(m, 1H), 6.59(d, J=8 Hz, 1H), 6.90(s, 1H), 7.16(d, J=5 Hz, 1H), 7.53(d, J=8 Hz, 1H), 7.89(s, 1H), 8.28(d, J=5 Hz, 1H).

PREPARATION 50

2-Methoxy-4-(2,3,4,5-tetrahydro-1H-pyrido[3,4-b] azepin-1-yl)carbonylbenzoic acid was obtained in substantially the same manner as in Preparation 2.

¹H-NMR (300 MHz, CDCl₃, δ): 1.43–1.62(m, 1H), 1.90–2.26(m, 3H), 2.70–3.08(m, 3H), 4.00(s, 3H), 5.07(m, 1H), 6.58(d, J=8 Hz, 1H), 7.15(s, 1H), 7.21(d, J=5 Hz, 1H), 7.85(d, J=8 Hz, 1H), 7.90(s, 1H), 8.31(d, J=5 Hz, 1H).

EXAMPLE 96

N-[1-(tert-Butoxycarbonyl)-2-methyl-1H-benzimidazol-4-yl]-2-methoxy-4-(2,3,4,5-tetrahydro-1H-pyrido[3,4-b]azepin-1-yl)carbonylbenzamide was obtained in substantially the same manner as in Example 1.

¹H-NMR (300 MHz, CDCl₃, δ): 1.51(m, 1H), 1.71(s, 9H), 1.96–2.25(m,3H), 2.83(s, 3H), 2.74–3.14(m, 2H), 4.10(s, 3H), 5.10(m, 1H), 6.64(d, J=8 Hz, 1H), 7.12(s, 1H), 7.18(d, J=5 Hz, 1H), 7.28(dd, J=8, 8 Hz, 1H), 7.57(d, J=8 Hz, 1H), 7.91(s, 1H), 8.04(d, J=8 Hz, 1H), 8.28(d, J=5 Hz, 1H), 8.39(d, J=8 Hz, 1H).

EXAMPLE 97

2-Methoxy-N-(2-methyl-1H-benzimidazol-4-yl)-4-(2,3,4,5-tetrahydro-1H-pyrido(3,4-b]azepin-1-yl) carbonylbenzamide was obtained in substantially the same manner as in Example 2.

¹H-NMR (300 MHz, CDCl₃—CD₃OD=2/1, δ): 1.56(m, 1H), 1.98–2.11(m, 2H), 2.20(m, 1H), 2.60(s, 3H), 2.76–3.17 (m, 2H), 3.39(m, 1H), 4.04(s, 3H), 5.07(m, 1H), 6.68(d, J=8 Hz, 1H), 7.11(s, 1H), 7.18(m, 1H), 7.27(d, J=5 Hz, 1H), 7.88(s, 1H), 7.96(d, J=8 Hz, 1H), 8.26(d, J=5 Hz, 1H).

EXAMPLE 98

2-Methoxy-N-(2-methyl-1H-benzimidazol-4-yl)-4-(2,3,4,5-tetrahydro-1H-pyrido[3,4-b]azepin-1-yl) carbonylbenzamide dihydrochloride was obtained in substantially the same manner as in Example 10.

¹H-NMR (300 MHz, DMSO-d₆, δ): 1.34–2.20(m, 4H), 2.70–3.40(m, 5H), 3.68–4.08(m, 4H), 4.86(m, 1H), 6.87(m, 1H), 7.10(br, 1H), 7.40–7.64(m, 4H), 7.71(m, 1H), 7.94(br, 1H), 7.47–7.68(m, 2H).

PREPARATION 51

5-Hydroxyimino-2-methyl-5,6,7,8-tetrahydroquinoline was obtained in substantially the same manner as in Preparation 45.

$^1$H-NMR (300 MHz, DMSO-d$_6$, δ): 1.75–1.88(m, 2H), 2.43(s, 3H), 2.66(t, J=7 Hz, 2H), 2.81(t, J=7 Hz, 2H), 7.11(d, J=8 Hz, 1H), 8.06(d, J=8 Hz, 1H).

PREPARATION 52

2-Methyl-5-(4-methylphenylsulfonyl)oxyimino-5,6,7,8-tetrahydroquinoline was obtained in substantially the same manner as in Preparation 46.

$^1$H-NMR (300 MHz, CDCl$_3$, δ): 1.86–1.99(m, 2H), 2.46 (s, 3H), 2.53(s, 3H), 2.79–2.94(m, 4H), 7.01(d, J=8 Hz, 1H), 7.35(d, J=8 Hz, 2H), 7.91(d, J=8 Hz, 2H), 8.02(d, J=8 Hz, 1H).

PREPARATION 53

2-Methyl-6,7,8,9-tetrahydro-5H-pyrido[3,2-b]azepin-6-one was obtained in substantially the same manner as in Preparation 47.

$^1$H-NMR (300 MHz, CDCl$_3$, δ): 2.30–2.43(m, 4H), 2.53 (s, 3H), 3.02(d, J=7 Hz, 2H), 7.04(d, J=8 Hz, 1H), 7.17(d, J=8 Hz, 1H), 7.67(brs, 1H).

PREPARATION 54

2-Methyl-6,7,8,9-tetrahydro-5H-pyrido[3,2-b]azepine was obtained in substantially the same manner as in Preparation 48.

$^1$H-NMR (300 MHz, CDCl$_3$, δ): 1.63–1.75(m, 2H), 1.76–1.88(m, 2H), 2.43(s, 3H), 2.92–3.08(m, 4H), 3.57(brs, 1H), 6.81(d, J=8 Hz, 1H), 6.92(d, J=8 Hz, 1H).

PREPARATION 55

Methyl 2-methoxy-4-(2-methyl-6,7,8,9-tetrahydro-5H-pyrido[3,2-b]azepin-5-yl)carbonylbenzoate was obtained in substantially the same manner as in Preparation 1.

$^1$H-NMR (300 MHz, CDCl$_3$, δ): 1.62(br, 1H), 1.90–2.20 (m, 3H), 2.46(s, 3H), 2.76(m, 1H), 3.12–3.23(m, 2H), 3.74 (s, 3H), 3.84(s, 3H), 6.67–6.76(m, 2H), 6.80(d, J=8 Hz, 1H), 6.87(s, 1H), 7.56(d, J=8 Hz, 1H).

PREPARATION 56

2-Methoxy-4-(2-methyl-6,7,8,9-tetrahydro-5H-pyrido[3,2-b]azepin-5-yl)carbonylbenzoic acid was obtained in substantially the same manner as in Preparation 2.

$^1$H-NMR (300 MHz, CDCl$_3$, δ): 1.52–1.74(m, 1H), 1.90–2.23(m, 3H), 2.51(s, 3H), 2.79(br, 1H), 3.08–3.33(m, 2H), 3.94(s, 3H), 5.00(br, 1H), 6.69–6.91(m, 3H), 7.02(s, 1H), 7.91(d, J=8 Hz, 1H).

EXAMPLE 99

N-[1-(tert-Butoxycarbonyl)-2-methyl-1H-benzimidazol-4-yl]-2-methoxy-4-(2-methyl-6,7,8,9-tetrahydro-5H-pyrido[3,2-b]azepin-5-yl)carbonylbenzamide was obtained in substantially the same manner as in Example 1.

$^1$H-NMR (300 MHz, CDCl$_3$, δ): 1.57–1.66(m, 1H), 1.71 (s, 9H), 1.94–2.20(m, 3H), 2.48(s, 3H), 2.77(br, 1H), 2.82(s, 3H), 3.18–3.26(m, 2H), 4.02(s, 3H), 5.03(m, 1H), 6.73(d, J=8 Hz, 1H), 6.78–6.86(m, 2H), 6.99(s, 1H), 7.30(d, J=8 Hz, 1H), 7.58(d, J=8 Hz, 1H), 8.09(d, J=8 Hz, 1H), 8.40(d, J=8 Hz, 1H).

EXAMPLE 100

2-Methoxy-N-(2-methyl-1H-benzimidazol-4-yl)-4-(2-methyl-6,7,8,9-tetrahydro-5H-pyrido[3,2-b]azepin-5-yl) carbonylbenzamide was obtained in substantially the same manner as in Example 2.

$^1$H-NMR (300 MHz, CDCl$_3$, δ): 1.56–1.72(m, 1H), 1.93–2.22(m, 3H), 2.48(s, 3H), 2.61(s, 3H), 2.78(m, 1H), 3.16–3.28(m, 2H), 3.97(brs, 3H), 5.04(m, 1H), 6.67–9.61(m, 9H).

EXAMPLE 101

2-Methoxy-N-(2-methyl-1H-benzimidazol-4-yl)-4-(2-methyl-6,7,8,9-tetrahydro-5H-pyrido[3,2-b]azepin-5-yl) carbonylbenzamide dihydrochloride was obtained in substantially the same manner as in Example 10.

$^1$H-NMR (300 MHz, DMSO-d$_6$, δ): 1.51–1.73(br, 1H), 1.82–2.18(m, 3H), 2.54–2.97(m, 7H), 3.26–3.70(m, 2H), 3.84(brs, 3H), 4.84(m, 1H), 6.87(br, 1H), 7.20(br, 1H), 7.36–7.64(m, 4H), 7.70(d, J=8 Hz, 1H), 7.90(br, 1H).

PREPARATION 57

5-(4-Methylphenylsulfonyl)oxyimino-5,6,7,8-tetrahydroisoquinoline was obtained in substantially the same manner as in Preparation 46.

$^1$H-NMR (300 MHz, CDCl$_3$, δ): 1.82–1.95(m, 2H), 2.46 (s, 3H), 2.76(t, J=7 Hz, 2H), 2.86(t, J=7 Hz, 2H), 7.37(d, J=8 Hz, 2H), 7.63(d, J=5 Hz, 1H), 7.93(d, J=8 Hz, 2H), 8.45(d, J=5 Hz, 1H), 8.50(s, 1H).

PREPARATION 58

2,3,4,5-Tetrahydro-1H-pyrido[4,3-b]azepin-2-one was obtained in substantially the same manner as in Preparation 47.

$^1$H-NM (300 MHz, CDCl$_3$, δ): 2.22–2.36(m, 2H), 2.47(t, J=7 Hz, 2H), 2.84(t, J=7 Hz, 2H), 6.87(d, J=5 Hz, 1H), 8.22(brs, 1H), 8.41–8.48(m, 2H).

PREPARATION 59

2,3,4,5-Tetrahydro-1H-pyrido[4,3-b]azepine was obtained in substantially the same manner as in Preparation 48.

$^1$H-NMR (300 MHz, CDCl$_3$, δ): 1.65–1.90(m, 4H), 2.67–2.82(m, 2H), 3.14–3.26(m, 2H), 4.26(brs, 1H), 6.49(d, J=5 Hz, 1H), 8.07(d, J=5 Hz, 1H), 8.12(s, 1H).

PREPARATION 60

Methyl 2-methoxy-4-(2,3,4,5-tetrahydro-1H-pyrido[4,3-b]azepin-1-yl)carbonylbenzoate was obtained in substantially the same manner as in Preparation 1.

$^1$H-NMR (300 MHz, CDCl$_3$, δ): 1.79(br, 1H), 1.92–2.06 (m, 2H), 2.92–3.03(m, 2H), 3.76(s, 3H), 3.83(s, 3H), 6.54 (brs, 1H), 6,67(d, J=8 Hz, 1H), 6.94(s, 1H), 7.56(d, J=8 Hz, 1H), 8.18(d, J=5 Hz, 1H), 8.50(s, 1H).

PREPARATION 61

2-Methoxy-4-(2,3,4,5-tetrahydro-1H-pyrido[4,3-b] azepin-1-yl)carbonylbenzoic acid was obtained in substantially the same manner as in Preparation 2.

$^1$H-NMR (300 MHz, CDCl$_3$-CD$_3$OD=2/1, δ): 1.69–2.18 (m, 3H), 2.83–3.34(m, 3H), 3.74(s, 3H), 6.44–6.86(m, 2H), 6.92(s, 1H), 7.49(d, J=8 Hz, 1H), 8.09–8.22(m, 1H), 8.43–8.53(m, 1H).

EXAMPLE 102

N-[1-(tert-Butoxycarbonyl)-2-methyl-1H-benzimidazol-4-yl]-2-methoxy-4-(2,3,4,5-tetrahydro-1H-pyrido[4,3-b]azepin-1-yl)carbonylbenzamide was obtained in substantially the same manner as in Example 1.

$^1$H-NMR (300 MHz, CDCl$_3$, δ): 1.68(m, 1H), 1.71(s, 9H), 1.92–2.10(m, 3H), 2.82(s, 3H), 2.96–3.06(m, 2H), 4.04(s, 3H), 6.57(br, 1H), 6.82(d, J=8 Hz, 1H), 7.05(s, 1H), 7.29(m, 1H), 7.57(d, J=8 Hz, 1H), 8.10(d, J=8 Hz, 1H), 8.18(d, J=5 Hz, 1H), 8.40(d, J=8 Hz, 1H), 8.52(s, 1H).

EXAMPLE 103

2-Methoxy-N-(2-methyl-1H-benzimidazol-4-yl)-4-(2,3,4,5-tetrahydro-1H-pyrido[4,3-b]azepin-1-yl)carbonylbenzamide was obtained in substantially the same manner as in Example 2.

$^1$H-NMR (300 MHz, CDCl$_3$, δ): 1.58–2.09(m, 4H), 2.11 (s, 3H), 2.94–3.07(m, 2H), 3.91–4.07(m, 3H), 6.57(br, 1H), 6.71–7.23(m, 4H), 7.52 and 8.29(m, Total 1H), 8.07(d, J=8 Hz, 1H), 8.19(d, J=5 Hz, 1H), 8.54(s, 1H), 9.48 and 10.05 (m, total 1H), 10.77–10.96(m, 1H).

EXAMPLE 104

2-Methoxy-N-(2-methyl-1H-benzimidazol-4-yl)-4-(2,3,4,5-tetrahydro-1H-pyrido[4,3-b]azepin-1-yl)carbonylbenzamide dihydrochloride was obtained in substantially the same manner as in Example 10.

$^1$H-NMR (300 MHz, DMSO-d$_6$, δ): 1.68–1.97(m, 4H), 2.80(s, 3H), 3.08–3.23(m, 2H), 3.82(s, 3H), 3.67–4.08(br, 1H), 6.92(d, J=8 Hz, 1H), 7.20(s, 1H), 7.42–7.53(m, 2H), 7.53–7.65(m, 2H), 7.73(d, J=8 Hz, 1H), 8.55(d, J=5 Hz, 1H), 8.91(s, 1H).

PREPARATION 62

Methyl 2-methoxy-4-(2,3,4,5-tetrahydro-1,5-benzoxazepin-5-yl)-carbonylbenzoate was obtained in substantially the same manner as in Preparation 1.

$^1$H-NMR (300 MHz, CDCl$_3$, δ): 3.62(s, 3H), 3.78(s, 3H), 6.58(d, J=8 Hz, 1H), 6.66–6.74(m, 1H), 6.76(s, 1H), 7.02–7.10(m, 2H), 7.54(d, J=8 Hz, 1H).

PREPARATION 63

2-Methoxy-4-(2,3,4,5-tetrahydro-1,5-benzoxazepin-5-yl)carbonylbenzoic acid was obtained in substantially the same manner as in Preparation 2.

$^1$H-NMR (300 MHz, CDCl$_3$, δ): 3.86(s, 3H), 6.64(d, J=8 Hz, 1H), 6.72–6.81(m, 1H), 6.91(s, 1H), 7.10–7.19(m, 2H), 7.96(d, J=8 Hz, 1H).

EXAMPLE 105

N-[1-(tert-Butoxycarbonyl)-2-methyl-1H-benzimidazol-4-yl]-2-methoxy-4-(2,3,4,5-tetrahydro-1,5-benzoxazepin-5-yl)carbonylbenzamide was obtained in substantially the same manner as in Example 1.

$^1$H-NMR (300 MHz, CDCl$_3$, δ): 1.69(s, 9H×0.33), 1.71(s, 9H×0.66), 2.79(s, 3H×0.33), 2.82(s, 3H×0.66), 3.75(s, 3H×0.33), 3.95(s, 3H×0.66), 6.50–7.62(m, 8H), 7.93–8.18 (m, 2.33H), 8.40(d, J=8 Hz, 1H×0.66).

EXAMPLE 106

2-Methoxy-N-(2-methyl-1H-benzimidazol-4-yl)-4-(2,3,4,5-tetrahydro-1,5-benzoxazepin-5-yl)carbonylbenzamide was obtained in substantially the same manner as in Example 2.

$^1$H-NMR (300 MHz, CDCl$_3$, δ): 2.60(s, 3H), 3.88(brs, 3H), 6.67(d, J=8 Hz, 1H), 6.72–6.82(m, 1H), 6.88(s, 1H), 7.03(d, J=8 Hz, 1H), 7.03–7.18(m, 3H), 8.10(d, J=8 Hz, 1H).

PREPARATION 64

Methyl 2-methoxy-4-(2,3,4,5-tetrahydro-1,5-benzothiazepin-5-yl)carbonylbenzoate was obtained in substantially the same manner as in Preparation 1.

$^1$H-NMR (300 MHz, CDCl$_3$, δ): 2.05–2.30(m, 2H), 2.60–2.78(m, 2H), 2.83–2.94(m, 1H), 3.56(s, 3H), 3.70(s, 3H), 4.94(brd, J=12 Hz, 1H), 6.70(d, J=8 Hz, 1H), 6.80(s, 1H), 6.82–6.94(m, 2H), 6.99(t, J=8 Hz, 1H), 7.43–7.52(m, 2H).

PREPARATION 65

2-Methoxy-4-(2,3,4,5-tetrahydro-1,5-benzothiazepin-5-yl)-carbonylbenzoic acid was obtained in substantially the same manner as in Preparation 2.

$^1$H-NMR (300 MHz, CDCl$_3$, δ): 2.18–2.46(m, 2H), 2.73–2.91(m, 2H), 2.95–3.05(m, 1H), 3.84(s, 3H), 5.05(brd, J=12 Hz, 1H), 6.80(d, J=8 Hz, 1H), 6.98–7.18(m, 4H), 7.60(d, J=8 Hz, 1H), 7.98(d, J=8 Hz, 1H).

EXAMPLE 107

N-[1-(tert-Butoxycarbonyl)-2-methyl-1H-benzimidazol-4-yl]-2-methoxy-4-(2,3,4, 5-tetrahydro-1,5-benzothiazepin-5-yl)carbonylbenzamide was obtained in substantially the same manner as in Example 1.

$^1$H-NMR (300 MHz, CDCl$_3$, δ): 1.69(s, 9H×0.33), 1.71(s, 9H×0.66), 2.79(s, 3H×0.33), 2.82(s, 3H×0.66), 3.75(s, 3H×0.33), 3.94(s, 3H×0.66), 6.75–7.65(m, 8H), 7.93–8.15 (m, 2.33H), 8.38(d, J=8 Hz, 1H×0.66).

EXAMPLE 108

2-Methoxy-N-(2-methyl-1H-benzimidazol-4-yl)-4-(2,3,4,5-tetrahydro-1,5-benzothiazepin-5-yl)carbonylbenzamide was obtained in substantially the same manner as in Example 2.

$^1$H-NMR (300 MHz, CDCl$_3$, δ): 2.18–2.46(m, 2H), 2.60 (s, 3H), 2.75–2.83(m, 2H), 2.93–3.02(m, 1H), 3.88(s, 3H), 5.12(brd, J=15 Hz, 1H), 6.81(d, J=8 Hz, 1H), 6.95–7.06(m, 2H), 7.06–7.18(m, 3H), 7.25(s, 1H), 7.25–7.52(brs, 1H), 7.61(d, J=8 Hz, 1H), 8.12(d, J=8 Hz, 1H).

EXAMPLE 109

To a solution of 2-methoxy-N-(2-methyl-1H-benzimidazol-4-yl)-4-(2,3,4,5-tetrahydro-1,5-benzothiazepin-5-yl)carbonylbenzamide (20 mg) in AcOH (1 ml), was added 30% aqueous H$_2$O$_2$ (1 ml), and the mixture was stirred for 4 hours. Saturated aqueous NaHCO$_3$ was added to the reaction mixture, and the mixture was extracted with AcOEt, washed with brine and dried over Na$_2$CO$_3$. The solvent was removed under reduced pressure to give 2-methoxy-N-(2-methyl-1H-benzimidazol-4-yl)-4-(1-oxo-2,3,4,5-tetrahydro-1,5-benzothiazepin-5-yl)carbonylbenzamide (20 mg).

$^1$H-NMR (300 MHz, CDCl$_3$, δ): 2.20–2.32(m, 1H), 2.58 (s, 3H), 2.58–2.86(m, 2H), 3.17(t, J=12 Hz, 1H), 3.43–3.55 (m, 1H), 3.92(s, 3H), 4.98(brd, J=12 Hz, 1H), 6.82(d, J=8 Hz, 1H), 7.00(s, 1H), 7.06(d, J=8 Hz, 1H), 7.16(t, J=8 Hz, 1H), 7.22–7.46(m, 4H), 7.53(t, J=8 Hz, 1H), 7.91(d, J=8 Hz, 1H), 8.11(d, J=8 Hz, 1H).

EXAMPLE 110

To a solution of 2-methoxy-N-(2-methyl-1H-benzimidazol-4-yl)-4-(1-oxo-2,3,4,5-tetrahydro-1,5- benzothiazepin-5-yl)carbonylbenzamide (164 mg) in TFA (1 ml), was added 30% aqueous $H_2O_2$ (1 ml) and the mixture was stirred for 4 hours. Saturated aqueous $NaHCO_3$ was added to the reaction mixture, and the mixture was extracted with AcOEt, washed with brine and dried over $Na_2CO_3$. The solvent was removed under reduced pressure to give 2-methox-N-(2-methyl-1H-benzimidazol-4-yl)-4-(1,1-dioxo-2,3,4,5-tetrahydro-1,5-benzothiazepin-5-yl)carbonylbenzamide (160 mg).

$^1$H-NMR (300 MHz, $CDCl_3$, δ): 2.18(brd, J=15 Hz, 1H), 2.56(s, 3H), 2.60–2.92(m, 2H), 3.22(t, J=10 Hz, 1H), 3.42–3.63(m, 3H), 3.80(s, 3H), 5.25(brd, J=15 Hz, 1H), 6.85(d, J=8 Hz, 1H), 7.10(t, J=8 Hz, 1H), 7.19(s, 1H), 7.19–7.46(m, 5H), 8.15(d, J=8 Hz, 1H).

PREPARATION 66

Methyl 2-methoxy-4-(4-methyl-2,3,4,5-tetrahydro-1H-1,4-benzodiazepin-1-yl)carbonylbenzoate was obtained in substantially the same manner as in Preparation 1.

$^1$H-NMR (300 MHz, $CDCl_3$, δ): 2.18(brd, J=15 Hz, 1H), 2.56(s, 3H), 2.60–2.92(m, 2H), 3.22(t, J=10 Hz, 1H), 3.42–3.63(m, 3H), 3.80(s, 3H), 5.25(brd, J=15 Hz, 1H), 6.85(d, J=8 Hz, 1H), 7.10(t, J=8 Hz, 1H), 7.19(s, 1H), 7.19–7.46(m, 5H), 8.15(d, J=8 Hz, 1H).

PREPARATION 67

2-Methoxy-4-(4-methyl-2,3,4,5-tetrahydro-1H-1,4-benzodiazepin-1-yl)carbonylbenzoic acid was obtained in substantially the same manner as in Preparation 2.

$^1$H-NMR (300 MHz, $CDCl_3$, δ): 2.18(brd, J=15 Hz, 1H), 2.56(s, 3H), 2.60–2.92(m, 2H), 3.22(t, J=10 Hz, 1H), 3.42–3.63(m, 3H), 3.80(s, 3H), 5.25(brd, J=15 Hz, 1H), 6.85(d, J=8 Hz, 1H), 7.10(t, J=8 Hz, 1H), 7.19(s, 1H), 7.19–7.46(m, 5H), 8.15(d, J=8 Hz, 1H).

EXAMPLE 111

N-[1-(tert-Butoxycarbonyl)-2-methyl-1H-benzimidazol-4-yl]-2-methoxy-4-(4-methyl-2,3,4,5-tetrahydro-1H-1,4-benzodiazepin-1-yl)carbonylbenzamide was obtained in substantially the same manner as in Example 1.

$^1$H-NMR (300 MHz, $CDCl_3$, δ): 2.18(brd, J=15 Hz, 1H), 2.56(s, 3H), 2.60–2.92(m, 2H), 3.22(t, J=10 Hz, 1H), 3.42–3.63(m, 3H), 3.80(s, 3H), 5.25(brd, J=15 Hz, 1H), 6.85(d, J=8 Hz, 1H), 7.10(t, J=8 Hz, 1H), 7.19(s, 1H), 7.19–7.46(m, 5H), 8.15(d, J=8 Hz, 1H).

EXAMPLE 112

2-Methoxy-N-(2-methyl-1H-benzimidazol-4-yl)-4-(4-methyl-2,3,4,5-tetrahydro-1H-1,4-benzodiazepin-1-yl)carbonylbenzamide was obtained in substantially the same manner as in Example 2.

$^1$H-NMR (300 MHz, $CDCl_3$, δ): 2.38(s, 3H), 2.46(s, 3H), 2.92–3.18(m, 4H), 3.66–3.83(m, 4H), 4.03(brd, J=15 Hz, 1H), 4.85(brd, J=15 Hz, 1H), 6.59(d, J=8 Hz, 1H), 6.78(d, J=8 Hz, 1H), 6.93(t, J=8 Hz, 1H), 6.98–7.17(m, 3H), 7.23(d, J=8 Hz, 1H), 7.56–7.85(brs, 1H), 7.98(d, J=8 Hz, 1H).

PREPARATION 68

Methyl 2-methoxy-4-(1,2,3,5-tetrahydro-4,1-benzoxazepin-1-yl)carbonylbenzoate was obtained in substantially the same manner as in Preparation 1.

$^1$H-NMR (300 MHz, $CDCl_3$, δ): 3.00–3.20(m, 1H), 3.72(s, 3H), 3.85(s, 3H), 3.85–4.07(m, 1H), 4.05–4.25(m, 1H), 4.80(s, 2H), 5.56(brd, J=8 Hz, 1H), 6.69(m, 2H), 6.90(s, 1H), 7.02(t, J=8 Hz, 1H), 7.15(t, J=8 Hz, 1H), 7.32(d, J=8 Hz, 1H), 7.54(d, J=8 Hz, 1H).

PREPARATION 69

2-Methoxy-4-(1,2,3,5-tetrahydro-4,1-benzoxazepin-1-yl)carbonylbenzoic acid was obtained in substantially the same manner as in Preparation 2.

$^1$H-NMR (300 MHz, $CDCl_3$, δ): 3.06–3.22(m, 1H), 3.82–4.05(m, 1H), 3.92(s, 1H), 4.13–4.28(m, 1H), 4.82(s, 2H), 5.05(brd, J=12 Hz, 1H), 6.67(d, J=8 Hz, 1H), 6.72(d, J=8 Hz, 1H), 6.98–7.10(m, 2H), 7.18(t, J=8 Hz, 1H), 7.34(d, J=8 Hz, 1H), 7.87(d, J=8 Hz, 1H).

EXAMPLE 113

N-[1-(tert-Butoxycarbonyl)-2-methyl-1H-benzimidazol-4-yl]-2-methoxy-4-(1,2,3,5-tetrahydro-4,1-benzoxazepin-1-yl)carbonylbenzamide was obtained in substantially the same manner as in Example 1.

$^1$H-NMR (300 MHz, $CDCl_3$, δ): 1.70(s, 9H), 2.32(s, 3H), 3.04–3.16(m, 1H), 3.89–4.02(m, 1H), 4.00(s, 3H), 4.15–4.26(m, 1H), 4.83(s, 2H), 5.09(brd, J=8 Hz, 1H), 6.70(d, J=8 Hz, 1H), 6.79(d, J=8 Hz, 1H), 6.94–7.08(m, 3H), 7.56(d, J=8 Hz, 1H), 8.04(d, J=8 Hz, 1H), 8.40(d, J=8 Hz, 1H).

EXAMPLE 114

2-Methoxy-N-(2-methyl-1H-benzimidazol-4-yl)-4-(1,2,3,5-tetrahydro-4,1-benzoxazepin-1-yl)carbonylbenzamide was obtained in substantially the same manner as in Example 2.

$^1$H-NMR (300 MHz, $CDCl_3$, δ): 2.61(s, 3H), 3.04–3.22(m, 1H), 3.88–4.04(m, 1H), 4.15–4.26(m, 4H), 4.83(s, 2H), 5.10(brd, J=8 Hz, 1H), 6.70(d, J=8 Hz, 1H), 6.80(d, J=8 Hz, 1H), 7.00–7.08(m, 2H), 7.11–7.21(m, 2H), 7.34(d, J=8 Hz, 1H), 8.06(d, J=8 Hz, 1H).

PREPARATION 70

Methyl 2-methoxy-4-(1,2,3,5-tetrahydro-4,1-benzothiazepin-1-yl)carbonylbenzoate was obtained in substantially the same manner as in Preparation 1.

$^1$H-NMR (300 MHz, $CDCl_3$, δ): 2.81(brd, J=12 Hz, 1H), 3.07–3.18(m, 1H), 3.22–3.38(m, 1H), 3.62(d, J=18 Hz, 1H), 3.72(s, 3H), 3.82(s, 3H), 4.27(d, J=12 Hz, 1H), 5.23(brd, J=12 Hz, 1H), 6.68–6.78(m, 2H), 6.86(s, 1H), 7.00(t, J=8 Hz, 1H), 7.17(t, J=8 Hz, 1H), 7.22–7.30(m, 2H), 7.53(d, J=8 Hz, 1H).

PREPARATION 71

2-Methoxy-4-(1,2,3,5-tetrahydro-4,1-benzothiazepin-1-yl)carbonylbenzoic acid was obtained in substantially the same manner as in Preparation 2.

$^1$H-NMR (300 MHz, $CDCl_3$, δ): 2.81(brd, J=12 Hz, 1H), 3.08–3.19(m, 1H), 3.25–3.34(m, 1H), 3.66(d, J=18 Hz, 1H), 3.92(s, 3H), 4.25(d, J=12 Hz, 1H), 5.20(brd, J=12 Hz, 1H), 6.70–6.78(m, 2H), 7.00(t, J=8 Hz, 1H), 7.04(s, 1H), 7.20(t, J=8 Hz, 1H), 7.29(d, J=8 Hz, 1H), 7.90(d, J=8 Hz, 1H).

EXAMPLE 115

N-[1-(tert-Butoxcarbonyl)-2-methyl-1H-benzimidazol-4-yl]-2-methoxy-4-(1,2,3,5-tetrahydro-4,1-benzothiazepin-1-yl)carbonylbenzamide was obtained in substantially the same manner as in Example 1.

$^1$H-NMR (300 MHz, $CDCl_3$, δ): 1.72(s, 9H), 2.79–2.82(m, 1H), 2.82(s, 3H), 3.09–3.19(m, 1H), 3.28–3.30(m, 1H), 3.67(d, J=18 Hz, 1H), 4.02(s, 3H), 4.30(d, J=18 Hz, 1H), 5.26(brd, J=12 Hz, 1H), 6.76(d, J=8 Hz, 1H), 6.80(d, J=8 Hz, 1H), 6.96–7.02(m, 2H), 7.16(t, J=8 Hz, 1H), 7.22–7.31(m, 2H), 7.56(d, J=8 Hz, 1H), 8.05(d, J=8 Hz, 1H), 8.39(d, J=8 Hz, 1H).

EXAMPLE 116

2-Methoxy-N-(2-methyl-1H-benzimidazol-4-yl)-4-(1,2,3,5-tetrahydro-4,1-benzothiazepin-1-yl)carbonylbenzamide was obtained in substantially the same manner as in Example 2.

$^1$H-NMR (300 MHz, CDCl$_3$, δ): 2.62(s, 3H), 2.83(dd, J=15, 3 Hz, 1H), 3.14(t, J=14 Hz, 1H), 3.22(t, J=14 Hz, 1H), 3.68(d, J=18 Hz, 1H), 3.96(brs, 3H), 4.30(d, J=18 Hz, 1H), 5.24(dd, J=15, 3 Hz, 1H), 6.75(d, J=8 Hz, 1H), 6.82(d, J=8 Hz, 1H), 6.97–7.07(m, 2H), 7.10–7.23(m, 2H), 7.30(d, J=8 Hz, 1H), 8.04(d, J=8 Hz, 1H).

EXAMPLE 117

2-Methoxy-N-(2-methyl-1H-benzimidazol-4-yl)-4-(4-oxo-1,2,3,5-tetrahydro-4,1-benzothiazepin-1-yl)carbonylbenzamide was obtained in substantially the same manner as in Example 109.

$^1$H-NMR (300 MHz, CDCl$_3$, δ): 2.60(s, 3H), 3.07–3.34 (m, 2H), 4.00(brs, 3H), 4.33(brs, 2H), 4.86(brd, J=15 Hz, 1H), 6.69–6.85(m, 2H), 7.03–7.21(m, 3H), 7.21–7.45(m, 5H), 8.03(d, J=8 Hz, 1H).

EXAMPLE 118

2-Methoxy-N-(2-methyl-1H-benzimidazol-4-yl)-4-(4,4-dioxo-1,2,3,5-tetrahydro-4,1-benzothiazepin-1-yl)carbonylbenzamide was obtained in substantially the same manner as in Example 110.

$^1$H-NMR (300 MHz, CDCl$_3$, δ): 2.62(s, 3H), 3.30(brd, J=15 Hz, 1H), 3.63(t, J=12 Hz, 1H), 3.83(t, J=12 Hz, 1H), 4.06(s, 3H), 4.16(d, J=18 Hz, 1H), 5.70(brd, J=15 Hz, 1H), 6.72(d, J=8 Hz, 1H), 6.83(d, J=8 Hz, 1H), 7.07–7.44(m, 8H), 8.02(d, J=8 Hz, 1H).

EXAMPLE 119

To a suspension of 2-methoxy-N-(2-methyl-1H-benzimidazol-4-yl)-4-(2,3,4,5-tetrahydro-1H-1-benzazepin-1-yl)carbonylbenzamide (30.1 g, 66.2 mmol) in ethanol (150 ml) was added a solution of methanesulfonic acid (6.68 g, 69.5 mmol) in ethanol (60 ml) at 0° C. The resulting mixture was allowed to warm to room temperature and stirred for 30 minutes. After removal of insoluble material, the solution was concentrated to give amorphous solid (39.5 g). This amorphous was dissolved in hot water (190 ml) and stirred at room temperature. The precipitated crystal was filtered and washed with ice-cold water (100 ml). The collected crystal as dried to give 30 g of 2-methoxy-N-(2-methyl-1H-benzimidazol-4-yl)-4-(2,3,4,5-tetrahydro-1H-1-benzazepin-1-yl)carbonylbenzamide methanesulfonate as a white crystal.

$^1$H-NMR (300 MHz, DMSO-d$_6$, δ): 1.42(m, 1H), 1.82–1.97(m, 2H), 2.06(m, 1H), 2.31(s, 3H), 2.73(m, 1H), 2.76(s, 3H), 2.89(m, 1H), 3.06(m, 1H), 3.75(s, 3H), 4.84(m, 1H), 6.86(dd, J=8, 8 Hz, 1H), 6.94–7.03(m, 2H), 7.13(dd, J=8, 8 Hz, 1H), 7.32(d, J=8 Hz, 1H), 7.41–7.53(m, 2H), 7.58(d, J=8 Hz, 1H), 7.63(d, J=8 Hz, 1H).

This application is based on application No. PP1500/98 filed in Australia, the content of which are incorporated hereinto by reference.

What is claimed is:

1. A compound of formula (I):

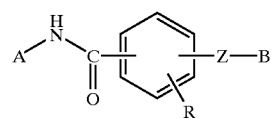

(I)

wherein

A is an optionally substituted heterocyclic group;

R is a lower alkoxy;

Z is C=O or CH$_2$; and

B is benzazepinyl that may be optionally substituted, or a salt thereof.

2. A compound of formula (II):

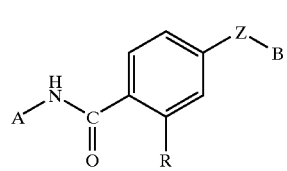

(II)

wherein

A is an optionally substituted heterocyclic group;

R is a lower alkoxy;

Z is C=O or CH$_2$; and

B is benzazepinyl that may be optionally substituted, or a salt thereof.

3. The compound of claim 1, wherein B is benzazepinyl substituted by one or more substituent(s) selected from the group consisting of lower alkyl, halogen, hydroxy, N-protective group, =O and =CH$_2$, or a salt thereof.

4. The compound of claim 1, wherein A is a heterocyclic group selected from the group consisting of benzimidazolyl, benzoxazolyl and indazolyl, each of which may be optionally substituted, or a salt thereof.

5. The compound of claim 1, wherein A is a heterocyclic group selected from the group consisting of benzimidazolyl, benzoxazolyl and indazolyl, each of which is substituted with one or more substituents selected from the group consisting of lower alkyl optionally substituted with hydroxy, protected hydroxy, amino, protected amino, alkyl-substituted amino, lower alkoxy, acylamino or N-containing heterocyclic group; N-protective group; lower alkoxy; haloalkyl; amino optionally substituted with lower alkyl, acyl or N-protective group; carbamoyl optionally substituted with lower alkyl; acyl; acylamino; aminoalkylamino optionally substituted with lower alkyl or N-protective group; and N-containing heterocyclic group optionally substituted with lower alkyl, amino optionally substituted with lower alkyl or N-protective group, or a salt thereof.

6. A process for preparing a compound of formula (I):

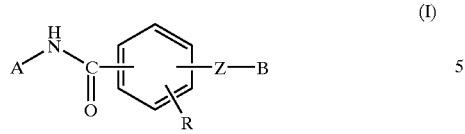

wherein
A is an optionally substituted heterocyclic group;
R is a lower alkoxy;
Z is C=O or CH$_2$; and
B is benzazepinyl that may be optionally substituted,
or a salt thereof,
  that comprises:
  1) reacting a compound of formula (III):

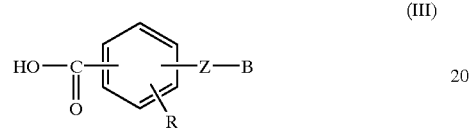

wherein B, Z and R are each as defined above,
or its reactive derivative at the carboxyl group or a salt thereof, with a compound of the formula (IV):

A—NH$_2$ wherein A is as defined above,
  or its reactive derivative at the amino group or a salt thereof,
  to give a compound of formula (I) or a salt thereof,
  or
  2) subjecting to an elimination reaction of an N-protective group at A$^1$ and/or B$^1$, a compound of formula (Ia):

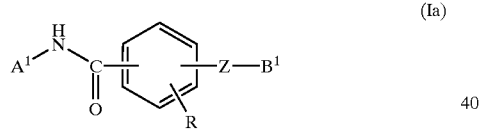

wherein
  A$^1$ is a heterocyclic group substituted with an N-protective group, a protected amino or a substituent having protected amino,
  B$^1$ is benzazepinyl, which is substituted with an N-protective group, a protected amino or a substituent having protected amino, and
  Z and R are each as defined above,
  or a salt thereof to give a compound of formula (Ib):

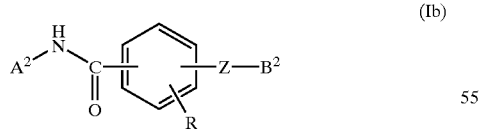

wherein
  A$^2$ is a heterocyclic group not substituted with an N-protective group or substituted with amino or a substituent having amino,
  B$^2$ is benzazepinyl, which is not substituted with an N-protective group or substituted with amino or a substituent having amnino, and
  Z and R are each as defined above,
  a salt thereof, or
  3) subjecting to reduction of =O at B$^3$, a compound of formula (Ic):

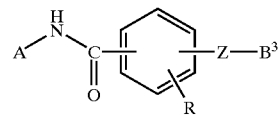

wherein
B$^3$ is benzazepinyl, which is substituted with =O, and
A, Z and R are each as defined above,
or a salt thereof,
to give a compound of formula (Id):

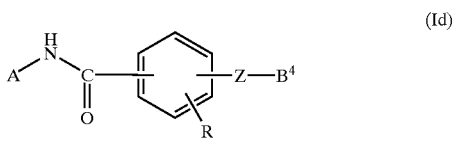

wherein
B$^4$ is benzazepinyl that is substituted with hydroxy, and
A, Z and R are each as defined above,
or a salt thereof; or
4) subjecting to hydrolysis a compound of formula (Ie):

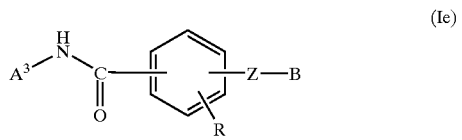

wherein
A$^3$ is a heterocyclic group substituted with phthaloylaminoalkyl, and
B, Z and R are each as defined above,
or a salt thereof,
to give a compound of formula (If):

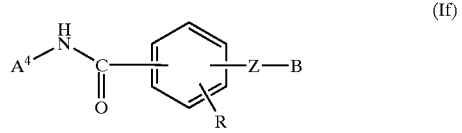

wherein
A$^4$ is a heterocyclic group substituted with aminoalkyl, and
B, Z and R are each as defined above,
or a salt thereof; or
5) reacting a compound of formula (Ig):

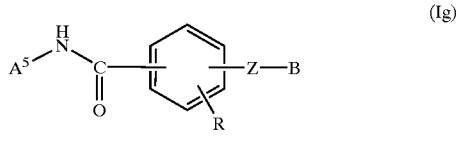

wherein
A$^5$ is a heterocyclic group substituted with amino or aminoalkyl, and
B, Z and R are each as defined above,
or a salt thereof,
with an alkylating agent to give a compound of formula (Ih):

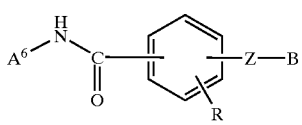

wherein
$A^6$ is a heterocyclic group substituted with (di)alkylamino or (di)alkylaminoalkyl, and
B, Z and R are each as defined above,
or a salt thereof; or 6) reacting a compound of formula (Ig) or a salt thereof, with an acylating agent to give a compound of formula (Ii):

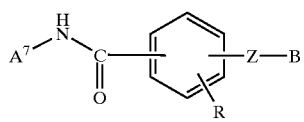

wherein
$A^7$ is a heterocyclic group substituted with acylamino or acylaminoalkyl, and
B, Z and R are each as defined above,
or a salt thereof; or 7) subjecting a compound of formula (Ij):

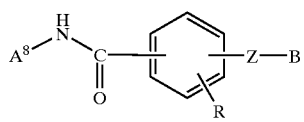

wherein
$A^8$ is a heterocyclic group substituted with protected hydroxyalkyl, and
B, Z and R are each as defined above,
or a salt thereof
to an elimination reaction of a hydroxy-protective group in $A^8$,
to give a compound of formula (Ik):

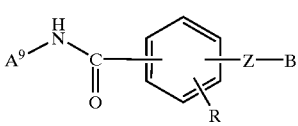

wherein
$A^9$ is a heterocyclic group substituted with hydroxyalkyl, and
B, Z and R are each as defined above,
or a salt thereof.

7. A pharmaceutical composition that comprises, as an active ingredient, a compound of claim 1 or a pharmaceutically acceptable salt thereof in admixture with a pharmaceutically acceptable carrier.

8. A method of the treatment of hypertension, heart failure, renal insufficiency, edema, ascites, vasopressin parasecretion syndrome, hepatocirrhosis, hyponatremia, hypokalemia, diabetes mellitus, circulation disorder, cerebrovascular disease, Meniere's syndrome, motion sickness, depressant or anxiety, which comprises administering an effective amount of a compound of claim 1 or a pharmaceutically acceptable salt thereof to a human being or animal in need thereof.

* * * * *